US012559746B2

(12) United States Patent (10) Patent No.: US 12,559,746 B2
Kahn et al. (45) Date of Patent: Feb. 24, 2026

(54) TARGETING micro-RNAs FOR EXOSOMAL DELIVERY OR CELLULAR RETENTION

(71) Applicant: Joslin Diabetes Center, Boston, MA (US)

(72) Inventors: C. Ronald Kahn, Falls Church, VA (US); Ruben Garcia Martin, Boston, MA (US)

(73) Assignee: Joslin Diabetes Center, Boston, MA (US)

( * ) Notice: Subject to any disclaimer, the term of this patent is extended or adjusted under 35 U.S.C. 154(b) by 1154 days.

(21) Appl. No.: 17/156,145

(22) Filed: Jan. 22, 2021

(65) Prior Publication Data

US 2021/0171949 A1 Jun. 10, 2021

Related U.S. Application Data

(63) Continuation of application No. PCT/US2019/043469, filed on Jul. 25, 2019.

(60) Provisional application No. 62/703,566, filed on Jul. 26, 2018.

(51) Int. Cl.
*C12N 15/113* (2010.01)
*A61K 35/34* (2015.01)
*A61K 35/35* (2015.01)
*A61K 35/407* (2015.01)
*A61K 35/44* (2015.01)

(52) U.S. Cl.
CPC ............ *C12N 15/113* (2013.01); *A61K 35/34* (2013.01); *A61K 35/35* (2013.01); *A61K 35/407* (2013.01); *A61K 35/44* (2013.01); *C12N 2310/141* (2013.01)

(58) Field of Classification Search
CPC ........... C12N 15/113; C12N 2310/141; A61K 35/34; A61K 35/35; A61K 35/407; A61K 35/44
See application file for complete search history.

(56) References Cited

U.S. PATENT DOCUMENTS

| | | | |
|---|---|---|---|
| 8,852,940 B2 * | 10/2014 | Blelloch ................. | A61P 25/16 435/325 |
| 2016/0130577 A1 * | 5/2016 | Sánchez Madrid .. | C12N 15/113 435/375 |
| 2016/0243171 A1 * | 8/2016 | Shiels ..................... | A61K 35/28 |
| 2017/0314028 A1 | 11/2017 | Hou et al. | |

FOREIGN PATENT DOCUMENTS

| | | |
|---|---|---|
| WO | 2016095934 A2 | 6/2016 |
| WO | 2016179417 A2 | 11/2016 |

OTHER PUBLICATIONS

Villarroya-Beltri, Carolina, et al. "Sumoylated hnRNPA2B1 controls the sorting of miRNAs into exosomes through binding to specific motifs." Nature communications 4.1 (2013): 2980. (Year: 2013).*
Ahn J et al., "MicroRNA-146b promotes adipogenesis by suppressing the SIRT1-FOXO1 cascade" EMBO Mol Med 10:1602-12 (2013).
Bartel D.P. "Metazoan MicroRNAs" Cell 173(1):20-51 (2018).
Calin et al., "Frequent deletions and down-regulation of micro-RNA genes miR15 and miR16 at 13q14 in chronic lymphocytic leukemia" Proc. Natl. Acad. Sci. USA (2002) 99,15524-15529.
Chen JF et al., "The role of microRNA-1 and microRNA-133 in skeletal muscle proliferation and differentiation" Nat Genet 38(2):228-33 (2006).
Dominguez D et al., "Sequence, Structure, and Context Preferences of Human RNA Binding Proteins" Mol Cell 70 (5):854-867.e9 (2018).
Dou L et al., "MiR-19a regulates PTEN expression to mediate glycogen synthesis in hepatocytes" Sci Rep 26(5):11602 (2015).
Esau C. et al., "miR-122 regulation of lipid metabolism revealed by in vivo antisense targeting" Cell Metab 3(2):87-98 (2006).
Fasshauer M et al., "Essential role of insulin receptor substrate-2 in insulin stimulation of Glut4 translocation and glucose uptake in brown adipocytes" J Biol Chem 275(33):25494-501 (2000).
Juliano et al, "The chemistry and biology of oligonucleotide conjugates" Acc. Chem. Res. 45: 1067-1076 (2012).
Lee et al. (1993) "The C. elegans heterochronic gene lin-4 encodes small RNAs with antisense complementarity to lin-14" Cell 75(5): 843-854.
Lindow, M., and Kauppinen, S. "Discovering the first microRNA-targeted drug" J. Cell Biol. 199, 407-412 (2012).
Rettig et al. "Progress toward in vivo use of siRNAs-II " Mol. Ther. 20(3): 483-512 (2012).
Ritchie ME et al., "limma powers differential expression analyses for RNA-sequencing and microarray studies" Nucleic Acids Research 43(7), e47 (2015).
Théry C et al., "Isolation and characterization of exosomes from cell culture supernatants and biological fluids" Curr Protoc Cell Biol Chapter 3: Unit 3.22 (2006).
Thomou et al., "Adipose-derived circulating miRNAs regulate gene expression in other tissues" Nature, 542:450-455 (2017).
Yuan et al., "Recent advances of siRNA delivery by nanoparticles" Expert Opin. Drug Deliv. (2011) 8:521-536.

(Continued)

*Primary Examiner* — Ekaterina Poliakova-Georgantas
*Assistant Examiner* — John Charles Mckillop
(74) *Attorney, Agent, or Firm* — McNeill PLLC

(57) ABSTRACT

Disclosed herein are exosomal sorting motifs and cellular retention motifs for microRNAs. Methods of use for directing miRNA to exosomes or retaining miRNA in cells are also disclosed.

9 Claims, 12 Drawing Sheets

Specification includes a Sequence Listing.

(56) References Cited

OTHER PUBLICATIONS

Zhao Y et al., "Dysregulation of cardiogenesis, cardiac conduction, and cell cycle in mice lacking miRNA-1-2" Cell 129 (2):303-317 (2007).

International Search Report and Written Opinion issued in PCT/US2019/043469 on Oct. 28, 2019.

Villarroya-Beltri et al., "Sumoylated hnRNPA2B1 controls the sorting of MiRNAs into exosomes through binding to specific motifs," Nature Communications, Dec. 20, 2013, vol. 4, pp. 1-10.

Chakraborty, C. et al. "Therapeutic miRNA and siRNA: Moving from Bench to Clinic as Next Generation Medicine" Molecular Therapy: Nucleic Acids vol. 8 (2017).

Santangelo, L. et al. "The RNA-Binding Protein SYNCRIP Is a Component of the Hepatocyte Exosomal Machinery Controlling MicroRNA Sorting" Cell Reports, 17:799-808 (2016).

* cited by examiner

Exosomes

Exosomes

3T3-L1
Exosome    Lysate
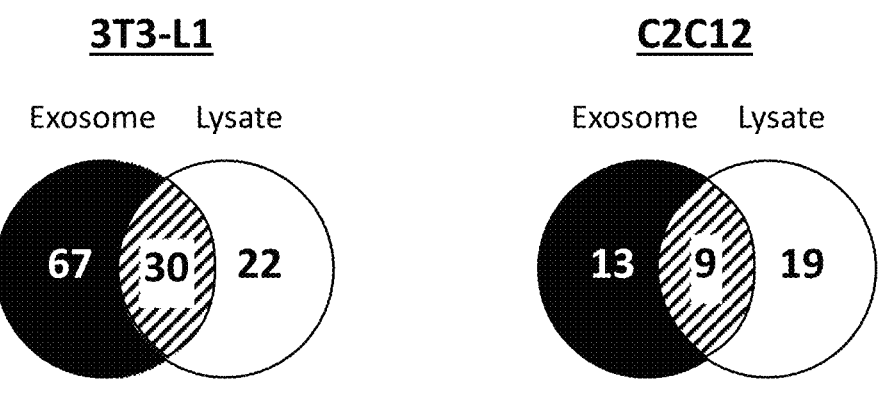
*Fig. 2A*
C2C12
Exosome    Lysate
*Fig. 2B*
SVEC
Exosome    Lysate
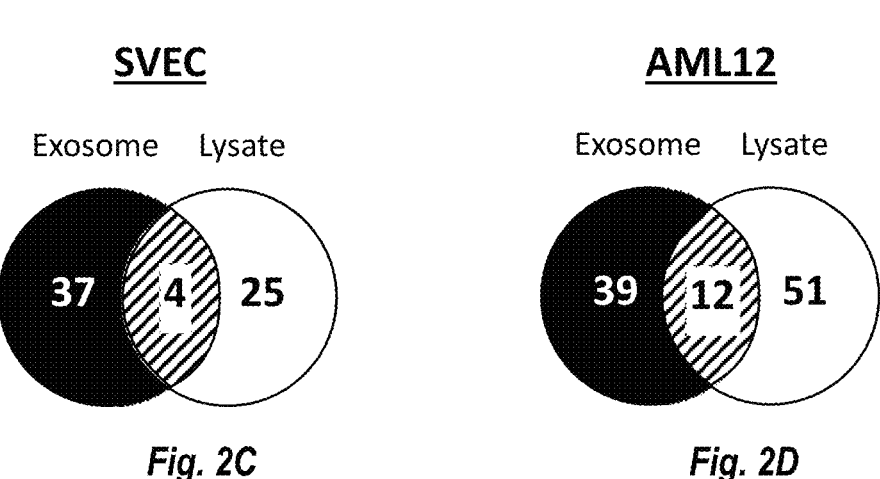
*Fig. 2C*
AML12
Exosome    Lysate
*Fig. 2D*
BAT
Exosome    Lysate
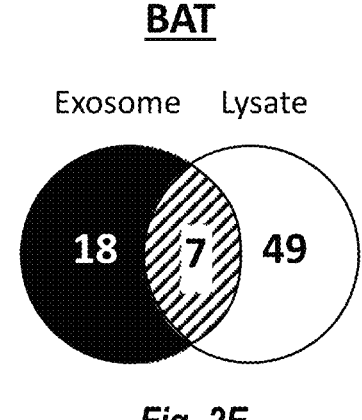
*Fig. 2E*

Exosome vs. Lysate miRNA Expression, FDR < 0.1

|  | UGUG | GGAG | CAUG | GGCa | aGGG | CUGG | TOTAL |
|---|---|---|---|---|---|---|---|
| BAT | 25 | 15 | 21 | 17 | 16 | 20 | 70 |
| C2C12 | 22 | 16 | 19 | 17 | 19 | 19 | 70 |
| 3T3-L1 | 19 | 13 | 17 | 14 | 15 | 22 | 62 |
| AML12 | 14 | 16 | 16 | 16 | 22 | 20 | 62 |
| SVEC | 13 | 21 | 8 | 18 | 26 | 26 | 70 |

Fig. 4A

| | CAGU | ACAG | AUUG | UAGC | CCCG | TOTAL |
|---|---|---|---|---|---|---|
| BAT | 23 | 18 | 15 | 10 | 9 | 56 |
| C2C12 | 24 | 19 | 18 | 11 | 7 | 34 |
| 3T3-L1 | 18 | 18 | 14 | 8 | 9 | 51 |
| AML12 | 24 | 18 | 15 | 10 | 7 | 48 |
| SVEC | 25 | 19 | 13 | 12 | 6 | 35 |

*Fig. 4B*

| BAT | | | | | |
|---|---|---|---|---|---|
| Exosome | | | Cell | | |
| 1 | UGUG | 48 | 1 | CAGU | 50 |
| 2 | CAUG | 40 | 2 | ACAG | 39 |
| 3 | CUGG | 37 | 3 | AUUG | 32 |
| 4 | GGCA/G | 32 | 4 | UAGC | 22 |
| 5 | A/CGGG | 31 | 5 | CCCG | 19 |
| 6 | GGAG | 28 | | | |
| | Total | 190 | | Total | 216 |

*Fig. 5A*

| C2C12 | | | | | |
|---|---|---|---|---|---|
| Exosome | | | Cell | | |
| 1 | UGUG | 36 | 1 | CAGU | 39 |
| 2 | CAUG | 31 | 2 | ACAG | 31 |
| 3 | CUGG | 31 | 3 | AUUG | 29 |
| 4 | A/CGGG | 31 | 4 | UAGC | 18 |
| 5 | GGCA/G | 28 | 5 | CCCG | 11 |
| 6 | GGAG | 26 | | | |
| | Total | 163 | | Total | 162 |

*Fig. 5B*

| 3T3-L1 | | | | | |
|---|---|---|---|---|---|
| Exosome | | | Cell | | |
| 1 | CUGG | 40 | 1 | CAGU | 33 |
| 2 | UGUG | 34 | 2 | ACAG | 33 |
| 3 | CAUG | 31 | 3 | AUUG | 26 |
| 4 | A/CGGG | 27 | 4 | CCCG | 17 |
| 5 | GGCA/G | 26 | 5 | UAGC | 15 |
| 6 | GGAG | 23 | | | |
| | Total | 183 | | Total | 186 |

*Fig. 5C*

| AML12 | | | | | |
|---|---|---|---|---|---|
| Exosome | | | Cell | | |
| 1 | A/CGGG | 30 | 1 | CAGU | 44 |
| 2 | CUGG | 27 | 2 | ACAG | 33 |
| 3 | GGAG | 24 | 3 | AUUG | 27 |
| 4 | GGCA/G | 21 | 4 | UAGC | 18 |
| 5 | CAUG | 21 | 5 | CCCG | 13 |
| 6 | UGUG | 19 | | | |
| | Total | 135 | | Total | 182 |

*Fig. 5D*

| SVEC | | | | | |
|---|---|---|---|---|---|
| Exosome | | | Cell | | |
| 1 | A/CGGG | 22 | 1 | CAGU | 31 |
| 2 | CUGG | 22 | 2 | ACAG | 23 |
| 3 | GGAG | 18 | 3 | AUUG | 16 |
| 4 | GGCA/G | 15 | 4 | UAGC | 15 |
| 5 | UGUG | 11 | 5 | CCCG | 7 |
| 6 | CAUG | 7 | | | |
| | Total | 85 | | Total | 123 |

*Fig. 5E*

Cell -> exo

| Name | Sequence (5'-3') | Motif |
|---|---|---|
| miR-34c-5p wt | AGGCAGUGUAGUUAGCUGAUUGC | Wild-type |
| miR-34c-5p - UGUG | AGGCAGUGUGUGUAGCUGAUUGC | UGUG |
| miR-34c-5p-CAUG | AGGCAGUGUAGUUAGCUCAUGGC | CAUG |
| miR-34c-5p-CGGGAG | AGGCAGUGUAGUUAGCGGGAGGC | CGGGAG |

Exo -> Cell

| Name | Sequence (5'-3') | Motif |
|---|---|---|
| miR-693-3p- wt | GCAGCUUUCAGAUGUGGCUGUAA | Wild-type |
| miR-693-3p - mut | GCAGCUUUCAGAU<u>C</u>UGGCUGUAA | U̶G̶U̶G̶ | miR-693-wt miR-693-mut

SEQUENCE LISTING

```
<160> NUMBER OF SEQ ID NOS: 704

<210> SEQ ID NO 1
<211> LENGTH: 22
<212> TYPE: RNA
<213> ORGANISM: Artificial Sequence
<220> FEATURE:
<223> OTHER INFORMATION: Synthetic: mmu-miR-615-5p

<400> SEQUENCE: 1 ggggguccccc ggugcucgga uc                                             22

<210> SEQ ID NO 2
<211> LENGTH: 22
<212> TYPE: RNA
<213> ORGANISM: Artificial Sequence
```

-continued

```
<220> FEATURE:
<223> OTHER INFORMATION: Synthetic: mmu-miR-686

<400> SEQUENCE: 2
auugcuuccc agacggugaa ga                                            22

<210> SEQ ID NO 3
<211> LENGTH: 22
<212> TYPE: RNA
<213> ORGANISM: Artificial Sequence
<220> FEATURE:
<223> OTHER INFORMATION: Synthetic: mmu-miR-770-3p

<400> SEQUENCE: 3
cgugggccug acguggagcu gg                                            22

<210> SEQ ID NO 4
<211> LENGTH: 20
<212> TYPE: RNA
<213> ORGANISM: Artificial Sequence
<220> FEATURE:
<223> OTHER INFORMATION: Synthetic: mmu-miR-1196

<400> SEQUENCE: 4
aaaucuaccu gccucugccu                                               20

<210> SEQ ID NO 5
<211> LENGTH: 23
<212> TYPE: RNA
<213> ORGANISM: Artificial Sequence
<220> FEATURE:
<223> OTHER INFORMATION: Synthetic: mmu-miR-671-5p

<400> SEQUENCE: 5
aggaagcccu ggaggggcug gag                                           23

<210> SEQ ID NO 6
<211> LENGTH: 23
<212> TYPE: RNA
<213> ORGANISM: Artificial Sequence
<220> FEATURE:
<223> OTHER INFORMATION: Synthetic: mmu-miR-693-3p

<400> SEQUENCE: 6
gcagcuuuca gauguggcug uaa                                           23

<210> SEQ ID NO 7
<211> LENGTH: 23
<212> TYPE: RNA
<213> ORGANISM: Artificial Sequence
<220> FEATURE:
<223> OTHER INFORMATION: Synthetic: mmu-miR-346

<400> SEQUENCE: 7
ugucugcccg agugccugcc ucu                                           23

<210> SEQ ID NO 8
<211> LENGTH: 22
<212> TYPE: RNA
<213> ORGANISM: Artificial Sequence
<220> FEATURE:
<223> OTHER INFORMATION: Synthetic: mmu-miR-1893

<400> SEQUENCE: 8
ggcgcgggcg cuggacgccu cg                                            22
```

```
<210> SEQ ID NO 9
<211> LENGTH: 20
<212> TYPE: RNA
<213> ORGANISM: Artificial Sequence
<220> FEATURE:
<223> OTHER INFORMATION: Synthetic: mmu-miR-124

<400> SEQUENCE: 9
uaaggcacgc ggugaaugcc                                                20

<210> SEQ ID NO 10
<211> LENGTH: 22
<212> TYPE: RNA
<213> ORGANISM: Artificial Sequence
<220> FEATURE:
<223> OTHER INFORMATION: Synthetic: mmu-miR-1907

<400> SEQUENCE: 10
gagcagcaga ggaucuggag gu                                             22

<210> SEQ ID NO 11
<211> LENGTH: 21
<212> TYPE: RNA
<213> ORGANISM: Artificial Sequence
<220> FEATURE:
<223> OTHER INFORMATION: Synthetic: mmu-miR-1306

<400> SEQUENCE: 11
acguuggcuc uggugguugau g                                             21

<210> SEQ ID NO 12
<211> LENGTH: 22
<212> TYPE: RNA
<213> ORGANISM: Artificial Sequence
<220> FEATURE:
<223> OTHER INFORMATION: Synthetic: mmu-miR-669c

<400> SEQUENCE: 12
auaguugugu guggaugugu gu                                             22

<210> SEQ ID NO 13
<211> LENGTH: 20
<212> TYPE: RNA
<213> ORGANISM: Artificial Sequence
<220> FEATURE:
<223> OTHER INFORMATION: Synthetic: mmu-miR-449b

<400> SEQUENCE: 13
aggcaguguu guuagcuggc                                                20

<210> SEQ ID NO 14
<211> LENGTH: 23
<212> TYPE: RNA
<213> ORGANISM: Artificial Sequence
<220> FEATURE:
<223> OTHER INFORMATION: Synthetic: mmu-miR-207

<400> SEQUENCE: 14
gcuucuccug gcucuccucc cuc                                            23

<210> SEQ ID NO 15
<211> LENGTH: 22
<212> TYPE: RNA
<213> ORGANISM: Artificial Sequence
<220> FEATURE:
<223> OTHER INFORMATION: Synthetic: mmu-miR-678
```

<400> SEQUENCE: 15
gucucggugc aaggacugga gg                                                22

<210> SEQ ID NO 16
<211> LENGTH: 20
<212> TYPE: RNA
<213> ORGANISM: Artificial Sequence
<220> FEATURE:
<223> OTHER INFORMATION: Synthetic: mmu-miR-665

<400> SEQUENCE: 16
accaggaggc ugaggucccu                                                   20

<210> SEQ ID NO 17
<211> LENGTH: 23
<212> TYPE: RNA
<213> ORGANISM: Artificial Sequence
<220> FEATURE:
<223> OTHER INFORMATION: Synthetic: mmu-miR-1943

<400> SEQUENCE: 17
aagggaggau cugggcaccu gga                                               23

<210> SEQ ID NO 18
<211> LENGTH: 22
<212> TYPE: RNA
<213> ORGANISM: Artificial Sequence
<220> FEATURE:
<223> OTHER INFORMATION: Synthetic: mmu-miR-150*

<400> SEQUENCE: 18
cugguacagg ccuggggggau ag                                               22

<210> SEQ ID NO 19
<211> LENGTH: 21
<212> TYPE: RNA
<213> ORGANISM: Artificial Sequence
<220> FEATURE:
<223> OTHER INFORMATION: Synthetic: mmu-miR-681

<400> SEQUENCE: 19
cagccucgcu ggcaggcagc u                                                 21

<210> SEQ ID NO 20
<211> LENGTH: 22
<212> TYPE: RNA
<213> ORGANISM: Artificial Sequence
<220> FEATURE:
<223> OTHER INFORMATION: Synthetic: mmu-miR-325

<400> SEQUENCE: 20
uuuauugagc accuccuauc aa                                                22

<210> SEQ ID NO 21
<211> LENGTH: 20
<212> TYPE: RNA
<213> ORGANISM: Artificial Sequence
<220> FEATURE:
<223> OTHER INFORMATION: Synthetic: mmu-miR-540-3p

<400> SEQUENCE: 21
aggucagagg ucgauccugg                                                   20

<210> SEQ ID NO 22

```
<211> LENGTH: 22
<212> TYPE: RNA
<213> ORGANISM: Artificial Sequence
<220> FEATURE:
<223> OTHER INFORMATION: Synthetic: mmu-miR-434-3p

<400> SEQUENCE: 22
uuugaaccau cacucgacuc cu                                              22

<210> SEQ ID NO 23
<211> LENGTH: 22
<212> TYPE: RNA
<213> ORGANISM: Artificial Sequence
<220> FEATURE:
<223> OTHER INFORMATION: Synthetic: mmu-let-7g*

<400> SEQUENCE: 23 acguacagg ccacugccuu gc                                               22

<210> SEQ ID NO 24
<211> LENGTH: 21
<212> TYPE: RNA
<213> ORGANISM: Artificial Sequence
<220> FEATURE:
<223> OTHER INFORMATION: Synthetic: mmu-miR-449c

<400> SEQUENCE: 24
aggcagugca uugcuagcug g                                               21

<210> SEQ ID NO 25
<211> LENGTH: 23
<212> TYPE: RNA
<213> ORGANISM: Artificial Sequence
<220> FEATURE:
<223> OTHER INFORMATION: Synthetic: mmu-miR-493

<400> SEQUENCE: 25
ugaagguccu acugugugcc agg                                             23

<210> SEQ ID NO 26
<211> LENGTH: 22
<212> TYPE: RNA
<213> ORGANISM: Artificial Sequence
<220> FEATURE:
<223> OTHER INFORMATION: Synthetic: mmu-miR-495

<400> SEQUENCE: 26
aaacaaacau ggugcacuuc uu                                              22

<210> SEQ ID NO 27
<211> LENGTH: 23
<212> TYPE: RNA
<213> ORGANISM: Artificial Sequence
<220> FEATURE:
<223> OTHER INFORMATION: Synthetic: mmu-miR-344

<400> SEQUENCE: 27
ugaucuagcc aaagccugac ugu                                             23

<210> SEQ ID NO 28
<211> LENGTH: 22
<212> TYPE: RNA
<213> ORGANISM: Artificial Sequence
<220> FEATURE:
<223> OTHER INFORMATION: Synthetic: mmu-miR-297a

<400> SEQUENCE: 28
```

-continued

```
auguaugugu gcaugugcau gu                                        22

<210> SEQ ID NO 29
<211> LENGTH: 23
<212> TYPE: RNA
<213> ORGANISM: Artificial Sequence
<220> FEATURE:
<223> OTHER INFORMATION: Synthetic: mmu-miR-466j

<400> SEQUENCE: 29
ugugugcaug ugcaugugug uaa                                       23

<210> SEQ ID NO 30
<211> LENGTH: 22
<212> TYPE: RNA
<213> ORGANISM: Artificial Sequence
<220> FEATURE:
<223> OTHER INFORMATION: Synthetic: mmu-miR-466f

<400> SEQUENCE: 30
acgugugugu gcaugugcau gu                                        22

<210> SEQ ID NO 31
<211> LENGTH: 23
<212> TYPE: RNA
<213> ORGANISM: Artificial Sequence
<220> FEATURE:
<223> OTHER INFORMATION: Synthetic: mmu-miR-574-5p

<400> SEQUENCE: 31
ugagugugug ugugugagug ugu                                       23

<210> SEQ ID NO 32
<211> LENGTH: 22
<212> TYPE: RNA
<213> ORGANISM: Artificial Sequence
<220> FEATURE:
<223> OTHER INFORMATION: Synthetic: mmu-miR-669l

<400> SEQUENCE: 32
aguugugugu gcauguauau gu                                        22

<210> SEQ ID NO 33
<211> LENGTH: 22
<212> TYPE: RNA
<213> ORGANISM: Artificial Sequence
<220> FEATURE:
<223> OTHER INFORMATION: Synthetic: mmu-miR-466h

<400> SEQUENCE: 33
ugugugcaug ugcuugugug ua                                        22

<210> SEQ ID NO 34
<211> LENGTH: 22
<212> TYPE: RNA
<213> ORGANISM: Artificial Sequence
<220> FEATURE:
<223> OTHER INFORMATION: Synthetic: mmu-miR-467h

<400> SEQUENCE: 34
auaagugugu gcauguauau gu                                        22

<210> SEQ ID NO 35
<211> LENGTH: 23
<212> TYPE: RNA
```

-continued

```
<213> ORGANISM: Artificial Sequence
<220> FEATURE:
<223> OTHER INFORMATION: Synthetic: mmu-miR-1187

<400> SEQUENCE: 35
uaugugugug uguaugugug uaa                                            23

<210> SEQ ID NO 36
<211> LENGTH: 22
<212> TYPE: RNA
<213> ORGANISM: Artificial Sequence
<220> FEATURE:
<223> OTHER INFORMATION: Synthetic: mmu-miR-466f-5p

<400> SEQUENCE: 36
uacgugugug ugcaugugca ug                                             22

<210> SEQ ID NO 37
<211> LENGTH: 19
<212> TYPE: RNA
<213> ORGANISM: Artificial Sequence
<220> FEATURE:
<223> OTHER INFORMATION: Synthetic: mmu-miR-764-5p

<400> SEQUENCE: 37
ggugcucaca uguccuccu                                                 19

<210> SEQ ID NO 38
<211> LENGTH: 21
<212> TYPE: RNA
<213> ORGANISM: Artificial Sequence
<220> FEATURE:
<223> OTHER INFORMATION: Synthetic: mmu-miR-326

<400> SEQUENCE: 38
ccucugggcc cuuccuccag u                                              21

<210> SEQ ID NO 39
<211> LENGTH: 20
<212> TYPE: RNA
<213> ORGANISM: Artificial Sequence
<220> FEATURE:
<223> OTHER INFORMATION: Synthetic: mmu-miR-324-3p

<400> SEQUENCE: 39
ccacugcccc aggugcugcu                                                20

<210> SEQ ID NO 40
<211> LENGTH: 22
<212> TYPE: RNA
<213> ORGANISM: Artificial Sequence
<220> FEATURE:
<223> OTHER INFORMATION: Synthetic: mmu-miR-211

<400> SEQUENCE: 40
uucccuuugu cauccuuugc cu                                             22

<210> SEQ ID NO 41
<211> LENGTH: 23
<212> TYPE: RNA
<213> ORGANISM: Artificial Sequence
<220> FEATURE:
<223> OTHER INFORMATION: Synthetic: mmu-miR-302d

<400> SEQUENCE: 41
uaagugcuuc cauguuugag ugu                                            23
```

-continued

```
<210> SEQ ID NO 42
<211> LENGTH: 22
<212> TYPE: RNA
<213> ORGANISM: Artificial Sequence
<220> FEATURE:
<223> OTHER INFORMATION: Synthetic: mmu-miR-674

<400> SEQUENCE: 42
gcacugagau gggaguggug ua                                          22

<210> SEQ ID NO 43
<211> LENGTH: 23
<212> TYPE: RNA
<213> ORGANISM: Artificial Sequence
<220> FEATURE:
<223> OTHER INFORMATION: Synthetic: mmu-miR-540-5p

<400> SEQUENCE: 43
caagggucac ccucugacuc ugu                                         23

<210> SEQ ID NO 44
<211> LENGTH: 21
<212> TYPE: RNA
<213> ORGANISM: Artificial Sequence
<220> FEATURE:
<223> OTHER INFORMATION: Synthetic: mmu-miR-431

<400> SEQUENCE: 44
ugucuugcag gccgucaugc a                                           21

<210> SEQ ID NO 45
<211> LENGTH: 22
<212> TYPE: RNA
<213> ORGANISM: Artificial Sequence
<220> FEATURE:
<223> OTHER INFORMATION: Synthetic: mmu-miR-345-3p

<400> SEQUENCE: 45
ccugaacuag gggucuggag ac                                          22

<210> SEQ ID NO 46
<211> LENGTH: 22
<212> TYPE: RNA
<213> ORGANISM: Artificial Sequence
<220> FEATURE:
<223> OTHER INFORMATION: Synthetic: mmu-miR-485*

<400> SEQUENCE: 46
agucauacac ggcucuccuc uc                                          22

<210> SEQ ID NO 47
<211> LENGTH: 20
<212> TYPE: RNA
<213> ORGANISM: Artificial Sequence
<220> FEATURE:
<223> OTHER INFORMATION: Synthetic: mmu-miR-669n

<400> SEQUENCE: 47
auuugugugu ggaugugugu                                             20

<210> SEQ ID NO 48
<211> LENGTH: 23
<212> TYPE: RNA
<213> ORGANISM: Artificial Sequence
<220> FEATURE:
```

-continued

<223> OTHER INFORMATION: Synthetic: mmu-miR-298

<400> SEQUENCE: 48
ggcagaggag ggcuguucuu ccc                                               23

<210> SEQ ID NO 49
<211> LENGTH: 23
<212> TYPE: RNA
<213> ORGANISM: Artificial Sequence
<220> FEATURE:
<223> OTHER INFORMATION: Synthetic: mmu-miR-1970

<400> SEQUENCE: 49
ugugucacug gggauaggcu uug                                               23

<210> SEQ ID NO 50
<211> LENGTH: 22
<212> TYPE: RNA
<213> ORGANISM: Artificial Sequence
<220> FEATURE:
<223> OTHER INFORMATION: Synthetic: mmu-miR-466c-5p

<400> SEQUENCE: 50
gaugugugug ugcauguaca ua                                                22

<210> SEQ ID NO 51
<211> LENGTH: 22
<212> TYPE: RNA
<213> ORGANISM: Artificial Sequence
<220> FEATURE:
<223> OTHER INFORMATION: Synthetic: mmu-miR-505

<400> SEQUENCE: 51
cgucaacacu ugcugguuuu cu                                                22

<210> SEQ ID NO 52
<211> LENGTH: 22
<212> TYPE: RNA
<213> ORGANISM: Artificial Sequence
<220> FEATURE:
<223> OTHER INFORMATION: Synthetic: mmu-miR-150

<400> SEQUENCE: 52
ucucccaacc cuuguaccag ug                                                22

<210> SEQ ID NO 53
<211> LENGTH: 23
<212> TYPE: RNA
<213> ORGANISM: Artificial Sequence
<220> FEATURE:
<223> OTHER INFORMATION: Synthetic: mmu-miR-466k

<400> SEQUENCE: 53
ugugugugua cauguacaug uga                                               23

<210> SEQ ID NO 54
<211> LENGTH: 22
<212> TYPE: RNA
<213> ORGANISM: Artificial Sequence
<220> FEATURE:
<223> OTHER INFORMATION: Synthetic: mmu-miR-302c

<400> SEQUENCE: 54
aagugcuucc auguuucagu gg                                                22

```
<210> SEQ ID NO 55
<211> LENGTH: 22
<212> TYPE: RNA
<213> ORGANISM: Artificial Sequence
<220> FEATURE:
<223> OTHER INFORMATION: Synthetic: mmu-miR-764-3p

<400> SEQUENCE: 55
aggaggccau aguggcaacu gu                                         22

<210> SEQ ID NO 56
<211> LENGTH: 22
<212> TYPE: RNA
<213> ORGANISM: Artificial Sequence
<220> FEATURE:
<223> OTHER INFORMATION: Synthetic: mmu-miR-1906

<400> SEQUENCE: 56
ugcagcagcc ugaggcaggg cu                                         22

<210> SEQ ID NO 57
<211> LENGTH: 22
<212> TYPE: RNA
<213> ORGANISM: Artificial Sequence
<220> FEATURE:
<223> OTHER INFORMATION: Synthetic: mmu-miR-1902

<400> SEQUENCE: 57
agaggugcag uaggcaugac uu                                         22

<210> SEQ ID NO 58
<211> LENGTH: 22
<212> TYPE: RNA
<213> ORGANISM: Artificial Sequence
<220> FEATURE:
<223> OTHER INFORMATION: Synthetic: mmu-miR-125b-3p

<400> SEQUENCE: 58
acggguuagg cucuugggag cu                                         22

<210> SEQ ID NO 59
<211> LENGTH: 23
<212> TYPE: RNA
<213> ORGANISM: Artificial Sequence
<220> FEATURE:
<223> OTHER INFORMATION: Synthetic: mmu-miR-468

<400> SEQUENCE: 59
uaugacugau gugcgugugu cug                                        23

<210> SEQ ID NO 60
<211> LENGTH: 22
<212> TYPE: RNA
<213> ORGANISM: Artificial Sequence
<220> FEATURE:
<223> OTHER INFORMATION: Synthetic: mmu-miR-381

<400> SEQUENCE: 60
uauacaaggg caagcucucu gu                                         22

<210> SEQ ID NO 61
<211> LENGTH: 22
<212> TYPE: RNA
<213> ORGANISM: Artificial Sequence
<220> FEATURE:
<223> OTHER INFORMATION: Synthetic: mmu-miR-490
```

<400> SEQUENCE: 61
caaccuggag gacuccaugc ug                                    22

<210> SEQ ID NO 62
<211> LENGTH: 24
<212> TYPE: RNA
<213> ORGANISM: Artificial Sequence
<220> FEATURE:
<223> OTHER INFORMATION: Synthetic: mmu-miR-290-3p

<400> SEQUENCE: 62
aaagugccgc cuaguuuuaa gccc                                  24

<210> SEQ ID NO 63
<211> LENGTH: 23
<212> TYPE: RNA
<213> ORGANISM: Artificial Sequence
<220> FEATURE:
<223> OTHER INFORMATION: Synthetic: mmu-miR-489

<400> SEQUENCE: 63
aaugacacca cauauauggc agc                                   23

<210> SEQ ID NO 64
<211> LENGTH: 22
<212> TYPE: RNA
<213> ORGANISM: Artificial Sequence
<220> FEATURE:
<223> OTHER INFORMATION: Synthetic: mmu-miR-487b

<400> SEQUENCE: 64
aaucguacag ggucauccac uu                                    22

<210> SEQ ID NO 65
<211> LENGTH: 22
<212> TYPE: RNA
<213> ORGANISM: Artificial Sequence
<220> FEATURE:
<223> OTHER INFORMATION: Synthetic: mmu-miR-297c

<400> SEQUENCE: 65
auguaugugu gcauguacau gu                                    22

<210> SEQ ID NO 66
<211> LENGTH: 26
<212> TYPE: RNA
<213> ORGANISM: Artificial Sequence
<220> FEATURE:
<223> OTHER INFORMATION: Synthetic: mmu-miR-469

<400> SEQUENCE: 66
ugccucuuuc auugaucuug gugucc                                26

<210> SEQ ID NO 67
<211> LENGTH: 22
<212> TYPE: RNA
<213> ORGANISM: Artificial Sequence
<220> FEATURE:
<223> OTHER INFORMATION: Synthetic: mmu-miR-141

<400> SEQUENCE: 67
uaacacuguc ugguaaagau gg                                    22

<210> SEQ ID NO 68
<211> LENGTH: 24

```
<212> TYPE: RNA
<213> ORGANISM: Artificial Sequence
<220> FEATURE:
<223> OTHER INFORMATION: Synthetic: mmu-miR-1941-5p

<400> SEQUENCE: 68
agggagaugc ugguacagag gcuu                                          24

<210> SEQ ID NO 69
<211> LENGTH: 22
<212> TYPE: RNA
<213> ORGANISM: Artificial Sequence
<220> FEATURE:
<223> OTHER INFORMATION: Synthetic: mmu-miR-380-3p

<400> SEQUENCE: 69
uauguaguau gguccacauc uu                                            22

<210> SEQ ID NO 70
<211> LENGTH: 22
<212> TYPE: RNA
<213> ORGANISM: Artificial Sequence
<220> FEATURE:
<223> OTHER INFORMATION: Synthetic: mmu-miR-291b-3p

<400> SEQUENCE: 70
aaagugcauc cauuuuguuu gu                                            22

<210> SEQ ID NO 71
<211> LENGTH: 22
<212> TYPE: RNA
<213> ORGANISM: Artificial Sequence
<220> FEATURE:
<223> OTHER INFORMATION: Synthetic: mmu-miR-471

<400> SEQUENCE: 71
uacguaguau agugcuuuuc ac                                            22

<210> SEQ ID NO 72
<211> LENGTH: 21
<212> TYPE: RNA
<213> ORGANISM: Artificial Sequence
<220> FEATURE:
<223> OTHER INFORMATION: Synthetic: mmu-miR-337-3p

<400> SEQUENCE: 72
uucagcuccu auaugaugcc u                                             21

<210> SEQ ID NO 73
<211> LENGTH: 22
<212> TYPE: RNA
<213> ORGANISM: Artificial Sequence
<220> FEATURE:
<223> OTHER INFORMATION: Synthetic: mmu-miR-335-3p

<400> SEQUENCE: 73
uuuuucauua uugcuccuga cc                                            22

<210> SEQ ID NO 74
<211> LENGTH: 21
<212> TYPE: RNA
<213> ORGANISM: Artificial Sequence
<220> FEATURE:
<223> OTHER INFORMATION: Synthetic: mmu-miR-376c

<400> SEQUENCE: 74
```
aacauagagg aaauuucacg u                                                                         21

<210> SEQ ID NO 75
<211> LENGTH: 22
<212> TYPE: RNA
<213> ORGANISM: Artificial Sequence
<220> FEATURE:
<223> OTHER INFORMATION: Synthetic: mmu-miR-29c*

<400> SEQUENCE: 75
ugaccgauuu cuccuggugu uc                                                                         22

<210> SEQ ID NO 76
<211> LENGTH: 22
<212> TYPE: RNA
<213> ORGANISM: Artificial Sequence
<220> FEATURE:
<223> OTHER INFORMATION: Synthetic: mmu-miR-761

<400> SEQUENCE: 76
gcagcagggu gaaacugaca ca                                                                         22

<210> SEQ ID NO 77
<211> LENGTH: 21
<212> TYPE: RNA
<213> ORGANISM: Artificial Sequence
<220> FEATURE:
<223> OTHER INFORMATION: Synthetic: mmu-miR-707

<400> SEQUENCE: 77
cagucaugcc gcuugccuac g                                                                          21

<210> SEQ ID NO 78
<211> LENGTH: 22
<212> TYPE: RNA
<213> ORGANISM: Artificial Sequence
<220> FEATURE:
<223> OTHER INFORMATION: Synthetic: mmu-miR-340-5p

<400> SEQUENCE: 78
uuauaaagca augagacuga uu                                                                         22

<210> SEQ ID NO 79
<211> LENGTH: 22
<212> TYPE: RNA
<213> ORGANISM: Artificial Sequence
<220> FEATURE:
<223> OTHER INFORMATION: Synthetic: mmu-miR-377

<400> SEQUENCE: 79
aucacacaaa ggcaacuuuu gu                                                                         22

<210> SEQ ID NO 80
<211> LENGTH: 19
<212> TYPE: RNA
<213> ORGANISM: Artificial Sequence
<220> FEATURE:
<223> OTHER INFORMATION: Synthetic: mmu-miR-713

<400> SEQUENCE: 80
ugcacugaag gcacacagc                                                                             19

<210> SEQ ID NO 81
<211> LENGTH: 21
<212> TYPE: RNA
<213> ORGANISM: Artificial Sequence -continued

```
<220> FEATURE:
<223> OTHER INFORMATION: Synthetic: mmu-miR-410

<400> SEQUENCE: 81
aauauaacac agauggccug u                                          21

<210> SEQ ID NO 82
<211> LENGTH: 22
<212> TYPE: RNA
<213> ORGANISM: Artificial Sequence
<220> FEATURE:
<223> OTHER INFORMATION: Synthetic: mmu-miR-297b-5p

<400> SEQUENCE: 82
auguaugugu gcaugaacau gu                                         22

<210> SEQ ID NO 83
<211> LENGTH: 21
<212> TYPE: RNA
<213> ORGANISM: Artificial Sequence
<220> FEATURE:
<223> OTHER INFORMATION: Synthetic: mmu-miR-483*

<400> SEQUENCE: 83
ucacuccucc ccucccgucu u                                          21

<210> SEQ ID NO 84
<211> LENGTH: 22
<212> TYPE: RNA
<213> ORGANISM: Artificial Sequence
<220> FEATURE:
<223> OTHER INFORMATION: Synthetic: mmu-miR-590-5p

<400> SEQUENCE: 84
gagcuuauuc auaaaagugc ag                                         22

<210> SEQ ID NO 85
<211> LENGTH: 22
<212> TYPE: RNA
<213> ORGANISM: Artificial Sequence
<220> FEATURE:
<223> OTHER INFORMATION: Synthetic: mmu-miR-187

<400> SEQUENCE: 85
ucgugucuug uguugcagcc gg                                         22

<210> SEQ ID NO 86
<211> LENGTH: 22
<212> TYPE: RNA
<213> ORGANISM: Artificial Sequence
<220> FEATURE:
<223> OTHER INFORMATION: Synthetic: mmu-miR-503*

<400> SEQUENCE: 86
gaguauuguu uccacugccu gg                                         22

<210> SEQ ID NO 87
<211> LENGTH: 22
<212> TYPE: RNA
<213> ORGANISM: Artificial Sequence
<220> FEATURE:
<223> OTHER INFORMATION: Synthetic: mmu-miR-500

<400> SEQUENCE: 87
aaugcaccug ggcaaggguu ca                                         22
```

-continued

<210> SEQ ID NO 88
<211> LENGTH: 22
<212> TYPE: RNA
<213> ORGANISM: Artificial Sequence
<220> FEATURE:
<223> OTHER INFORMATION: Synthetic: mmu-miR-433

<400> SEQUENCE: 88
aucaugaugg gcuccucggu gu                                          22

<210> SEQ ID NO 89
<211> LENGTH: 21
<212> TYPE: RNA
<213> ORGANISM: Artificial Sequence
<220> FEATURE:
<223> OTHER INFORMATION: Synthetic: mmu-miR-337-5p

<400> SEQUENCE: 89
gaacggcguc augcaggagu u                                           21

<210> SEQ ID NO 90
<211> LENGTH: 22
<212> TYPE: RNA
<213> ORGANISM: Artificial Sequence
<220> FEATURE:
<223> OTHER INFORMATION: Synthetic: mmu-miR-486

<400> SEQUENCE: 90
uccuguacug agcugccccg ag                                          22

<210> SEQ ID NO 91
<211> LENGTH: 22
<212> TYPE: RNA
<213> ORGANISM: Artificial Sequence
<220> FEATURE:
<223> OTHER INFORMATION: Synthetic: mmu-miR-712*

<400> SEQUENCE: 91
ugcgagucac ccccgggugu ug                                          22

<210> SEQ ID NO 92
<211> LENGTH: 21
<212> TYPE: RNA
<213> ORGANISM: Artificial Sequence
<220> FEATURE:
<223> OTHER INFORMATION: Synthetic: mmu-miR-341

<400> SEQUENCE: 92
ucggucgauc ggucggucgg u                                           21

<210> SEQ ID NO 93
<211> LENGTH: 22
<212> TYPE: RNA
<213> ORGANISM: Artificial Sequence
<220> FEATURE:
<223> OTHER INFORMATION: Synthetic: mmu-miR-542-5p

<400> SEQUENCE: 93
cucggggauc aucaugucac ga                                          22

<210> SEQ ID NO 94
<211> LENGTH: 23
<212> TYPE: RNA
<213> ORGANISM: Artificial Sequence
<220> FEATURE:
<223> OTHER INFORMATION: Synthetic: mmu-miR-137

-continued

<400> SEQUENCE: 94
uuauugcuua agaauacgcg uag                                          23

<210> SEQ ID NO 95
<211> LENGTH: 22
<212> TYPE: RNA
<213> ORGANISM: Artificial Sequence
<220> FEATURE:
<223> OTHER INFORMATION: Synthetic: mmu-miR-1945

<400> SEQUENCE: 95
ucuucgcggg uacugucggg ac                                           22

<210> SEQ ID NO 96
<211> LENGTH: 21
<212> TYPE: RNA
<213> ORGANISM: Artificial Sequence
<220> FEATURE:
<223> OTHER INFORMATION: Synthetic: mmu-miR-142-5p

<400> SEQUENCE: 96
cauaaaguag aaagcacuac u                                            21

<210> SEQ ID NO 97
<211> LENGTH: 22
<212> TYPE: RNA
<213> ORGANISM: Artificial Sequence
<220> FEATURE:
<223> OTHER INFORMATION: Synthetic: mmu-miR-218-2*

<400> SEQUENCE: 97
caugguucug ucaagcaccg cg                                           22

<210> SEQ ID NO 98
<211> LENGTH: 23
<212> TYPE: RNA
<213> ORGANISM: Artificial Sequence
<220> FEATURE:
<223> OTHER INFORMATION: Synthetic: mmu-miR-105

<400> SEQUENCE: 98
ccaagugcuc agaugcuugu ggu                                          23

<210> SEQ ID NO 99
<211> LENGTH: 27
<212> TYPE: RNA
<213> ORGANISM: Artificial Sequence
<220> FEATURE:
<223> OTHER INFORMATION: Synthetic: mmu-miR-1940

<400> SEQUENCE: 99
auggaggacu gagaaggugg agcaguu                                      27

<210> SEQ ID NO 100
<211> LENGTH: 22
<212> TYPE: RNA
<213> ORGANISM: Artificial Sequence
<220> FEATURE:
<223> OTHER INFORMATION: Synthetic: mmu-miR-299

<400> SEQUENCE: 100 uauguggggac gguaaaccgc uu                                          22

<210> SEQ ID NO 101

-continued

```
<211> LENGTH: 22
<212> TYPE: RNA
<213> ORGANISM: Artificial Sequence
<220> FEATURE:
<223> OTHER INFORMATION: Synthetic: mmu-miR-1898

<400> SEQUENCE: 101
aggucaaggu ucacagggga uc                                          22

<210> SEQ ID NO 102
<211> LENGTH: 24
<212> TYPE: RNA
<213> ORGANISM: Artificial Sequence
<220> FEATURE:
<223> OTHER INFORMATION: Synthetic: mmu-miR-1968

<400> SEQUENCE: 102
ugcagcuguu aaggauggug gacu                                        24

<210> SEQ ID NO 103
<211> LENGTH: 22
<212> TYPE: RNA
<213> ORGANISM: Artificial Sequence
<220> FEATURE:
<223> OTHER INFORMATION: Synthetic: mmu-miR-208a

<400> SEQUENCE: 103
auaagacgag caaaaagcuu gu                                          22

<210> SEQ ID NO 104
<211> LENGTH: 19
<212> TYPE: RNA
<213> ORGANISM: Artificial Sequence
<220> FEATURE:
<223> OTHER INFORMATION: Synthetic: mmu-miR-1957

<400> SEQUENCE: 104
cagugguaga gcauaugac                                              19

<210> SEQ ID NO 105
<211> LENGTH: 22
<212> TYPE: RNA
<213> ORGANISM: Artificial Sequence
<220> FEATURE:
<223> OTHER INFORMATION: Synthetic: mmu-miR-509-5p

<400> SEQUENCE: 105
uacuccagaa uguggcaauc au                                          22

<210> SEQ ID NO 106
<211> LENGTH: 22
<212> TYPE: RNA
<213> ORGANISM: Artificial Sequence
<220> FEATURE:
<223> OTHER INFORMATION: Synthetic: mmu-miR-467d

<400> SEQUENCE: 106
uaagugcgcg cauguauaug cg                                          22

<210> SEQ ID NO 107
<211> LENGTH: 22
<212> TYPE: RNA
<213> ORGANISM: Artificial Sequence
<220> FEATURE:
<223> OTHER INFORMATION: Synthetic: mmu-miR-466e-5p

<400> SEQUENCE: 107
```
gaugugugug uacauguaca ua                                          22

<210> SEQ ID NO 108
<211> LENGTH: 23
<212> TYPE: RNA
<213> ORGANISM: Artificial Sequence
<220> FEATURE:
<223> OTHER INFORMATION: Synthetic: mmu-miR-503

<400> SEQUENCE: 108
uagcagcggg aacaguacug cag                                         23

<210> SEQ ID NO 109
<211> LENGTH: 18
<212> TYPE: RNA
<213> ORGANISM: Artificial Sequence
<220> FEATURE:
<223> OTHER INFORMATION: Synthetic: mmu-miR-1971

<400> SEQUENCE: 109
guaaaggcug ggcugaga                                               18

<210> SEQ ID NO 110
<211> LENGTH: 20
<212> TYPE: RNA
<213> ORGANISM: Artificial Sequence
<220> FEATURE:
<223> OTHER INFORMATION: Synthetic: mmu-miR-412

<400> SEQUENCE: 110
uucaccuggu ccacuagccg                                             20

<210> SEQ ID NO 111
<211> LENGTH: 22
<212> TYPE: RNA
<213> ORGANISM: Artificial Sequence
<220> FEATURE:
<223> OTHER INFORMATION: Synthetic: mmu-miR-204

<400> SEQUENCE: 111
uucccuuugu cauccuaugc cu                                          22

<210> SEQ ID NO 112
<211> LENGTH: 22
<212> TYPE: RNA
<213> ORGANISM: Artificial Sequence
<220> FEATURE:
<223> OTHER INFORMATION: Synthetic: mmu-miR-338-3p

<400> SEQUENCE: 112
uccagcauca gugauuuugu ug                                          22

<210> SEQ ID NO 113
<211> LENGTH: 22
<212> TYPE: RNA
<213> ORGANISM: Artificial Sequence
<220> FEATURE:
<223> OTHER INFORMATION: Synthetic: mmu-miR-201

<400> SEQUENCE: 113
uacucaguaa ggcauuguuc uu                                          22

<210> SEQ ID NO 114
<211> LENGTH: 22
<212> TYPE: RNA

<213> ORGANISM: Artificial Sequence
<220> FEATURE:
<223> OTHER INFORMATION: Synthetic: mmu-miR-384-3p

<400> SEQUENCE: 114
auuccuagaa auuguucaca au                                                  22

<210> SEQ ID NO 115
<211> LENGTH: 22
<212> TYPE: RNA
<213> ORGANISM: Artificial Sequence
<220> FEATURE:
<223> OTHER INFORMATION: Synthetic: mmu-miR-125a-3p

<400> SEQUENCE: 115
acaggugagg uucuugggag cc                                                  22

<210> SEQ ID NO 116
<211> LENGTH: 23
<212> TYPE: RNA
<213> ORGANISM: Artificial Sequence
<220> FEATURE:
<223> OTHER INFORMATION: Synthetic: mmu-miR-466c-3p

<400> SEQUENCE: 116
uauacauaca cgcacacaua aga                                                 23

<210> SEQ ID NO 117
<211> LENGTH: 23
<212> TYPE: RNA
<213> ORGANISM: Artificial Sequence
<220> FEATURE:
<223> OTHER INFORMATION: Synthetic: mmu-miR-217

<400> SEQUENCE: 117
uacugcauca ggaacugacu gga                                                 23

<210> SEQ ID NO 118
<211> LENGTH: 21
<212> TYPE: RNA
<213> ORGANISM: Artificial Sequence
<220> FEATURE:
<223> OTHER INFORMATION: Synthetic: mmu-miR-376a

<400> SEQUENCE: 118
aucguagagg aaaauccacg u                                                   21

<210> SEQ ID NO 119
<211> LENGTH: 22
<212> TYPE: RNA
<213> ORGANISM: Artificial Sequence
<220> FEATURE:
<223> OTHER INFORMATION: Synthetic: mmu-miR-367

<400> SEQUENCE: 119
aauugcacuu uagcaauggu ga                                                  22

<210> SEQ ID NO 120
<211> LENGTH: 22
<212> TYPE: RNA
<213> ORGANISM: Artificial Sequence
<220> FEATURE:
<223> OTHER INFORMATION: Synthetic: mmu-miR-342-5p

<400> SEQUENCE: 120
aggggugcua ucugugauug ag                                                  22

-continued

```
<210> SEQ ID NO 121
<211> LENGTH: 22
<212> TYPE: RNA
<213> ORGANISM: Artificial Sequence
<220> FEATURE:
<223> OTHER INFORMATION: Synthetic: mmu-miR-136

<400> SEQUENCE: 121
acuccauuug uuugaugau gg                                          22

<210> SEQ ID NO 122
<211> LENGTH: 23
<212> TYPE: RNA
<213> ORGANISM: Artificial Sequence
<220> FEATURE:
<223> OTHER INFORMATION: Synthetic: mmu-miR-18b

<400> SEQUENCE: 122
uaaggugcau cuagugcugu uag                                        23

<210> SEQ ID NO 123
<211> LENGTH: 22
<212> TYPE: RNA
<213> ORGANISM: Artificial Sequence
<220> FEATURE:
<223> OTHER INFORMATION: Synthetic: mmu-miR-742

<400> SEQUENCE: 123
gaaagccacc augcugggua aa                                         22

<210> SEQ ID NO 124
<211> LENGTH: 21
<212> TYPE: RNA
<213> ORGANISM: Artificial Sequence
<220> FEATURE:
<223> OTHER INFORMATION: Synthetic: mmu-miR-652

<400> SEQUENCE: 124
aauggcgcca cuaggguugu g                                          21

<210> SEQ ID NO 125
<211> LENGTH: 19
<212> TYPE: RNA
<213> ORGANISM: Artificial Sequence
<220> FEATURE:
<223> OTHER INFORMATION: Synthetic: mmu-miR-758

<400> SEQUENCE: 125
uuugugaccu gguccacua                                             19

<210> SEQ ID NO 126
<211> LENGTH: 23
<212> TYPE: RNA
<213> ORGANISM: Artificial Sequence
<220> FEATURE:
<223> OTHER INFORMATION: Synthetic: mmu-miR-325*

<400> SEQUENCE: 126
ccuaguaggu gcucaguaag ugu                                        23

<210> SEQ ID NO 127
<211> LENGTH: 22
<212> TYPE: RNA
<213> ORGANISM: Artificial Sequence
<220> FEATURE:
```

-continued

<223> OTHER INFORMATION: Synthetic: mmu-miR-708*

<400> SEQUENCE: 127
caacuagacu gugagcuucu ag                                           22

<210> SEQ ID NO 128
<211> LENGTH: 22
<212> TYPE: RNA
<213> ORGANISM: Artificial Sequence
<220> FEATURE:
<223> OTHER INFORMATION: Synthetic: mmu-miR-30c-1*

<400> SEQUENCE: 128
cugggagagg guuguuuacu cc                                           22

<210> SEQ ID NO 129
<211> LENGTH: 20
<212> TYPE: RNA
<213> ORGANISM: Artificial Sequence
<220> FEATURE:
<223> OTHER INFORMATION: Synthetic: mmu-miR-144

<400> SEQUENCE: 129
uacaguauag augauguacu                                             20

<210> SEQ ID NO 130
<211> LENGTH: 22
<212> TYPE: RNA
<213> ORGANISM: Artificial Sequence
<220> FEATURE:
<223> OTHER INFORMATION: Synthetic: mmu-miR-1938

<400> SEQUENCE: 130
cggugggacu uguaguucgg uc                                           22

<210> SEQ ID NO 131
<211> LENGTH: 22
<212> TYPE: RNA
<213> ORGANISM: Artificial Sequence
<220> FEATURE:
<223> OTHER INFORMATION: Synthetic: mmu-miR-1951

<400> SEQUENCE: 131
guaguggaga cuggguguggc ua                                          22

<210> SEQ ID NO 132
<211> LENGTH: 22
<212> TYPE: RNA
<213> ORGANISM: Artificial Sequence
<220> FEATURE:
<223> OTHER INFORMATION: Synthetic: mmu-miR-294*

<400> SEQUENCE: 132
acucaaaaug gaggcccuau cu                                           22

<210> SEQ ID NO 133
<211> LENGTH: 22
<212> TYPE: RNA
<213> ORGANISM: Artificial Sequence
<220> FEATURE:
<223> OTHER INFORMATION: Synthetic: mmu-miR-882

<400> SEQUENCE: 133
aggagagagu uagcgcauua gu                                           22

-continued

```
<210> SEQ ID NO 134
<211> LENGTH: 22
<212> TYPE: RNA
<213> ORGANISM: Artificial Sequence
<220> FEATURE:
<223> OTHER INFORMATION: Synthetic: mmu-miR-582-3p

<400> SEQUENCE: 134
ccuguugaac aacugaaccc aa                                                22

<210> SEQ ID NO 135
<211> LENGTH: 23
<212> TYPE: RNA
<213> ORGANISM: Artificial Sequence
<220> FEATURE:
<223> OTHER INFORMATION: Synthetic: mmu-miR-465a-5p

<400> SEQUENCE: 135
uauuuagaau ggcacugaug uga                                               23

<210> SEQ ID NO 136
<211> LENGTH: 22
<212> TYPE: RNA
<213> ORGANISM: Artificial Sequence
<220> FEATURE:
<223> OTHER INFORMATION: Synthetic: mmu-miR-543

<400> SEQUENCE: 136
aaacauucgc ggugcacuuc uu                                                22

<210> SEQ ID NO 137
<211> LENGTH: 22
<212> TYPE: RNA
<213> ORGANISM: Artificial Sequence
<220> FEATURE:
<223> OTHER INFORMATION: Synthetic: mmu-miR-30b*

<400> SEQUENCE: 137
cugggaugug gauguuuacg uc                                                22

<210> SEQ ID NO 138
<211> LENGTH: 22
<212> TYPE: RNA
<213> ORGANISM: Artificial Sequence
<220> FEATURE:
<223> OTHER INFORMATION: Synthetic: mmu-miR-449a

<400> SEQUENCE: 138
uggcagugua uuguuagcug gu                                                22

<210> SEQ ID NO 139
<211> LENGTH: 22
<212> TYPE: RNA
<213> ORGANISM: Artificial Sequence
<220> FEATURE:
<223> OTHER INFORMATION: Synthetic: mmu-miR-1903

<400> SEQUENCE: 139
ccuucuucuu cuuccugaga ca                                                22

<210> SEQ ID NO 140
<211> LENGTH: 22
<212> TYPE: RNA
<213> ORGANISM: Artificial Sequence
<220> FEATURE:
<223> OTHER INFORMATION: Synthetic: mmu-miR-429
```

<400> SEQUENCE: 140
uaauacuguc ugguaaugcc gu                                                    22

<210> SEQ ID NO 141
<211> LENGTH: 23
<212> TYPE: RNA
<213> ORGANISM: Artificial Sequence
<220> FEATURE:
<223> OTHER INFORMATION: Synthetic: mmu-miR-295

<400> SEQUENCE: 141
aaagugcuac uacuuuugag ucu                                                   23

<210> SEQ ID NO 142
<211> LENGTH: 22
<212> TYPE: RNA
<213> ORGANISM: Artificial Sequence
<220> FEATURE:
<223> OTHER INFORMATION: Synthetic: mmu-miR-451

<400> SEQUENCE: 142
aaaccguuac cauuacugag uu                                                    22

<210> SEQ ID NO 143
<211> LENGTH: 22
<212> TYPE: RNA
<213> ORGANISM: Artificial Sequence
<220> FEATURE:
<223> OTHER INFORMATION: Synthetic: mmu-miR-876-5p

<400> SEQUENCE: 143
uggauuucuc ugugaaucac ua                                                    22

<210> SEQ ID NO 144
<211> LENGTH: 20
<212> TYPE: RNA
<213> ORGANISM: Artificial Sequence
<220> FEATURE:
<223> OTHER INFORMATION: Synthetic: mmu-miR-1199

<400> SEQUENCE: 144
ucugaguccc ggucgcgcgg                                                       20

<210> SEQ ID NO 145
<211> LENGTH: 23
<212> TYPE: RNA
<213> ORGANISM: Artificial Sequence
<220> FEATURE:
<223> OTHER INFORMATION: Synthetic: mmu-miR-1927

<400> SEQUENCE: 145
gaccucugga uguuagggac uga                                                   23

<210> SEQ ID NO 146
<211> LENGTH: 22
<212> TYPE: RNA
<213> ORGANISM: Artificial Sequence
<220> FEATURE:
<223> OTHER INFORMATION: Synthetic: mmu-miR-411*

<400> SEQUENCE: 146
uauguaacac gguccacuaa cc                                                    22

<210> SEQ ID NO 147
<211> LENGTH: 22

-continued

```
<212> TYPE: RNA
<213> ORGANISM: Artificial Sequence
<220> FEATURE:
<223> OTHER INFORMATION: Synthetic: mmu-miR-200b*

<400> SEQUENCE: 147
caucuuacug ggcagcauug ga                                          22

<210> SEQ ID NO 148
<211> LENGTH: 22
<212> TYPE: RNA
<213> ORGANISM: Artificial Sequence
<220> FEATURE:
<223> OTHER INFORMATION: Synthetic: mmu-miR-382

<400> SEQUENCE: 148
gaaguuguuc gugguggauu cg                                          22

<210> SEQ ID NO 149
<211> LENGTH: 23
<212> TYPE: RNA
<213> ORGANISM: Artificial Sequence
<220> FEATURE:
<223> OTHER INFORMATION: Synthetic: mmu-miR-20b

<400> SEQUENCE: 149
caaagugcuc auagugcagg uag                                         23

<210> SEQ ID NO 150
<211> LENGTH: 22
<212> TYPE: RNA
<213> ORGANISM: Artificial Sequence
<220> FEATURE:
<223> OTHER INFORMATION: Synthetic: mmu-miR-200a*

<400> SEQUENCE: 150
caucuuaccg gacagugcug ga                                          22

<210> SEQ ID NO 151
<211> LENGTH: 22
<212> TYPE: RNA
<213> ORGANISM: Artificial Sequence
<220> FEATURE:
<223> OTHER INFORMATION: Synthetic: mmu-miR-434-5p

<400> SEQUENCE: 151
gcucgacuca ugguuugaac ca                                          22

<210> SEQ ID NO 152
<211> LENGTH: 22
<212> TYPE: RNA
<213> ORGANISM: Artificial Sequence
<220> FEATURE:
<223> OTHER INFORMATION: Synthetic: mmu-miR-874

<400> SEQUENCE: 152
cugcccuggc ccgagggacc ga                                          22

<210> SEQ ID NO 153
<211> LENGTH: 22
<212> TYPE: RNA
<213> ORGANISM: Artificial Sequence
<220> FEATURE:
<223> OTHER INFORMATION: Synthetic: mmu-miR-147

<400> SEQUENCE: 153
```

-continued

```
gugugcggaa augcuucugc ua                                        22

<210> SEQ ID NO 154
<211> LENGTH: 23
<212> TYPE: RNA
<213> ORGANISM: Artificial Sequence
<220> FEATURE:
<223> OTHER INFORMATION: Synthetic: mmu-miR-432

<400> SEQUENCE: 154
ucuuggagua gaucagugggg cag                                      23

<210> SEQ ID NO 155
<211> LENGTH: 22
<212> TYPE: RNA
<213> ORGANISM: Artificial Sequence
<220> FEATURE:
<223> OTHER INFORMATION: Synthetic: mmu-miR-302c*

<400> SEQUENCE: 155
gcuuuaacau gggguuaccu gc                                        22

<210> SEQ ID NO 156
<211> LENGTH: 21
<212> TYPE: RNA
<213> ORGANISM: Artificial Sequence
<220> FEATURE:
<223> OTHER INFORMATION: Synthetic: mmu-miR-188-5p

<400> SEQUENCE: 156
caucccuugc augguggagg g                                         21

<210> SEQ ID NO 157
<211> LENGTH: 22
<212> TYPE: RNA
<213> ORGANISM: Artificial Sequence
<220> FEATURE:
<223> OTHER INFORMATION: Synthetic: mmu-miR-7a*

<400> SEQUENCE: 157
caacaaauca cagucugcca ua                                        22

<210> SEQ ID NO 158
<211> LENGTH: 22
<212> TYPE: RNA
<213> ORGANISM: Artificial Sequence
<220> FEATURE:
<223> OTHER INFORMATION: Synthetic: mmu-miR-17*

<400> SEQUENCE: 158
acugcaguga gggcacuugu ag                                        22

<210> SEQ ID NO 159
<211> LENGTH: 22
<212> TYPE: RNA
<213> ORGANISM: Artificial Sequence
<220> FEATURE:
<223> OTHER INFORMATION: Synthetic: mmu-miR-687

<400> SEQUENCE: 159
cuauccugga augcagcaau ga                                        22

<210> SEQ ID NO 160
<211> LENGTH: 23
<212> TYPE: RNA
<213> ORGANISM: Artificial Sequence
```

-continued

<220> FEATURE:
<223> OTHER INFORMATION: Synthetic: mmu-miR-302b*

<400> SEQUENCE: 160
acuuuaacau gggaaugcuu ucu                                                    23

<210> SEQ ID NO 161
<211> LENGTH: 23
<212> TYPE: RNA
<213> ORGANISM: Artificial Sequence
<220> FEATURE:
<223> OTHER INFORMATION: Synthetic: mmu-miR-1967

<400> SEQUENCE: 161
ugaggauccu ggggagaaga ugc                                                    23

<210> SEQ ID NO 162
<211> LENGTH: 22
<212> TYPE: RNA
<213> ORGANISM: Artificial Sequence
<220> FEATURE:
<223> OTHER INFORMATION: Synthetic: mmu-miR-101a*

<400> SEQUENCE: 162
ucaguuauca cagugcugau gc                                                     22

<210> SEQ ID NO 163
<211> LENGTH: 25
<212> TYPE: RNA
<213> ORGANISM: Artificial Sequence
<220> FEATURE:
<223> OTHER INFORMATION: Synthetic: mmu-miR-541

<400> SEQUENCE: 163
aagggauucu gauguugguc acacu                                                  25

<210> SEQ ID NO 164
<211> LENGTH: 24
<212> TYPE: RNA
<213> ORGANISM: Artificial Sequence
<220> FEATURE:
<223> OTHER INFORMATION: Synthetic: mmu-miR-453

<400> SEQUENCE: 164
agguugccuc auagugagcu ugca                                                   24

<210> SEQ ID NO 165
<211> LENGTH: 22
<212> TYPE: RNA
<213> ORGANISM: Artificial Sequence
<220> FEATURE:
<223> OTHER INFORMATION: Synthetic: mmu-miR-33*

<400> SEQUENCE: 165
caauguuucc acagugcauc ac                                                     22

<210> SEQ ID NO 166
<211> LENGTH: 22
<212> TYPE: RNA
<213> ORGANISM: Artificial Sequence
<220> FEATURE:
<223> OTHER INFORMATION: Synthetic: mmu-miR-206

<400> SEQUENCE: 166
uggaauguaa ggaagugugu gg                                                     22

```
<210> SEQ ID NO 167
<211> LENGTH: 23
<212> TYPE: RNA
<213> ORGANISM: Artificial Sequence
<220> FEATURE:
<223> OTHER INFORMATION: Synthetic: mmu-miR-181a

<400> SEQUENCE: 167
aacauucaac gcugucggug agu                                               23

<210> SEQ ID NO 168
<211> LENGTH: 22
<212> TYPE: RNA
<213> ORGANISM: Artificial Sequence
<220> FEATURE:
<223> OTHER INFORMATION: Synthetic: mmu-miR-133b

<400> SEQUENCE: 168
uuuggucccc uucaaccagc ua                                                22

<210> SEQ ID NO 169
<211> LENGTH: 22
<212> TYPE: RNA
<213> ORGANISM: Artificial Sequence
<220> FEATURE:
<223> OTHER INFORMATION: Synthetic: mmu-miR-133a

<400> SEQUENCE: 169
uuuggucccc uucaaccagc ug                                                22

<210> SEQ ID NO 170
<211> LENGTH: 22
<212> TYPE: RNA
<213> ORGANISM: Artificial Sequence
<220> FEATURE:
<223> OTHER INFORMATION: Synthetic: mmu-miR-196b

<400> SEQUENCE: 170
uagguaguuu ccuguuguug gg                                                22

<210> SEQ ID NO 171
<211> LENGTH: 22
<212> TYPE: RNA
<213> ORGANISM: Artificial Sequence
<220> FEATURE:
<223> OTHER INFORMATION: Synthetic: mmu-miR-181c

<400> SEQUENCE: 171
aacauucaac cugucgguga gu                                                22

<210> SEQ ID NO 172
<211> LENGTH: 21
<212> TYPE: RNA
<213> ORGANISM: Artificial Sequence
<220> FEATURE:
<223> OTHER INFORMATION: Synthetic: mmu-miR-33

<400> SEQUENCE: 172
gugcauugua guugcauugc a                                                 21

<210> SEQ ID NO 173
<211> LENGTH: 22
<212> TYPE: RNA
<213> ORGANISM: Artificial Sequence
<220> FEATURE:
<223> OTHER INFORMATION: Synthetic: mmu-miR-1958
```

-continued

<400> SEQUENCE: 173
uaggaaagug gaagcaguaa gu                                          22

<210> SEQ ID NO 174
<211> LENGTH: 23
<212> TYPE: RNA
<213> ORGANISM: Artificial Sequence
<220> FEATURE:
<223> OTHER INFORMATION: Synthetic: mmu-miR-181d

<400> SEQUENCE: 174
aacauucauu guugucggug ggu                                         23

<210> SEQ ID NO 175
<211> LENGTH: 22
<212> TYPE: RNA
<213> ORGANISM: Artificial Sequence
<220> FEATURE:
<223> OTHER INFORMATION: Synthetic: mmu-miR-19a*

<400> SEQUENCE: 175
uaguuuugca uaguugcacu ac                                          22

<210> SEQ ID NO 176
<211> LENGTH: 22
<212> TYPE: RNA
<213> ORGANISM: Artificial Sequence
<220> FEATURE:
<223> OTHER INFORMATION: Synthetic: mmu-miR-34a

<400> SEQUENCE: 176
uggcaguguc uuagcugguu gu                                          22

<210> SEQ ID NO 177
<211> LENGTH: 23
<212> TYPE: RNA
<213> ORGANISM: Artificial Sequence
<220> FEATURE:
<223> OTHER INFORMATION: Synthetic: mmu-miR-34b-5p

<400> SEQUENCE: 177
aggcagugua auuagcugau ugu                                         23

<210> SEQ ID NO 178
<211> LENGTH: 21
<212> TYPE: RNA
<213> ORGANISM: Artificial Sequence
<220> FEATURE:
<223> OTHER INFORMATION: Synthetic: mmu-miR-379

<400> SEQUENCE: 178
ugguagacua uggaacguag g                                           21

<210> SEQ ID NO 179
<211> LENGTH: 21
<212> TYPE: RNA
<213> ORGANISM: Artificial Sequence
<220> FEATURE:
<223> OTHER INFORMATION: Synthetic: mmu-miR-188-3p

<400> SEQUENCE: 179
cucccacaug caggguuugc a                                           21

<210> SEQ ID NO 180

-continued

```
<211> LENGTH: 25
<212> TYPE: RNA
<213> ORGANISM: Artificial Sequence
<220> FEATURE:
<223> OTHER INFORMATION: Synthetic: mmu-miR-1955

<400> SEQUENCE: 180
agucccagga ugcacugcag cuuuu                                      25

<210> SEQ ID NO 181
<211> LENGTH: 23
<212> TYPE: RNA
<213> ORGANISM: Artificial Sequence
<220> FEATURE:
<223> OTHER INFORMATION: Synthetic: mmu-miR-93

<400> SEQUENCE: 181
caaagugcug uucgugcagg uag                                        23

<210> SEQ ID NO 182
<211> LENGTH: 22
<212> TYPE: RNA
<213> ORGANISM: Artificial Sequence
<220> FEATURE:
<223> OTHER INFORMATION: Synthetic: mmu-miR-582-5p

<400> SEQUENCE: 182
uacaguuguu caaccaguua cu                                         22

<210> SEQ ID NO 183
<211> LENGTH: 22
<212> TYPE: RNA
<213> ORGANISM: Artificial Sequence
<220> FEATURE:
<223> OTHER INFORMATION: Synthetic: mmu-miR-208b

<400> SEQUENCE: 183
auaagacgaa caaaagguuu gu                                         22

<210> SEQ ID NO 184
<211> LENGTH: 22
<212> TYPE: RNA
<213> ORGANISM: Artificial Sequence
<220> FEATURE:
<223> OTHER INFORMATION: Synthetic: mmu-miR-1956

<400> SEQUENCE: 184
aguccagggc ugagucagcg ga                                         22

<210> SEQ ID NO 185
<211> LENGTH: 21
<212> TYPE: RNA
<213> ORGANISM: Artificial Sequence
<220> FEATURE:
<223> OTHER INFORMATION: Synthetic: mmu-miR-2137

<400> SEQUENCE: 185
gccggcggga gccccaggga g                                          21

<210> SEQ ID NO 186
<211> LENGTH: 21
<212> TYPE: RNA
<213> ORGANISM: Artificial Sequence
<220> FEATURE:
<223> OTHER INFORMATION: Synthetic: mmu-miR-1188

<400> SEQUENCE: 186
```

-continued uggugugagg uugggccagg a                                                          21

<210> SEQ ID NO 187
<211> LENGTH: 22
<212> TYPE: RNA
<213> ORGANISM: Artificial Sequence
<220> FEATURE:
<223> OTHER INFORMATION: Synthetic: mmu-miR-483

<400> SEQUENCE: 187
aagacgggag aagagaaggg ag                                                         22

<210> SEQ ID NO 188
<211> LENGTH: 22
<212> TYPE: RNA
<213> ORGANISM: Artificial Sequence
<220> FEATURE:
<223> OTHER INFORMATION: Synthetic: mmu-miR-2138

<400> SEQUENCE: 188
aagggaacgg gcuuggcgga au                                                         22

<210> SEQ ID NO 189
<211> LENGTH: 21
<212> TYPE: RNA
<213> ORGANISM: Artificial Sequence
<220> FEATURE:
<223> OTHER INFORMATION: Synthetic: mmu-miR-676

<400> SEQUENCE: 189
ccguccugag guuguugagc u                                                          21

<210> SEQ ID NO 190
<211> LENGTH: 22
<212> TYPE: RNA
<213> ORGANISM: Artificial Sequence
<220> FEATURE:
<223> OTHER INFORMATION: Synthetic: mmu-miR-296-3p

<400> SEQUENCE: 190
gaggguuggg uggaggcucu cc                                                         22

<210> SEQ ID NO 191
<211> LENGTH: 22
<212> TYPE: RNA
<213> ORGANISM: Artificial Sequence
<220> FEATURE:
<223> OTHER INFORMATION: Synthetic: mmu-miR-1894-3p

<400> SEQUENCE: 191
gcaagggaga gggugaaggg ag                                                         22

<210> SEQ ID NO 192
<211> LENGTH: 22
<212> TYPE: RNA
<213> ORGANISM: Artificial Sequence
<220> FEATURE:
<223> OTHER INFORMATION: Synthetic: mmu-miR-205

<400> SEQUENCE: 192
uccuucauuc caccggaguc ug                                                         22

<210> SEQ ID NO 193
<211> LENGTH: 23
<212> TYPE: RNA

-continued

<213> ORGANISM: Artificial Sequence
<220> FEATURE:
<223> OTHER INFORMATION: Synthetic: mmu-miR-423-3p

<400> SEQUENCE: 193
agcucggucu gaggcccuc agu                                                          23

<210> SEQ ID NO 194
<211> LENGTH: 22
<212> TYPE: RNA
<213> ORGANISM: Artificial Sequence
<220> FEATURE:
<223> OTHER INFORMATION: Synthetic: mmu-miR-883b-5p

<400> SEQUENCE: 194
uacugagaau ggguagcagu ca                                                          22

<210> SEQ ID NO 195
<211> LENGTH: 21
<212> TYPE: RNA
<213> ORGANISM: Artificial Sequence
<220> FEATURE:
<223> OTHER INFORMATION: Synthetic: mmu-miR-685

<400> SEQUENCE: 195
ucaauggcug aggugaggca c                                                           21

<210> SEQ ID NO 196
<211> LENGTH: 22
<212> TYPE: RNA
<213> ORGANISM: Artificial Sequence
<220> FEATURE:
<223> OTHER INFORMATION: Synthetic: mmu-miR-331-5p

<400> SEQUENCE: 196
cuagguaugg ucccagggau cc                                                          22

<210> SEQ ID NO 197
<211> LENGTH: 17
<212> TYPE: RNA
<213> ORGANISM: Artificial Sequence
<220> FEATURE:
<223> OTHER INFORMATION: Synthetic: mmu-miR-1928

<400> SEQUENCE: 197
agcuacauug ccagcuc                                                                17

<210> SEQ ID NO 198
<211> LENGTH: 17
<212> TYPE: RNA
<213> ORGANISM: Artificial Sequence
<220> FEATURE:
<223> OTHER INFORMATION: Synthetic: mmu-miR-1952

<400> SEQUENCE: 198
ucuccacccu ccuucug                                                                17

<210> SEQ ID NO 199
<211> LENGTH: 21
<212> TYPE: RNA
<213> ORGANISM: Artificial Sequence
<220> FEATURE:
<223> OTHER INFORMATION: Synthetic: mmu-miR-466g

<400> SEQUENCE: 199
auacagacac augcacacac a                                                           21

-continued

```
<210> SEQ ID NO 200
<211> LENGTH: 22
<212> TYPE: RNA
<213> ORGANISM: Artificial Sequence
<220> FEATURE:
<223> OTHER INFORMATION: Synthetic: mmu-miR-669a

<400> SEQUENCE: 200
aguugugugu gcauguucau gu                                                    22

<210> SEQ ID NO 201
<211> LENGTH: 22
<212> TYPE: RNA
<213> ORGANISM: Artificial Sequence
<220> FEATURE:
<223> OTHER INFORMATION: Synthetic: mmu-miR-574-3p

<400> SEQUENCE: 201
cacgcucaug cacacaccca ca                                                    22

<210> SEQ ID NO 202
<211> LENGTH: 22
<212> TYPE: RNA
<213> ORGANISM: Artificial Sequence
<220> FEATURE:
<223> OTHER INFORMATION: Synthetic: mmu-miR-452

<400> SEQUENCE: 202
uguuugcaga ggaaacugag ac                                                    22

<210> SEQ ID NO 203
<211> LENGTH: 22
<212> TYPE: RNA
<213> ORGANISM: Artificial Sequence
<220> FEATURE:
<223> OTHER INFORMATION: Synthetic: mmu-miR-1894-5p

<400> SEQUENCE: 203
cucuccccua ccaccugccu cu                                                    22

<210> SEQ ID NO 204
<211> LENGTH: 19
<212> TYPE: RNA
<213> ORGANISM: Artificial Sequence
<220> FEATURE:
<223> OTHER INFORMATION: Synthetic: mmu-miR-327

<400> SEQUENCE: 204
acuugagggg caugaggau                                                        19

<210> SEQ ID NO 205
<211> LENGTH: 23
<212> TYPE: RNA
<213> ORGANISM: Artificial Sequence
<220> FEATURE:
<223> OTHER INFORMATION: Synthetic: mmu-miR-342-3p

<400> SEQUENCE: 205
ucucacacag aaaucgcacc cgu                                                   23

<210> SEQ ID NO 206
<211> LENGTH: 22
<212> TYPE: RNA
<213> ORGANISM: Artificial Sequence
<220> FEATURE:
```

<223> OTHER INFORMATION: Synthetic: mmu-miR-218-1*

<400> SEQUENCE: 206
aaacaugguu ccgucaagca cc                                                                22

<210> SEQ ID NO 207
<211> LENGTH: 22
<212> TYPE: RNA
<213> ORGANISM: Artificial Sequence
<220> FEATURE:
<223> OTHER INFORMATION: Synthetic: mmu-miR-10b*

<400> SEQUENCE: 207
cagauucgau ucuaggggaa ua                                                                22

<210> SEQ ID NO 208
<211> LENGTH: 22
<212> TYPE: RNA
<213> ORGANISM: Artificial Sequence
<220> FEATURE:
<223> OTHER INFORMATION: Synthetic: mmu-miR-1186

<400> SEQUENCE: 208
gagugcugga auuaaaggca ug                                                                22

<210> SEQ ID NO 209
<211> LENGTH: 22
<212> TYPE: RNA
<213> ORGANISM: Artificial Sequence
<220> FEATURE:
<223> OTHER INFORMATION: Synthetic: mmu-miR-466a-5p

<400> SEQUENCE: 209
uaugugugug uacauguaca ua                                                                22

<210> SEQ ID NO 210
<211> LENGTH: 22
<212> TYPE: RNA
<213> ORGANISM: Artificial Sequence
<220> FEATURE:
<223> OTHER INFORMATION: Synthetic: mmu-miR-675-5p

<400> SEQUENCE: 210
uggugcggaa agggcccaca gu                                                                22

<210> SEQ ID NO 211
<211> LENGTH: 22
<212> TYPE: RNA
<213> ORGANISM: Artificial Sequence
<220> FEATURE:
<223> OTHER INFORMATION: Synthetic: mmu-miR-467c

<400> SEQUENCE: 211
uaagugcgug cauguauaug ug                                                                22

<210> SEQ ID NO 212
<211> LENGTH: 22
<212> TYPE: RNA
<213> ORGANISM: Artificial Sequence
<220> FEATURE:
<223> OTHER INFORMATION: Synthetic: mmu-miR-1194

<400> SEQUENCE: 212
gaaugaguaa cugcuagauc cu                                                                22

-continued

<210> SEQ ID NO 213
<211> LENGTH: 22
<212> TYPE: RNA
<213> ORGANISM: Artificial Sequence
<220> FEATURE:
<223> OTHER INFORMATION: Synthetic: mmu-miR-669b

<400> SEQUENCE: 213
aguuuugugu gcaugugcau gu                                                                      22

<210> SEQ ID NO 214
<211> LENGTH: 22
<212> TYPE: RNA
<213> ORGANISM: Artificial Sequence
<220> FEATURE:
<223> OTHER INFORMATION: Synthetic: mmu-miR-138*

<400> SEQUENCE: 214
cggcuacuuc acaacaccag gg                                                                      22

<210> SEQ ID NO 215
<211> LENGTH: 21
<212> TYPE: RNA
<213> ORGANISM: Artificial Sequence
<220> FEATURE:
<223> OTHER INFORMATION: Synthetic: mmu-miR-680

<400> SEQUENCE: 215
gggcaucugc ugacaugggg g                                                                       21

<210> SEQ ID NO 216
<211> LENGTH: 23
<212> TYPE: RNA
<213> ORGANISM: Artificial Sequence
<220> FEATURE:
<223> OTHER INFORMATION: Synthetic: mmu-miR-423-5p

<400> SEQUENCE: 216
ugaggggcag agagcgagac uuu                                                                     23

<210> SEQ ID NO 217
<211> LENGTH: 21
<212> TYPE: RNA
<213> ORGANISM: Artificial Sequence
<220> FEATURE:
<223> OTHER INFORMATION: Synthetic: mmu-miR-220

<400> SEQUENCE: 217
ccaccacagu gucagacacu u                                                                       21

<210> SEQ ID NO 218
<211> LENGTH: 23
<212> TYPE: RNA
<213> ORGANISM: Artificial Sequence
<220> FEATURE:
<223> OTHER INFORMATION: Synthetic: mmu-miR-669o

<400> SEQUENCE: 218
uaguugugug ugcauguuua ugu                                                                     23

<210> SEQ ID NO 219
<211> LENGTH: 22
<212> TYPE: RNA
<213> ORGANISM: Artificial Sequence
<220> FEATURE:
<223> OTHER INFORMATION: Synthetic: mmu-miR-763

-continued

```
<400> SEQUENCE: 219
ccagcuggga agaaccagug gc                                          22

<210> SEQ ID NO 220
<211> LENGTH: 22
<212> TYPE: RNA
<213> ORGANISM: Artificial Sequence
<220> FEATURE:
<223> OTHER INFORMATION: Synthetic: mmu-miR-383

<400> SEQUENCE: 220
agaucagaag gugacugugg cu                                          22

<210> SEQ ID NO 221
<211> LENGTH: 22
<212> TYPE: RNA
<213> ORGANISM: Artificial Sequence
<220> FEATURE:
<223> OTHER INFORMATION: Synthetic: mmu-miR-295*

<400> SEQUENCE: 221
acucaaaugu ggggcacacu uc                                          22

<210> SEQ ID NO 222
<211> LENGTH: 23
<212> TYPE: RNA
<213> ORGANISM: Artificial Sequence
<220> FEATURE:
<223> OTHER INFORMATION: Synthetic: mmu-miR-672

<400> SEQUENCE: 222
ugagguuggu guacugugug uga                                         23

<210> SEQ ID NO 223
<211> LENGTH: 22
<212> TYPE: RNA
<213> ORGANISM: Artificial Sequence
<220> FEATURE:
<223> OTHER INFORMATION: Synthetic: mmu-miR-300

<400> SEQUENCE: 223
uaugcaaggg caagcucucu uc                                          22

<210> SEQ ID NO 224
<211> LENGTH: 22
<212> TYPE: RNA
<213> ORGANISM: Artificial Sequence
<220> FEATURE:
<223> OTHER INFORMATION: Synthetic: mmu-miR-1190

<400> SEQUENCE: 224
ucagcugagg uuccccucug uc                                          22

<210> SEQ ID NO 225
<211> LENGTH: 21
<212> TYPE: RNA
<213> ORGANISM: Artificial Sequence
<220> FEATURE:
<223> OTHER INFORMATION: Synthetic: mmu-miR-669i

<400> SEQUENCE: 225
ugcauauaca cacaugcaua c                                           21

<210> SEQ ID NO 226
<211> LENGTH: 18
```

-continued

```
<212> TYPE: RNA
<213> ORGANISM: Artificial Sequence
<220> FEATURE:
<223> OTHER INFORMATION: Synthetic: mmu-miR-2183

<400> SEQUENCE: 226
uugaaccccu gaccuccu                                             18

<210> SEQ ID NO 227
<211> LENGTH: 21
<212> TYPE: RNA
<213> ORGANISM: Artificial Sequence
<220> FEATURE:
<223> OTHER INFORMATION: Synthetic: mmu-miR-683

<400> SEQUENCE: 227
ccugcuguaa gcuguguccu c                                         21

<210> SEQ ID NO 228
<211> LENGTH: 21
<212> TYPE: RNA
<213> ORGANISM: Artificial Sequence
<220> FEATURE:
<223> OTHER INFORMATION: Synthetic: mmu-miR-466f-3p

<400> SEQUENCE: 228
cauacacaca cacauacaca c                                         21

<210> SEQ ID NO 229
<211> LENGTH: 21
<212> TYPE: RNA
<213> ORGANISM: Artificial Sequence
<220> FEATURE:
<223> OTHER INFORMATION: Synthetic: mmu-miR-376b

<400> SEQUENCE: 229
aucauagagg aacauccacu u                                         21

<210> SEQ ID NO 230
<211> LENGTH: 22
<212> TYPE: RNA
<213> ORGANISM: Artificial Sequence
<220> FEATURE:
<223> OTHER INFORMATION: Synthetic: mmu-miR-122

<400> SEQUENCE: 230
uggaguguga caauggguu ug                                         22

<210> SEQ ID NO 231
<211> LENGTH: 22
<212> TYPE: RNA
<213> ORGANISM: Artificial Sequence
<220> FEATURE:
<223> OTHER INFORMATION: Synthetic: mmu-miR-679

<400> SEQUENCE: 231
ggacugugag gugacucuug gu                                         22

<210> SEQ ID NO 232
<211> LENGTH: 22
<212> TYPE: RNA
<213> ORGANISM: Artificial Sequence
<220> FEATURE:
<223> OTHER INFORMATION: Synthetic: mmu-miR-363

<400> SEQUENCE: 232
```

-continued aauugcacgg uauccaucug ua                                    22

<210> SEQ ID NO 233
<211> LENGTH: 19
<212> TYPE: RNA
<213> ORGANISM: Artificial Sequence
<220> FEATURE:
<223> OTHER INFORMATION: Synthetic: mmu-miR-698

<400> SEQUENCE: 233
cauucucguu uccuucccu                                        19

<210> SEQ ID NO 234
<211> LENGTH: 21
<212> TYPE: RNA
<213> ORGANISM: Artificial Sequence
<220> FEATURE:
<223> OTHER INFORMATION: Synthetic: mmu-miR-551b

<400> SEQUENCE: 234
gcgacccaua cuugguuuca g                                     21

<210> SEQ ID NO 235
<211> LENGTH: 22
<212> TYPE: RNA
<213> ORGANISM: Artificial Sequence
<220> FEATURE:
<223> OTHER INFORMATION: Synthetic: mmu-miR-139-3p

<400> SEQUENCE: 235
uggagacgcg gcccuguugg ag                                    22

<210> SEQ ID NO 236
<211> LENGTH: 22
<212> TYPE: RNA
<213> ORGANISM: Artificial Sequence
<220> FEATURE:
<223> OTHER INFORMATION: Synthetic: mmu-miR-1198

<400> SEQUENCE: 236 uauuguucc uggcuggcuu gg                                      22

<210> SEQ ID NO 237
<211> LENGTH: 22
<212> TYPE: RNA
<213> ORGANISM: Artificial Sequence
<220> FEATURE:
<223> OTHER INFORMATION: Synthetic: mmu-miR-338-5p

<400> SEQUENCE: 237
aacaauaucc uggugcugag ug                                     22

<210> SEQ ID NO 238
<211> LENGTH: 20
<212> TYPE: RNA
<213> ORGANISM: Artificial Sequence
<220> FEATURE:
<223> OTHER INFORMATION: Synthetic: mmu-miR-705

<400> SEQUENCE: 238
ggugggaggu ggggugggca                                       20

<210> SEQ ID NO 239
<211> LENGTH: 22
<212> TYPE: RNA
<213> ORGANISM: Artificial Sequence -continued

```
<220> FEATURE:
<223> OTHER INFORMATION: Synthetic: mmu-miR-710

<400> SEQUENCE: 239
ccaagucuug gggagaguug ag                                                   22

<210> SEQ ID NO 240
<211> LENGTH: 22
<212> TYPE: RNA
<213> ORGANISM: Artificial Sequence
<220> FEATURE:
<223> OTHER INFORMATION: Synthetic: mmu-miR-20b*

<400> SEQUENCE: 240
acugcagugu gagcacuucu ag                                                   22

<210> SEQ ID NO 241
<211> LENGTH: 22
<212> TYPE: RNA
<213> ORGANISM: Artificial Sequence
<220> FEATURE:
<223> OTHER INFORMATION: Synthetic: mmu-miR-329

<400> SEQUENCE: 241
aacacaccca gcuaaccuuu uu                                                   22

<210> SEQ ID NO 242
<211> LENGTH: 20
<212> TYPE: RNA
<213> ORGANISM: Artificial Sequence
<220> FEATURE:
<223> OTHER INFORMATION: Synthetic: mmu-miR-1982*

<400> SEQUENCE: 242
uugggagggu ccugggagg                                                      20

<210> SEQ ID NO 243
<211> LENGTH: 19
<212> TYPE: RNA
<213> ORGANISM: Artificial Sequence
<220> FEATURE:
<223> OTHER INFORMATION: Synthetic: mmu-miR-694

<400> SEQUENCE: 243
cugaaaaugu ugccugaag                                                      19

<210> SEQ ID NO 244
<211> LENGTH: 22
<212> TYPE: RNA
<213> ORGANISM: Artificial Sequence
<220> FEATURE:
<223> OTHER INFORMATION: Synthetic: mmu-miR-485

<400> SEQUENCE: 244
agaggcuggc cgugaugaau uc                                                   22

<210> SEQ ID NO 245
<211> LENGTH: 21
<212> TYPE: RNA
<213> ORGANISM: Artificial Sequence
<220> FEATURE:
<223> OTHER INFORMATION: Synthetic: mmu-miR-511

<400> SEQUENCE: 245
augccuuuug cucugcacuc a                                                    21
```

-continued

```
<210> SEQ ID NO 246
<211> LENGTH: 21
<212> TYPE: RNA
<213> ORGANISM: Artificial Sequence
<220> FEATURE:
<223> OTHER INFORMATION: Synthetic: mmu-miR-693-5p

<400> SEQUENCE: 246
cagccacauc cgaaaguuuu c                                                   21

<210> SEQ ID NO 247
<211> LENGTH: 22
<212> TYPE: RNA
<213> ORGANISM: Artificial Sequence
<220> FEATURE:
<223> OTHER INFORMATION: Synthetic: mmu-miR-1895

<400> SEQUENCE: 247
cccccgagga ggacgaggag ga                                                  22

<210> SEQ ID NO 248
<211> LENGTH: 22
<212> TYPE: RNA
<213> ORGANISM: Artificial Sequence
<220> FEATURE:
<223> OTHER INFORMATION: Synthetic: mmu-miR-345-5p

<400> SEQUENCE: 248
gcugaccccu aguccagugc uu                                                  22

<210> SEQ ID NO 249
<211> LENGTH: 22
<212> TYPE: RNA
<213> ORGANISM: Artificial Sequence
<220> FEATURE:
<223> OTHER INFORMATION: Synthetic: mmu-miR-127*

<400> SEQUENCE: 249
cugaagcuca gagggcucug au                                                  22

<210> SEQ ID NO 250
<211> LENGTH: 22
<212> TYPE: RNA
<213> ORGANISM: Artificial Sequence
<220> FEATURE:
<223> OTHER INFORMATION: Synthetic: mmu-miR-34b-3p

<400> SEQUENCE: 250
aaucacuaac uccacugcca uc                                                  22

<210> SEQ ID NO 251
<211> LENGTH: 22
<212> TYPE: RNA
<213> ORGANISM: Artificial Sequence
<220> FEATURE:
<223> OTHER INFORMATION: Synthetic: mmu-miR-544

<400> SEQUENCE: 251
auucugcauu uuuagcaagc uc                                                  22

<210> SEQ ID NO 252
<211> LENGTH: 21
<212> TYPE: RNA
<213> ORGANISM: Artificial Sequence
<220> FEATURE:
<223> OTHER INFORMATION: Synthetic: mmu-miR-873
```

-continued

```
<400> SEQUENCE: 252
gcaggaacuu gugagucucc u                                              21

<210> SEQ ID NO 253
<211> LENGTH: 22
<212> TYPE: RNA
<213> ORGANISM: Artificial Sequence
<220> FEATURE:
<223> OTHER INFORMATION: Synthetic: mmu-miR-16*

<400> SEQUENCE: 253
ccaguauuga cugugcugcu ga                                             22

<210> SEQ ID NO 254
<211> LENGTH: 25
<212> TYPE: RNA
<213> ORGANISM: Artificial Sequence
<220> FEATURE:
<223> OTHER INFORMATION: Synthetic: mmu-miR-2143

<400> SEQUENCE: 254
cgagguggga ucccgaggcc ucucc                                          25

<210> SEQ ID NO 255
<211> LENGTH: 23
<212> TYPE: RNA
<213> ORGANISM: Artificial Sequence
<220> FEATURE:
<223> OTHER INFORMATION: Synthetic: mmu-miR-673-3p

<400> SEQUENCE: 255
uccggggcug aguucgugc acc                                             23

<210> SEQ ID NO 256
<211> LENGTH: 20
<212> TYPE: RNA
<213> ORGANISM: Artificial Sequence
<220> FEATURE:
<223> OTHER INFORMATION: Synthetic: mmu-miR-760

<400> SEQUENCE: 256
cggcucuggg ucugugggga                                                20

<210> SEQ ID NO 257
<211> LENGTH: 22
<212> TYPE: RNA
<213> ORGANISM: Artificial Sequence
<220> FEATURE:
<223> OTHER INFORMATION: Synthetic: mmu-miR-711

<400> SEQUENCE: 257
gggacccggg gagagaugua ag                                             22

<210> SEQ ID NO 258
<211> LENGTH: 22
<212> TYPE: RNA
<213> ORGANISM: Artificial Sequence
<220> FEATURE:
<223> OTHER INFORMATION: Synthetic: mmu-miR-141*

<400> SEQUENCE: 258
caucuuccag ugcaguguug ga                                             22

<210> SEQ ID NO 259
```

-continued

```
<211> LENGTH: 22
<212> TYPE: RNA
<213> ORGANISM: Artificial Sequence
<220> FEATURE:
<223> OTHER INFORMATION: Synthetic: mmu-miR-496

<400> SEQUENCE: 259
ugaguauuac auggccaauc uc                                          22

<210> SEQ ID NO 260
<211> LENGTH: 21
<212> TYPE: RNA
<213> ORGANISM: Artificial Sequence
<220> FEATURE:
<223> OTHER INFORMATION: Synthetic: mmu-miR-669k

<400> SEQUENCE: 260
uaugcauaua cacgcaugca a                                           21

<210> SEQ ID NO 261
<211> LENGTH: 23
<212> TYPE: RNA
<213> ORGANISM: Artificial Sequence
<220> FEATURE:
<223> OTHER INFORMATION: Synthetic: mmu-miR-464

<400> SEQUENCE: 261
uaccaaguuu auucugugag aua                                         23

<210> SEQ ID NO 262
<211> LENGTH: 22
<212> TYPE: RNA
<213> ORGANISM: Artificial Sequence
<220> FEATURE:
<223> OTHER INFORMATION: Synthetic: mmu-miR-1192

<400> SEQUENCE: 262
aaacaaacaa acagaccaaa uu                                          22

<210> SEQ ID NO 263
<211> LENGTH: 22
<212> TYPE: RNA
<213> ORGANISM: Artificial Sequence
<220> FEATURE:
<223> OTHER INFORMATION: Synthetic: mmu-miR-127

<400> SEQUENCE: 263
ucggauccgu cugagcuugg cu                                          22

<210> SEQ ID NO 264
<211> LENGTH: 22
<212> TYPE: RNA
<213> ORGANISM: Artificial Sequence
<220> FEATURE:
<223> OTHER INFORMATION: Synthetic: mmu-miR-1905

<400> SEQUENCE: 264
caccaguccc accacgcggu ag                                          22

<210> SEQ ID NO 265
<211> LENGTH: 22
<212> TYPE: RNA
<213> ORGANISM: Artificial Sequence
<220> FEATURE:
<223> OTHER INFORMATION: Synthetic: mmu-miR-290-5p

<400> SEQUENCE: 265
```

-continued acucaaacua uggggggcacu uu                                                        22

<210> SEQ ID NO 266
<211> LENGTH: 23
<212> TYPE: RNA
<213> ORGANISM: Artificial Sequence
<220> FEATURE:
<223> OTHER INFORMATION: Synthetic: mmu-miR-1195

<400> SEQUENCE: 266
ugaguucgag gccagccugc uca                                                        23

<210> SEQ ID NO 267
<211> LENGTH: 22
<212> TYPE: RNA
<213> ORGANISM: Artificial Sequence
<220> FEATURE:
<223> OTHER INFORMATION: Synthetic: mmu-miR-877*

<400> SEQUENCE: 267
uguccucuuc ucccuccucc ca                                                         22

<210> SEQ ID NO 268
<211> LENGTH: 22
<212> TYPE: RNA
<213> ORGANISM: Artificial Sequence
<220> FEATURE:
<223> OTHER INFORMATION: Synthetic: mmu-miR-297b-3p

<400> SEQUENCE: 268
uauacauaca cacauaccca ua                                                         22

<210> SEQ ID NO 269
<211> LENGTH: 23
<212> TYPE: RNA
<213> ORGANISM: Artificial Sequence
<220> FEATURE:
<223> OTHER INFORMATION: Synthetic: mmu-miR-1982.1

<400> SEQUENCE: 269
ucucacccua uguucuccca cag                                                        23

<210> SEQ ID NO 270
<211> LENGTH: 21
<212> TYPE: RNA
<213> ORGANISM: Artificial Sequence
<220> FEATURE:
<223> OTHER INFORMATION: Synthetic: mmu-miR-1941-3p

<400> SEQUENCE: 270
caucuuagca guaucuccca u                                                          21

<210> SEQ ID NO 271
<211> LENGTH: 22
<212> TYPE: RNA
<213> ORGANISM: Artificial Sequence
<220> FEATURE:
<223> OTHER INFORMATION: Synthetic: mmu-miR-1904

<400> SEQUENCE: 271
guucugcucc ucuggaggga gg                                                         22

<210> SEQ ID NO 272
<211> LENGTH: 22
<212> TYPE: RNA

<213> ORGANISM: Artificial Sequence
<220> FEATURE:
<223> OTHER INFORMATION: Synthetic: mmu-miR-501-3p

<400> SEQUENCE: 272
aaugcacccg ggcaaggauu ug                                                                        22

<210> SEQ ID NO 273
<211> LENGTH: 21
<212> TYPE: RNA
<213> ORGANISM: Artificial Sequence
<220> FEATURE:
<223> OTHER INFORMATION: Synthetic: mmu-miR-2136

<400> SEQUENCE: 273
cugggguuug acugagaugu g                                                                         21

<210> SEQ ID NO 274
<211> LENGTH: 22
<212> TYPE: RNA
<213> ORGANISM: Artificial Sequence
<220> FEATURE:
<223> OTHER INFORMATION: Synthetic: mmu-miR-1897-3p

<400> SEQUENCE: 274
ucaacucguu cuguccggug ag                                                                        22

<210> SEQ ID NO 275
<211> LENGTH: 23
<212> TYPE: RNA
<213> ORGANISM: Artificial Sequence
<220> FEATURE:
<223> OTHER INFORMATION: Synthetic: mmu-miR-1936

<400> SEQUENCE: 275
uaacugaccu gcugugaacu ggc                                                                       23

<210> SEQ ID NO 276
<211> LENGTH: 22
<212> TYPE: RNA
<213> ORGANISM: Artificial Sequence
<220> FEATURE:
<223> OTHER INFORMATION: Synthetic: mmu-miR-744*

<400> SEQUENCE: 276
cuguugccac uaaccucaac cu                                                                        22

<210> SEQ ID NO 277
<211> LENGTH: 23
<212> TYPE: RNA
<213> ORGANISM: Artificial Sequence
<220> FEATURE:
<223> OTHER INFORMATION: Synthetic: mmu-miR-466b-3-3p

<400> SEQUENCE: 277
aauacauaca cgcacacaua aga                                                                       23

<210> SEQ ID NO 278
<211> LENGTH: 24
<212> TYPE: RNA
<213> ORGANISM: Artificial Sequence
<220> FEATURE:
<223> OTHER INFORMATION: Synthetic: mmu-miR-292-3p

<400> SEQUENCE: 278
aaagugccgc cagguuuuga gugu                                                                      24

<210> SEQ ID NO 279
<211> LENGTH: 22
<212> TYPE: RNA
<213> ORGANISM: Artificial Sequence
<220> FEATURE:
<223> OTHER INFORMATION: Synthetic: mmu-miR-1953

<400> SEQUENCE: 279
ugggaaaguu cucaggcuuc ug                                        22

<210> SEQ ID NO 280
<211> LENGTH: 21
<212> TYPE: RNA
<213> ORGANISM: Artificial Sequence
<220> FEATURE:
<223> OTHER INFORMATION: Synthetic: mmu-miR-682

<400> SEQUENCE: 280
cugcagucac agugaagucu g                                         21

<210> SEQ ID NO 281
<211> LENGTH: 22
<212> TYPE: RNA
<213> ORGANISM: Artificial Sequence
<220> FEATURE:
<223> OTHER INFORMATION: Synthetic: mmu-miR-212

<400> SEQUENCE: 281
uaacagucuc cagucacggc ca                                        22

<210> SEQ ID NO 282
<211> LENGTH: 22
<212> TYPE: RNA
<213> ORGANISM: Artificial Sequence
<220> FEATURE:
<223> OTHER INFORMATION: Synthetic: mmu-miR-154

<400> SEQUENCE: 282
uagguuaucc guguugccuu cg                                        22

<210> SEQ ID NO 283
<211> LENGTH: 21
<212> TYPE: RNA
<213> ORGANISM: Artificial Sequence
<220> FEATURE:
<223> OTHER INFORMATION: Synthetic: mmu-miR-467f

<400> SEQUENCE: 283
auauacacac acacaccuac a                                         21

<210> SEQ ID NO 284
<211> LENGTH: 22
<212> TYPE: RNA
<213> ORGANISM: Artificial Sequence
<220> FEATURE:
<223> OTHER INFORMATION: Synthetic: mmu-miR-466i

<400> SEQUENCE: 284
auacacacac acauacacac ua                                        22

<210> SEQ ID NO 285
<211> LENGTH: 21
<212> TYPE: RNA
<213> ORGANISM: Artificial Sequence
<220> FEATURE:

<223> OTHER INFORMATION: Synthetic: mmu-miR-712

<400> SEQUENCE: 285
cuccuucacc cgggcgguac c                                          21

<210> SEQ ID NO 286
<211> LENGTH: 22
<212> TYPE: RNA
<213> ORGANISM: Artificial Sequence
<220> FEATURE:
<223> OTHER INFORMATION: Synthetic: mmu-miR-467e*

<400> SEQUENCE: 286
auauacauac acacaccuau au                                         22

<210> SEQ ID NO 287
<211> LENGTH: 22
<212> TYPE: RNA
<213> ORGANISM: Artificial Sequence
<220> FEATURE:
<223> OTHER INFORMATION: Synthetic: mmu-miR-504

<400> SEQUENCE: 287
agacccuggu cugcacucua uc                                         22

<210> SEQ ID NO 288
<211> LENGTH: 22
<212> TYPE: RNA
<213> ORGANISM: Artificial Sequence
<220> FEATURE:
<223> OTHER INFORMATION: Synthetic: mmu-miR-465b-3p

<400> SEQUENCE: 288
gaucagggcc uuucuaagua ga                                         22

<210> SEQ ID NO 289
<211> LENGTH: 22
<212> TYPE: RNA
<213> ORGANISM: Artificial Sequence
<220> FEATURE:
<223> OTHER INFORMATION: Synthetic: mmu-miR-467d*

<400> SEQUENCE: 289
auauacauac acacaccuac ac                                         22

<210> SEQ ID NO 290
<211> LENGTH: 22
<212> TYPE: RNA
<213> ORGANISM: Artificial Sequence
<220> FEATURE:
<223> OTHER INFORMATION: Synthetic: mmu-miR-450a-3p

<400> SEQUENCE: 290
auuggggaug cuuugcauuc au                                         22

<210> SEQ ID NO 291
<211> LENGTH: 23
<212> TYPE: RNA
<213> ORGANISM: Artificial Sequence
<220> FEATURE:
<223> OTHER INFORMATION: Synthetic: mmu-miR-1934

<400> SEQUENCE: 291
ucuggucccc ugcuucgucc ucu                                        23

-continued

<210> SEQ ID NO 292
<211> LENGTH: 21
<212> TYPE: RNA
<213> ORGANISM: Artificial Sequence
<220> FEATURE:
<223> OTHER INFORMATION: Synthetic: mmu-miR-467g

<400> SEQUENCE: 292
uauacauaca cacacauaua u                                                                    21

<210> SEQ ID NO 293
<211> LENGTH: 22
<212> TYPE: RNA
<213> ORGANISM: Artificial Sequence
<220> FEATURE:
<223> OTHER INFORMATION: Synthetic: mmu-miR-467e

<400> SEQUENCE: 293
auaaguguga gcauguauau gu                                                                   22

<210> SEQ ID NO 294
<211> LENGTH: 23
<212> TYPE: RNA
<213> ORGANISM: Artificial Sequence
<220> FEATURE:
<223> OTHER INFORMATION: Synthetic: mmu-miR-302a

<400> SEQUENCE: 294
uaagugcuuc cauguuuugg uga                                                                  23

<210> SEQ ID NO 295
<211> LENGTH: 22
<212> TYPE: RNA
<213> ORGANISM: Artificial Sequence
<220> FEATURE:
<223> OTHER INFORMATION: Synthetic: mmu-miR-1950

<400> SEQUENCE: 295
ucugcaucua aggauauggu ca                                                                   22

<210> SEQ ID NO 296
<211> LENGTH: 21
<212> TYPE: RNA
<213> ORGANISM: Artificial Sequence
<220> FEATURE:
<223> OTHER INFORMATION: Synthetic: mmu-miR-697

<400> SEQUENCE: 296
aacauccugg uccuguggag a                                                                    21

<210> SEQ ID NO 297
<211> LENGTH: 22
<212> TYPE: RNA
<213> ORGANISM: Artificial Sequence
<220> FEATURE:
<223> OTHER INFORMATION: Synthetic: mmu-miR-466d-5p

<400> SEQUENCE: 297
ugugugugcg uacauguaca ug                                                                   22

<210> SEQ ID NO 298
<211> LENGTH: 22
<212> TYPE: RNA
<213> ORGANISM: Artificial Sequence
<220> FEATURE:
<223> OTHER INFORMATION: Synthetic: mmu-miR-883b-3p -continued

```
<400> SEQUENCE: 298
uaacugcaac aucucucagu au                                              22

<210> SEQ ID NO 299
<211> LENGTH: 21
<212> TYPE: RNA
<213> ORGANISM: Artificial Sequence
<220> FEATURE:
<223> OTHER INFORMATION: Synthetic: mmu-miR-704

<400> SEQUENCE: 299
agacaugugc ucugcuccua g                                               21

<210> SEQ ID NO 300
<211> LENGTH: 22
<212> TYPE: RNA
<213> ORGANISM: Artificial Sequence
<220> FEATURE:
<223> OTHER INFORMATION: Synthetic: mmu-miR-4661

<400> SEQUENCE: 300
uauaaauaca ugcacacaua uu                                              22

<210> SEQ ID NO 301
<211> LENGTH: 20
<212> TYPE: RNA
<213> ORGANISM: Artificial Sequence
<220> FEATURE:
<223> OTHER INFORMATION: Synthetic: mmu-miR-2135

<400> SEQUENCE: 301
agaggucuug gggccgaaac                                                 20

<210> SEQ ID NO 302
<211> LENGTH: 22
<212> TYPE: RNA
<213> ORGANISM: Artificial Sequence
<220> FEATURE:
<223> OTHER INFORMATION: Synthetic: mmu-miR-216a

<400> SEQUENCE: 302
uaaucucagc uggcaacugu ga                                              22

<210> SEQ ID NO 303
<211> LENGTH: 21
<212> TYPE: RNA
<213> ORGANISM: Artificial Sequence
<220> FEATURE:
<223> OTHER INFORMATION: Synthetic: mmu-miR-743b-5p

<400> SEQUENCE: 303
uguucagacu ggguguccauc a                                              21

<210> SEQ ID NO 304
<211> LENGTH: 23
<212> TYPE: RNA
<213> ORGANISM: Artificial Sequence
<220> FEATURE:
<223> OTHER INFORMATION: Synthetic: mmu-miR-302b

<400> SEQUENCE: 304
uaagugcuuc cauguuuuag uag                                             23

<210> SEQ ID NO 305
<211> LENGTH: 23
```

```
<212> TYPE: RNA
<213> ORGANISM: Artificial Sequence
<220> FEATURE:
<223> OTHER INFORMATION: Synthetic: mmu-miR-667

<400> SEQUENCE: 305
ugacaccugc cacccagccc aag                                          23

<210> SEQ ID NO 306
<211> LENGTH: 22
<212> TYPE: RNA
<213> ORGANISM: Artificial Sequence
<220> FEATURE:
<223> OTHER INFORMATION: Synthetic: mmu-miR-330

<400> SEQUENCE: 306
ucucugggcc ugugucuuag gc                                           22

<210> SEQ ID NO 307
<211> LENGTH: 22
<212> TYPE: RNA
<213> ORGANISM: Artificial Sequence
<220> FEATURE:
<223> OTHER INFORMATION: Synthetic: mmu-miR-1948

<400> SEQUENCE: 307
uuuaggcaga gcacucguac ag                                           22

<210> SEQ ID NO 308
<211> LENGTH: 22
<212> TYPE: RNA
<213> ORGANISM: Artificial Sequence
<220> FEATURE:
<223> OTHER INFORMATION: Synthetic: mmu-miR-878-5p

<400> SEQUENCE: 308
uaucuaguug gaugucaaga ca                                           22

<210> SEQ ID NO 309
<211> LENGTH: 23
<212> TYPE: RNA
<213> ORGANISM: Artificial Sequence
<220> FEATURE:
<223> OTHER INFORMATION: Synthetic: mmu-miR-466a-3p

<400> SEQUENCE: 309
uauacauaca cgcacacaua aga                                          23

<210> SEQ ID NO 310
<211> LENGTH: 22
<212> TYPE: RNA
<213> ORGANISM: Artificial Sequence
<220> FEATURE:
<223> OTHER INFORMATION: Synthetic: mmu-miR-615-3p

<400> SEQUENCE: 310
uccgagccug ggucucccuc uu                                           22

<210> SEQ ID NO 311
<211> LENGTH: 22
<212> TYPE: RNA
<213> ORGANISM: Artificial Sequence
<220> FEATURE:
<223> OTHER INFORMATION: Synthetic: mmu-miR-129-3p

<400> SEQUENCE: 311
```

-continued

```
aagcccuuac cccaaaaagc au                                        22

<210> SEQ ID NO 312
<211> LENGTH: 24
<212> TYPE: RNA
<213> ORGANISM: Artificial Sequence
<220> FEATURE:
<223> OTHER INFORMATION: Synthetic: mmu-miR-2139

<400> SEQUENCE: 312
agcugcgcug cuccugguaa cugc                                      24

<210> SEQ ID NO 313
<211> LENGTH: 22
<212> TYPE: RNA
<213> ORGANISM: Artificial Sequence
<220> FEATURE:
<223> OTHER INFORMATION: Synthetic: mmu-miR-876-3p

<400> SEQUENCE: 313
uagugguuua caaaguaauu ca                                        22

<210> SEQ ID NO 314
<211> LENGTH: 22
<212> TYPE: RNA
<213> ORGANISM: Artificial Sequence
<220> FEATURE:
<223> OTHER INFORMATION: Synthetic: mmu-miR-875-5p

<400> SEQUENCE: 314
uauaccucag uuuuaucagg ug                                        22

<210> SEQ ID NO 315
<211> LENGTH: 16
<212> TYPE: RNA
<213> ORGANISM: Artificial Sequence
<220> FEATURE:
<223> OTHER INFORMATION: Synthetic: mmu-miR-546

<400> SEQUENCE: 315
augguggcac ggaguc                                               16

<210> SEQ ID NO 316
<211> LENGTH: 22
<212> TYPE: RNA
<213> ORGANISM: Artificial Sequence
<220> FEATURE:
<223> OTHER INFORMATION: Synthetic: mmu-miR-18a*

<400> SEQUENCE: 316
acugcccuaa gugcuccuuc ug                                        22

<210> SEQ ID NO 317
<211> LENGTH: 22
<212> TYPE: RNA
<213> ORGANISM: Artificial Sequence
<220> FEATURE:
<223> OTHER INFORMATION: Synthetic: mmu-miR-465b-5p

<400> SEQUENCE: 317
uauuuagaau ggugcugauc ug                                        22

<210> SEQ ID NO 318
<211> LENGTH: 22
<212> TYPE: RNA
<213> ORGANISM: Artificial Sequence
```

-continued

```
<220> FEATURE:
<223> OTHER INFORMATION: Synthetic: mmu-miR-184

<400> SEQUENCE: 318
uggacggaga acugauaagg gu                                                     22

<210> SEQ ID NO 319
<211> LENGTH: 22
<212> TYPE: RNA
<213> ORGANISM: Artificial Sequence
<220> FEATURE:
<223> OTHER INFORMATION: Synthetic: mmu-miR-1899

<400> SEQUENCE: 319
agcgauggcc gaaucugcuu cc                                                     22

<210> SEQ ID NO 320
<211> LENGTH: 21
<212> TYPE: RNA
<213> ORGANISM: Artificial Sequence
<220> FEATURE:
<223> OTHER INFORMATION: Synthetic: mmu-miR-1197

<400> SEQUENCE: 320
uaggacacau ggucuacuuc u                                                      21

<210> SEQ ID NO 321
<211> LENGTH: 22
<212> TYPE: RNA
<213> ORGANISM: Artificial Sequence
<220> FEATURE:
<223> OTHER INFORMATION: Synthetic: mmu-miR-743a

<400> SEQUENCE: 321
gaaagacacc aagcugagua ga                                                     22

<210> SEQ ID NO 322
<211> LENGTH: 22
<212> TYPE: RNA
<213> ORGANISM: Artificial Sequence
<220> FEATURE:
<223> OTHER INFORMATION: Synthetic: mmu-miR-200c*

<400> SEQUENCE: 322
cgucuuaccc agcaguguuu gg                                                     22

<210> SEQ ID NO 323
<211> LENGTH: 23
<212> TYPE: RNA
<213> ORGANISM: Artificial Sequence
<220> FEATURE:
<223> OTHER INFORMATION: Synthetic: mmu-miR-335-5p

<400> SEQUENCE: 323
ucaagagcaa uaacgaaaaa ugu                                                    23

<210> SEQ ID NO 324
<211> LENGTH: 24
<212> TYPE: RNA
<213> ORGANISM: Artificial Sequence
<220> FEATURE:
<223> OTHER INFORMATION: Synthetic: mmu-miR-1933-5p

<400> SEQUENCE: 324
agucauggug uucggucuua guuu                                                   24
```

-continued

<210> SEQ ID NO 325
<211> LENGTH: 23
<212> TYPE: RNA
<213> ORGANISM: Artificial Sequence
<220> FEATURE:
<223> OTHER INFORMATION: Synthetic: mmu-miR-1963

<400> SEQUENCE: 325
ugggacgaga ucaugaggcc uuc                                                23

<210> SEQ ID NO 326
<211> LENGTH: 23
<212> TYPE: RNA
<213> ORGANISM: Artificial Sequence
<220> FEATURE:
<223> OTHER INFORMATION: Synthetic: mmu-miR-384-5p

<400> SEQUENCE: 326
uguaaacaau uccuaggcaa ugu                                                23

<210> SEQ ID NO 327
<211> LENGTH: 22
<212> TYPE: RNA
<213> ORGANISM: Artificial Sequence
<220> FEATURE:
<223> OTHER INFORMATION: Synthetic: mmu-miR-695

<400> SEQUENCE: 327
agauugggca uaggugacug aa                                                 22

<210> SEQ ID NO 328
<211> LENGTH: 23
<212> TYPE: RNA
<213> ORGANISM: Artificial Sequence
<220> FEATURE:
<223> OTHER INFORMATION: Synthetic: mmu-miR-470

<400> SEQUENCE: 328
uucuuggacu ggcacuggug agu                                                23

<210> SEQ ID NO 329
<211> LENGTH: 22
<212> TYPE: RNA
<213> ORGANISM: Artificial Sequence
<220> FEATURE:
<223> OTHER INFORMATION: Synthetic: mmu-miR-302a*

<400> SEQUENCE: 329
acuuaaacgu gguuguacuu gc                                                 22

<210> SEQ ID NO 330
<211> LENGTH: 22
<212> TYPE: RNA
<213> ORGANISM: Artificial Sequence
<220> FEATURE:
<223> OTHER INFORMATION: Synthetic: mmu-miR-28*

<400> SEQUENCE: 330
cacuagauug ugagcugcug ga                                                 22

<210> SEQ ID NO 331
<211> LENGTH: 21
<212> TYPE: RNA
<213> ORGANISM: Artificial Sequence
<220> FEATURE:
<223> OTHER INFORMATION: Synthetic: mmu-miR-224

-continued

<400> SEQUENCE: 331
uaagucacua gugguuccgu u                                                    21

<210> SEQ ID NO 332
<211> LENGTH: 25
<212> TYPE: RNA
<213> ORGANISM: Artificial Sequence
<220> FEATURE:
<223> OTHER INFORMATION: Synthetic: mmu-miR-1966

<400> SEQUENCE: 332
aagggagcug gcucaggaga gaguc                                                25

<210> SEQ ID NO 333
<211> LENGTH: 22
<212> TYPE: RNA
<213> ORGANISM: Artificial Sequence
<220> FEATURE:
<223> OTHER INFORMATION: Synthetic: mmu-miR-181a-2*

<400> SEQUENCE: 333
accgaccguu gacuguaccu ug                                                   22

<210> SEQ ID NO 334
<211> LENGTH: 23
<212> TYPE: RNA
<213> ORGANISM: Artificial Sequence
<220> FEATURE:
<223> OTHER INFORMATION: Synthetic: mmu-miR-1969

<400> SEQUENCE: 334
aagauggaga cuuuaacaug ggu                                                  23

<210> SEQ ID NO 335
<211> LENGTH: 22
<212> TYPE: RNA
<213> ORGANISM: Artificial Sequence
<220> FEATURE:
<223> OTHER INFORMATION: Synthetic: mmu-miR-291a-3p

<400> SEQUENCE: 335
aaagugcuuc cacuuugugu gc                                                   22

<210> SEQ ID NO 336
<211> LENGTH: 22
<212> TYPE: RNA
<213> ORGANISM: Artificial Sequence
<220> FEATURE:
<223> OTHER INFORMATION: Synthetic: mmu-miR-374*

<400> SEQUENCE: 336
gguuguauua ucauuguccg ag                                                   22

<210> SEQ ID NO 337
<211> LENGTH: 22
<212> TYPE: RNA
<213> ORGANISM: Artificial Sequence
<220> FEATURE:
<223> OTHER INFORMATION: Synthetic: mmu-miR-881*

<400> SEQUENCE: 337
cagagagaua acagucacau cu                                                   22

<210> SEQ ID NO 338

-continued

```
<211> LENGTH: 23
<212> TYPE: RNA
<213> ORGANISM: Artificial Sequence
<220> FEATURE:
<223> OTHER INFORMATION: Synthetic: mmu-miR-135b

<400> SEQUENCE: 338
uauggcuuuu cauuccuaug uga                                           23

<210> SEQ ID NO 339
<211> LENGTH: 22
<212> TYPE: RNA
<213> ORGANISM: Artificial Sequence
<220> FEATURE:
<223> OTHER INFORMATION: Synthetic: mmu-miR-666-3p

<400> SEQUENCE: 339
ggcugcagcg ugaucgccug cu                                            22

<210> SEQ ID NO 340
<211> LENGTH: 22
<212> TYPE: RNA
<213> ORGANISM: Artificial Sequence
<220> FEATURE:
<223> OTHER INFORMATION: Synthetic: mmu-miR-136*

<400> SEQUENCE: 340
aucaucgucu caaaugaguc uu                                            22

<210> SEQ ID NO 341
<211> LENGTH: 22
<212> TYPE: RNA
<213> ORGANISM: Artificial Sequence
<220> FEATURE:
<223> OTHER INFORMATION: Synthetic: mmu-miR-1947

<400> SEQUENCE: 341
aggacgagcu agcugagugc ug                                            22

<210> SEQ ID NO 342
<211> LENGTH: 22
<212> TYPE: RNA
<213> ORGANISM: Artificial Sequence
<220> FEATURE:
<223> OTHER INFORMATION: Synthetic: mmu-miR-883a-5p

<400> SEQUENCE: 342
ugcugagaga aguagcaguu ac                                            22

<210> SEQ ID NO 343
<211> LENGTH: 22
<212> TYPE: RNA
<213> ORGANISM: Artificial Sequence
<220> FEATURE:
<223> OTHER INFORMATION: Synthetic: mmu-miR-130b*

<400> SEQUENCE: 343
acucuuuccc uguugcacua cu                                            22

<210> SEQ ID NO 344
<211> LENGTH: 22
<212> TYPE: RNA
<213> ORGANISM: Artificial Sequence
<220> FEATURE:
<223> OTHER INFORMATION: Synthetic: mmu-miR-431*

<400> SEQUENCE: 344
```
caggucgucu ugcagggcuu cu                                      22

<210> SEQ ID NO 345
<211> LENGTH: 22
<212> TYPE: RNA
<213> ORGANISM: Artificial Sequence
<220> FEATURE:
<223> OTHER INFORMATION: Synthetic: mmu-miR-21*

<400> SEQUENCE: 345
caacagcagu cgaugggcug uc                                      22

<210> SEQ ID NO 346
<211> LENGTH: 21
<212> TYPE: RNA
<213> ORGANISM: Artificial Sequence
<220> FEATURE:
<223> OTHER INFORMATION: Synthetic: mmu-miR-1-2-as

<400> SEQUENCE: 346
uacauacuuc uuuacauucc a                                       21

<210> SEQ ID NO 347
<211> LENGTH: 21
<212> TYPE: RNA
<213> ORGANISM: Artificial Sequence
<220> FEATURE:
<223> OTHER INFORMATION: Synthetic: mmu-miR-1954

<400> SEQUENCE: 347
acugcagagu gagacccugu u                                       21

<210> SEQ ID NO 348
<211> LENGTH: 22
<212> TYPE: RNA
<213> ORGANISM: Artificial Sequence
<220> FEATURE:
<223> OTHER INFORMATION: Synthetic: mmu-miR-15a*

<400> SEQUENCE: 348
caggccauac ugugcugccu ca                                      22

<210> SEQ ID NO 349
<211> LENGTH: 23
<212> TYPE: RNA
<213> ORGANISM: Artificial Sequence
<220> FEATURE:
<223> OTHER INFORMATION: Synthetic: mmu-miR-135a

<400> SEQUENCE: 349
uauggcuuuu uauuccuaug uga                                     23

<210> SEQ ID NO 350
<211> LENGTH: 19
<212> TYPE: RNA
<213> ORGANISM: Artificial Sequence
<220> FEATURE:
<223> OTHER INFORMATION: Synthetic: mmu-miR-2134

<400> SEQUENCE: 350
gucuugggaa acgggugc                                           19

<210> SEQ ID NO 351
<211> LENGTH: 22
<212> TYPE: RNA

-continued

```
<213> ORGANISM: Artificial Sequence
<220> FEATURE:
<223> OTHER INFORMATION: Synthetic: mmu-miR-465a-3p

<400> SEQUENCE: 351
gaucagggcc uuucuaagua ga                                      22

<210> SEQ ID NO 352
<211> LENGTH: 21
<212> TYPE: RNA
<213> ORGANISM: Artificial Sequence
<220> FEATURE:
<223> OTHER INFORMATION: Synthetic: mmu-miR-742*

<400> SEQUENCE: 352
uacucacaug guugcuaauc a                                       21

<210> SEQ ID NO 353
<211> LENGTH: 21
<212> TYPE: RNA
<213> ORGANISM: Artificial Sequence
<220> FEATURE:
<223> OTHER INFORMATION: Synthetic: mmu-miR-671-3p

<400> SEQUENCE: 353
uccgguucuc agggcuccac c                                       21

<210> SEQ ID NO 354
<211> LENGTH: 22
<212> TYPE: RNA
<213> ORGANISM: Artificial Sequence
<220> FEATURE:
<223> OTHER INFORMATION: Synthetic: mmu-miR-186*

<400> SEQUENCE: 354
gcccuaaggu gaauuuuuug gg                                      22

<210> SEQ ID NO 355
<211> LENGTH: 23
<212> TYPE: RNA
<213> ORGANISM: Artificial Sequence
<220> FEATURE:
<223> OTHER INFORMATION: Synthetic: mmu-miR-409-5p

<400> SEQUENCE: 355
agguuacccg agcaacuuug cau                                     23

<210> SEQ ID NO 356
<211> LENGTH: 22
<212> TYPE: RNA
<213> ORGANISM: Artificial Sequence
<220> FEATURE:
<223> OTHER INFORMATION: Synthetic: mmu-miR-878-3p

<400> SEQUENCE: 356
gcaugacacc acacugggua ga                                      22

<210> SEQ ID NO 357
<211> LENGTH: 22
<212> TYPE: RNA
<213> ORGANISM: Artificial Sequence
<220> FEATURE:
<223> OTHER INFORMATION: Synthetic: mmu-miR-409-3p

<400> SEQUENCE: 357
gaauguugcu cggugaaccc cu                                      22
```

-continued

```
<210> SEQ ID NO 358
<211> LENGTH: 22
<212> TYPE: RNA
<213> ORGANISM: Artificial Sequence
<220> FEATURE:
<223> OTHER INFORMATION: Synthetic: mmu-miR-145*

<400> SEQUENCE: 358
auuccuggaa auacuguucu ug                                              22

<210> SEQ ID NO 359
<211> LENGTH: 22
<212> TYPE: RNA
<213> ORGANISM: Artificial Sequence
<220> FEATURE:
<223> OTHER INFORMATION: Synthetic: mmu-miR-448

<400> SEQUENCE: 359
uugcauaugu aggauguccc au                                              22

<210> SEQ ID NO 360
<211> LENGTH: 22
<212> TYPE: RNA
<213> ORGANISM: Artificial Sequence
<220> FEATURE:
<223> OTHER INFORMATION: Synthetic: mmu-miR-880

<400> SEQUENCE: 360
uacuccaucc ucucugagua ga                                              22

<210> SEQ ID NO 361
<211> LENGTH: 22
<212> TYPE: RNA
<213> ORGANISM: Artificial Sequence
<220> FEATURE:
<223> OTHER INFORMATION: Synthetic: mmu-miR-26b*

<400> SEQUENCE: 361
ccuguucucc auuacuuggc uc                                              22

<210> SEQ ID NO 362
<211> LENGTH: 22
<212> TYPE: RNA
<213> ORGANISM: Artificial Sequence
<220> FEATURE:
<223> OTHER INFORMATION: Synthetic: mmu-miR-99b*

<400> SEQUENCE: 362
caagcucgug ucuguggguc cg                                              22

<210> SEQ ID NO 363
<211> LENGTH: 22
<212> TYPE: RNA
<213> ORGANISM: Artificial Sequence
<220> FEATURE:
<223> OTHER INFORMATION: Synthetic: mmu-miR-1960

<400> SEQUENCE: 363
ccagugcugu uagaagaggg cu                                              22

<210> SEQ ID NO 364
<211> LENGTH: 22
<212> TYPE: RNA
<213> ORGANISM: Artificial Sequence
<220> FEATURE:
```

-continued

<223> OTHER INFORMATION: Synthetic: mmu-miR-214*

<400> SEQUENCE: 364
ugccugucua cacuugcugu gc                                              22

<210> SEQ ID NO 365
<211> LENGTH: 22
<212> TYPE: RNA
<213> ORGANISM: Artificial Sequence
<220> FEATURE:
<223> OTHER INFORMATION: Synthetic: mmu-miR-196a*

<400> SEQUENCE: 365
ucggcaacaa gaaacugccu ga                                              22

<210> SEQ ID NO 366
<211> LENGTH: 22
<212> TYPE: RNA
<213> ORGANISM: Artificial Sequence
<220> FEATURE:
<223> OTHER INFORMATION: Synthetic: mmu-let-7f*

<400> SEQUENCE: 366
cuauacaauc uauugccuuc cc                                              22

<210> SEQ ID NO 367
<211> LENGTH: 22
<212> TYPE: RNA
<213> ORGANISM: Artificial Sequence
<220> FEATURE:
<223> OTHER INFORMATION: Synthetic: mmu-miR-465c-3p

<400> SEQUENCE: 367
gaucagggcc uuucuaagua ga                                              22

<210> SEQ ID NO 368
<211> LENGTH: 22
<212> TYPE: RNA
<213> ORGANISM: Artificial Sequence
<220> FEATURE:
<223> OTHER INFORMATION: Synthetic: mmu-miR-467a*

<400> SEQUENCE: 368
auauacauac acacaccuac ac                                              22

<210> SEQ ID NO 369
<211> LENGTH: 22
<212> TYPE: RNA
<213> ORGANISM: Artificial Sequence
<220> FEATURE:
<223> OTHER INFORMATION: Synthetic: mmu-miR-1896

<400> SEQUENCE: 369
cucucugaug gugggugagg ag                                              22

<210> SEQ ID NO 370
<211> LENGTH: 22
<212> TYPE: RNA
<213> ORGANISM: Artificial Sequence
<220> FEATURE:
<223> OTHER INFORMATION: Synthetic: mmu-miR-802

<400> SEQUENCE: 370
ucaguaacaa agauucaucc uu                                              22

-continued

<210> SEQ ID NO 371
<211> LENGTH: 22
<212> TYPE: RNA
<213> ORGANISM: Artificial Sequence
<220> FEATURE:
<223> OTHER INFORMATION: Synthetic: mmu-miR-433*

<400> SEQUENCE: 371
uacggugagc cgucauuau uc                                                    22

<210> SEQ ID NO 372
<211> LENGTH: 22
<212> TYPE: RNA
<213> ORGANISM: Artificial Sequence
<220> FEATURE:
<223> OTHER INFORMATION: Synthetic: mmu-miR-463*

<400> SEQUENCE: 372
uaccuaauuu guuguccauc au                                                   22

<210> SEQ ID NO 373
<211> LENGTH: 22
<212> TYPE: RNA
<213> ORGANISM: Artificial Sequence
<220> FEATURE:
<223> OTHER INFORMATION: Synthetic: mmu-miR-294

<400> SEQUENCE: 373
aaagugcuuc ccuuuugugu gu                                                   22

<210> SEQ ID NO 374
<211> LENGTH: 22
<212> TYPE: RNA
<213> ORGANISM: Artificial Sequence
<220> FEATURE:
<223> OTHER INFORMATION: Synthetic: mmu-miR-124*

<400> SEQUENCE: 374
cguguucaca gcggaccuug au                                                   22

<210> SEQ ID NO 375
<211> LENGTH: 23
<212> TYPE: RNA
<213> ORGANISM: Artificial Sequence
<220> FEATURE:
<223> OTHER INFORMATION: Synthetic: mmu-miR-142-3p

<400> SEQUENCE: 375
uguaguguuu ccuacuuuau gga                                                  23

<210> SEQ ID NO 376
<211> LENGTH: 21
<212> TYPE: RNA
<213> ORGANISM: Artificial Sequence
<220> FEATURE:
<223> OTHER INFORMATION: Synthetic: mmu-miR-488*

<400> SEQUENCE: 376
cccagauaau agcacucuca a                                                    21

<210> SEQ ID NO 377
<211> LENGTH: 22
<212> TYPE: RNA
<213> ORGANISM: Artificial Sequence
<220> FEATURE:
<223> OTHER INFORMATION: Synthetic: mmu-miR-376b*

-continued

```
<400> SEQUENCE: 377
guggauauuc cuucuauggu ua                                                    22

<210> SEQ ID NO 378
<211> LENGTH: 20
<212> TYPE: RNA
<213> ORGANISM: Artificial Sequence
<220> FEATURE:
<223> OTHER INFORMATION: Synthetic: mmu-miR-1959

<400> SEQUENCE: 378
ggggauguag cucaguggag                                                       20

<210> SEQ ID NO 379
<211> LENGTH: 22
<212> TYPE: RNA
<213> ORGANISM: Artificial Sequence
<220> FEATURE:
<223> OTHER INFORMATION: Synthetic: mmu-miR-216b

<400> SEQUENCE: 379
aaaucucugc aggcaaaugu ga                                                    22

<210> SEQ ID NO 380
<211> LENGTH: 22
<212> TYPE: RNA
<213> ORGANISM: Artificial Sequence
<220> FEATURE:
<223> OTHER INFORMATION: Synthetic: mmu-let-7b*

<400> SEQUENCE: 380
cuauacaacc uacugccuuc cc                                                    22

<210> SEQ ID NO 381
<211> LENGTH: 22
<212> TYPE: RNA
<213> ORGANISM: Artificial Sequence
<220> FEATURE:
<223> OTHER INFORMATION: Synthetic: mmu-miR-297a*

<400> SEQUENCE: 381
uauacauaca cacauaccca ua                                                    22

<210> SEQ ID NO 382
<211> LENGTH: 22
<212> TYPE: RNA
<213> ORGANISM: Artificial Sequence
<220> FEATURE:
<223> OTHER INFORMATION: Synthetic: mmu-miR-670

<400> SEQUENCE: 382
aucccugagu guauguggug aa                                                    22

<210> SEQ ID NO 383
<211> LENGTH: 23
<212> TYPE: RNA
<213> ORGANISM: Artificial Sequence
<220> FEATURE:
<223> OTHER INFORMATION: Synthetic: mmu-miR-7b

<400> SEQUENCE: 383
uggaagacuu gugauuuugu ugu                                                   23

<210> SEQ ID NO 384
<211> LENGTH: 19
```

-continued

```
<212> TYPE: RNA
<213> ORGANISM: Artificial Sequence
<220> FEATURE:
<223> OTHER INFORMATION: Synthetic: mmu-miR-599

<400> SEQUENCE: 384
uugugucagu uuaucaaac                                         19

<210> SEQ ID NO 385
<211> LENGTH: 22
<212> TYPE: RNA
<213> ORGANISM: Artificial Sequence
<220> FEATURE:
<223> OTHER INFORMATION: Synthetic: mmu-miR-10a*

<400> SEQUENCE: 385
caaauucgua ucuaggggaa ua                                     22

<210> SEQ ID NO 386
<211> LENGTH: 22
<212> TYPE: RNA
<213> ORGANISM: Artificial Sequence
<220> FEATURE:
<223> OTHER INFORMATION: Synthetic: mmu-miR-669m

<400> SEQUENCE: 386
auauacaucc acacaaacau au                                     22

<210> SEQ ID NO 387
<211> LENGTH: 22
<212> TYPE: RNA
<213> ORGANISM: Artificial Sequence
<220> FEATURE:
<223> OTHER INFORMATION: Synthetic: mmu-miR-300*

<400> SEQUENCE: 387
uugaagagag guuauccuuu gu                                     22

<210> SEQ ID NO 388
<211> LENGTH: 23
<212> TYPE: RNA
<213> ORGANISM: Artificial Sequence
<220> FEATURE:
<223> OTHER INFORMATION: Synthetic: mmu-miR-138

<400> SEQUENCE: 388
agcugguguu gugaaucagg ccg                                    23

<210> SEQ ID NO 389
<211> LENGTH: 22
<212> TYPE: RNA
<213> ORGANISM: Artificial Sequence
<220> FEATURE:
<223> OTHER INFORMATION: Synthetic: mmu-miR-320

<400> SEQUENCE: 389
aaaagcuggg uugagagggc ga                                     22

<210> SEQ ID NO 390
<211> LENGTH: 22
<212> TYPE: RNA
<213> ORGANISM: Artificial Sequence
<220> FEATURE:
<223> OTHER INFORMATION: Synthetic: mmu-miR-744

<400> SEQUENCE: 390
```

-continued ugcggggcua gggcuaacag ca                                          22

<210> SEQ ID NO 391
<211> LENGTH: 22
<212> TYPE: RNA
<213> ORGANISM: Artificial Sequence
<220> FEATURE:
<223> OTHER INFORMATION: Synthetic: mmu-miR-717

<400> SEQUENCE: 391
cucagacaga gauaccuucu cu                                          22

<210> SEQ ID NO 392
<211> LENGTH: 22
<212> TYPE: RNA
<213> ORGANISM: Artificial Sequence
<220> FEATURE:
<223> OTHER INFORMATION: Synthetic: mmu-miR-297c*

<400> SEQUENCE: 392
uauacauaca cacauaccca ua                                          22

<210> SEQ ID NO 393
<211> LENGTH: 22
<212> TYPE: RNA
<213> ORGANISM: Artificial Sequence
<220> FEATURE:
<223> OTHER INFORMATION: Synthetic: mmu-miR-223

<400> SEQUENCE: 393
ugucaguuug ucaaauaccc ca                                          22

<210> SEQ ID NO 394
<211> LENGTH: 22
<212> TYPE: RNA
<213> ORGANISM: Artificial Sequence
<220> FEATURE:
<223> OTHER INFORMATION: Synthetic: mmu-miR-675-3p

<400> SEQUENCE: 394
cuguaugccc uaaccgcuca gu                                          22

<210> SEQ ID NO 395
<211> LENGTH: 23
<212> TYPE: RNA
<213> ORGANISM: Artificial Sequence
<220> FEATURE:
<223> OTHER INFORMATION: Synthetic: mmu-miR-7a

<400> SEQUENCE: 395
uggaagacua gugauuuugu ugu                                         23

<210> SEQ ID NO 396
<211> LENGTH: 22
<212> TYPE: RNA
<213> ORGANISM: Artificial Sequence
<220> FEATURE:
<223> OTHER INFORMATION: Synthetic: mmu-miR-879*

<400> SEQUENCE: 396
gcuuauggcu ucaagcuuuc gg                                          22

<210> SEQ ID NO 397
<211> LENGTH: 22
<212> TYPE: RNA
<213> ORGANISM: Artificial Sequence -continued

```
<220> FEATURE:
<223> OTHER INFORMATION: Synthetic: mmu-miR-146b*

<400> SEQUENCE: 397
gcccuaggga cucaguucug gu                                                  22

<210> SEQ ID NO 398
<211> LENGTH: 24
<212> TYPE: RNA
<213> ORGANISM: Artificial Sequence
<220> FEATURE:
<223> OTHER INFORMATION: Synthetic: mmu-miR-351

<400> SEQUENCE: 398
ucccugagga gcccuuugag ccug                                                24

<210> SEQ ID NO 399
<211> LENGTH: 22
<212> TYPE: RNA
<213> ORGANISM: Artificial Sequence
<220> FEATURE:
<223> OTHER INFORMATION: Synthetic: mmu-miR-32

<400> SEQUENCE: 399
uauugcacau uacuaaguug ca                                                  22

<210> SEQ ID NO 400
<211> LENGTH: 22
<212> TYPE: RNA
<213> ORGANISM: Artificial Sequence
<220> FEATURE:
<223> OTHER INFORMATION: Synthetic: mmu-miR-293

<400> SEQUENCE: 400
agugccgcag aguuuguagu gu                                                  22

<210> SEQ ID NO 401
<211> LENGTH: 22
<212> TYPE: RNA
<213> ORGANISM: Artificial Sequence
<220> FEATURE:
<223> OTHER INFORMATION: Synthetic: mmu-miR-501-5p

<400> SEQUENCE: 401
aauccuuugu cccuggguga aa                                                  22

<210> SEQ ID NO 402
<211> LENGTH: 22
<212> TYPE: RNA
<213> ORGANISM: Artificial Sequence
<220> FEATURE:
<223> OTHER INFORMATION: Synthetic: mmu-miR-883a-3p

<400> SEQUENCE: 402
uaacugcaac agcucucagu au                                                  22

<210> SEQ ID NO 403
<211> LENGTH: 22
<212> TYPE: RNA
<213> ORGANISM: Artificial Sequence
<220> FEATURE:
<223> OTHER INFORMATION: Synthetic: mmu-miR-719

<400> SEQUENCE: 403
aucucggcua cagaaaaaug uu                                                  22
```

-continued

```
<210> SEQ ID NO 404
<211> LENGTH: 22
<212> TYPE: RNA
<213> ORGANISM: Artificial Sequence
<220> FEATURE:
<223> OTHER INFORMATION: Synthetic: mmu-miR-186

<400> SEQUENCE: 404
caaagaauuc uccuuuuggg cu                                                    22

<210> SEQ ID NO 405
<211> LENGTH: 22
<212> TYPE: RNA
<213> ORGANISM: Artificial Sequence
<220> FEATURE:
<223> OTHER INFORMATION: Synthetic: mmu-miR-197

<400> SEQUENCE: 405
uucaccaccu ucuccaccca gc                                                    22

<210> SEQ ID NO 406
<211> LENGTH: 23
<212> TYPE: RNA
<213> ORGANISM: Artificial Sequence
<220> FEATURE:
<223> OTHER INFORMATION: Synthetic: mmu-miR-199a-5p

<400> SEQUENCE: 406
cccaguguuc agacuaccug uuc                                                   23

<210> SEQ ID NO 407
<211> LENGTH: 22
<212> TYPE: RNA
<213> ORGANISM: Artificial Sequence
<220> FEATURE:
<223> OTHER INFORMATION: Synthetic: mmu-miR-200a

<400> SEQUENCE: 407
uaacacuguc ugguaacgau gu                                                    22

<210> SEQ ID NO 408
<211> LENGTH: 23
<212> TYPE: RNA
<213> ORGANISM: Artificial Sequence
<220> FEATURE:
<223> OTHER INFORMATION: Synthetic: mmu-miR-200c

<400> SEQUENCE: 408
uaauacugcc ggguaaugau gga                                                   23

<210> SEQ ID NO 409
<211> LENGTH: 22
<212> TYPE: RNA
<213> ORGANISM: Artificial Sequence
<220> FEATURE:
<223> OTHER INFORMATION: Synthetic: mmu-miR-202-3p

<400> SEQUENCE: 409
agagguauag cgcaugggaa ga                                                    22

<210> SEQ ID NO 410
<211> LENGTH: 21
<212> TYPE: RNA
<213> ORGANISM: Artificial Sequence
<220> FEATURE:
<223> OTHER INFORMATION: Synthetic: mmu-miR-202-5p
```

-continued

<400> SEQUENCE: 410
uuccuaugca uauacuucuu u                                                    21

<210> SEQ ID NO 411
<211> LENGTH: 22
<212> TYPE: RNA
<213> ORGANISM: Artificial Sequence
<220> FEATURE:
<223> OTHER INFORMATION: Synthetic: mmu-miR-203

<400> SEQUENCE: 411
gugaaauguu uaggaccacu ag                                                   22

<210> SEQ ID NO 412
<211> LENGTH: 21
<212> TYPE: RNA
<213> ORGANISM: Artificial Sequence
<220> FEATURE:
<223> OTHER INFORMATION: Synthetic: mmu-miR-296-5p

<400> SEQUENCE: 412
agggcccccc cucaauccug u                                                    21

<210> SEQ ID NO 413
<211> LENGTH: 23
<212> TYPE: RNA
<213> ORGANISM: Artificial Sequence
<220> FEATURE:
<223> OTHER INFORMATION: Synthetic: mmu-miR-339-3p

<400> SEQUENCE: 413
ugagcgccuc ggcgacagag ccg                                                  23

<210> SEQ ID NO 414
<211> LENGTH: 22
<212> TYPE: RNA
<213> ORGANISM: Artificial Sequence
<220> FEATURE:
<223> OTHER INFORMATION: Synthetic: mmu-miR-463

<400> SEQUENCE: 414
ugauagacac cauauaaggu ag                                                   22

<210> SEQ ID NO 415
<211> LENGTH: 20
<212> TYPE: RNA
<213> ORGANISM: Artificial Sequence
<220> FEATURE:
<223> OTHER INFORMATION: Synthetic: mmu-miR-688

<400> SEQUENCE: 415
ucgcaggcga cuacuuauuc                                                      20

<210> SEQ ID NO 416
<211> LENGTH: 22
<212> TYPE: RNA
<213> ORGANISM: Artificial Sequence
<220> FEATURE:
<223> OTHER INFORMATION: Synthetic: mmu-miR-759

<400> SEQUENCE: 416
gcagagugca aacaauuuug ac                                                   22

<210> SEQ ID NO 417

-continued

```
<211> LENGTH: 22
<212> TYPE: RNA
<213> ORGANISM: Artificial Sequence
<220> FEATURE:
<223> OTHER INFORMATION: Synthetic: mmu-miR-762

<400> SEQUENCE: 417 gggcugggg ccgggacaga gc                                           22

<210> SEQ ID NO 418
<211> LENGTH: 22
<212> TYPE: RNA
<213> ORGANISM: Artificial Sequence
<220> FEATURE:
<223> OTHER INFORMATION: Synthetic: mmu-miR-291b-5p

<400> SEQUENCE: 418
gaucaaagug gaggcccucu cc                                          22

<210> SEQ ID NO 419
<211> LENGTH: 22
<212> TYPE: RNA
<213> ORGANISM: Artificial Sequence
<220> FEATURE:
<223> OTHER INFORMATION: Synthetic: mmu-miR-299*

<400> SEQUENCE: 419
ugguuuaccg ucccacauac au                                          22

<210> SEQ ID NO 420
<211> LENGTH: 22
<212> TYPE: RNA
<213> ORGANISM: Artificial Sequence
<220> FEATURE:
<223> OTHER INFORMATION: Synthetic: mmu-miR-532-3p

<400> SEQUENCE: 420
ccucccacac ccaaggcuug ca                                          22

<210> SEQ ID NO 421
<211> LENGTH: 22
<212> TYPE: RNA
<213> ORGANISM: Artificial Sequence
<220> FEATURE:
<223> OTHER INFORMATION: Synthetic: mmu-miR-191*

<400> SEQUENCE: 421
gcugcacuug gauuucguuc cc                                          22

<210> SEQ ID NO 422
<211> LENGTH: 22
<212> TYPE: RNA
<213> ORGANISM: Artificial Sequence
<220> FEATURE:
<223> OTHER INFORMATION: Synthetic: mmu-miR-132

<400> SEQUENCE: 422
uaacagucua cagccauggu cg                                          22

<210> SEQ ID NO 423
<211> LENGTH: 22
<212> TYPE: RNA
<213> ORGANISM: Artificial Sequence
<220> FEATURE:
<223> OTHER INFORMATION: Synthetic: mmu-miR-872*

<400> SEQUENCE: 423
```

-continued ugaacuauug caguagccuc cu                                            22

<210> SEQ ID NO 424
<211> LENGTH: 22
<212> TYPE: RNA
<213> ORGANISM: Artificial Sequence
<220> FEATURE:
<223> OTHER INFORMATION: Synthetic: mmu-miR-200b

<400> SEQUENCE: 424
uaauacugcc ugguaaugau ga                                           22

<210> SEQ ID NO 425
<211> LENGTH: 21
<212> TYPE: RNA
<213> ORGANISM: Artificial Sequence
<220> FEATURE:
<223> OTHER INFORMATION: Synthetic: mmu-miR-1193

<400> SEQUENCE: 425
uaggucaccc guuuuacuau c                                            21

<210> SEQ ID NO 426
<211> LENGTH: 21
<212> TYPE: RNA
<213> ORGANISM: Artificial Sequence
<220> FEATURE:
<223> OTHER INFORMATION: Synthetic: mmu-miR-714

<400> SEQUENCE: 426
cgacgagggc cggucggucg c                                            21

<210> SEQ ID NO 427
<211> LENGTH: 22
<212> TYPE: RNA
<213> ORGANISM: Artificial Sequence
<220> FEATURE:
<223> OTHER INFORMATION: Synthetic: mmu-miR-691

<400> SEQUENCE: 427
auuccugaag agaggcagaa aa                                           22

<210> SEQ ID NO 428
<211> LENGTH: 22
<212> TYPE: RNA
<213> ORGANISM: Artificial Sequence
<220> FEATURE:
<223> OTHER INFORMATION: Synthetic: mmu-miR-369-5p

<400> SEQUENCE: 428
agaucgaccg uguuauauuc gc                                           22

<210> SEQ ID NO 429
<211> LENGTH: 21
<212> TYPE: RNA
<213> ORGANISM: Artificial Sequence
<220> FEATURE:
<223> OTHER INFORMATION: Synthetic: mmu-miR-425*

<400> SEQUENCE: 429
aucgggaaug ucguguccgc c                                            21

<210> SEQ ID NO 430
<211> LENGTH: 22
<212> TYPE: RNA

-continued

<213> ORGANISM: Artificial Sequence
<220> FEATURE:
<223> OTHER INFORMATION: Synthetic: mmu-miR-654-3p

<400> SEQUENCE: 430
uaugucugcu gaccaucacc uu                                                                                    22

<210> SEQ ID NO 431
<211> LENGTH: 21
<212> TYPE: RNA
<213> ORGANISM: Artificial Sequence
<220> FEATURE:
<223> OTHER INFORMATION: Synthetic: mmu-miR-700

<400> SEQUENCE: 431
cacgcgggaa ccgaguccac c                                                                                     21

<210> SEQ ID NO 432
<211> LENGTH: 22
<212> TYPE: RNA
<213> ORGANISM: Artificial Sequence
<220> FEATURE:
<223> OTHER INFORMATION: Synthetic: mmu-miR-1964

<400> SEQUENCE: 432
ccgacuucug ggcuccggcu uu                                                                                    22

<210> SEQ ID NO 433
<211> LENGTH: 22
<212> TYPE: RNA
<213> ORGANISM: Artificial Sequence
<220> FEATURE:
<223> OTHER INFORMATION: Synthetic: mmu-miR-376a*

<400> SEQUENCE: 433
gguagauucu ccuucuauga gu                                                                                    22

<210> SEQ ID NO 434
<211> LENGTH: 22
<212> TYPE: RNA
<213> ORGANISM: Artificial Sequence
<220> FEATURE:
<223> OTHER INFORMATION: Synthetic: mmu-miR-598

<400> SEQUENCE: 434
uacgucaucg ucgucaucgu ua                                                                                    22

<210> SEQ ID NO 435
<211> LENGTH: 21
<212> TYPE: RNA
<213> ORGANISM: Artificial Sequence
<220> FEATURE:
<223> OTHER INFORMATION: Synthetic: mmu-miR-369-3p

<400> SEQUENCE: 435
aauaauacau gguugaucuu u                                                                                     21

<210> SEQ ID NO 436
<211> LENGTH: 22
<212> TYPE: RNA
<213> ORGANISM: Artificial Sequence
<220> FEATURE:
<223> OTHER INFORMATION: Synthetic: mmu-miR-654-5p

<400> SEQUENCE: 436
ugguaagcug cagaacaugu gu                                                                                    22

-continued

<210> SEQ ID NO 437
<211> LENGTH: 21
<212> TYPE: RNA
<213> ORGANISM: Artificial Sequence
<220> FEATURE:
<223> OTHER INFORMATION: Synthetic: mmu-miR-129-5p

<400> SEQUENCE: 437
cuuuuugcgg ucugggcuug c                                                             21

<210> SEQ ID NO 438
<211> LENGTH: 22
<212> TYPE: RNA
<213> ORGANISM: Artificial Sequence
<220> FEATURE:
<223> OTHER INFORMATION: Synthetic: mmu-let-7i*

<400> SEQUENCE: 438
cugcgcaagc uacugccuug cu                                                            22

<210> SEQ ID NO 439
<211> LENGTH: 22
<212> TYPE: RNA
<213> ORGANISM: Artificial Sequence
<220> FEATURE:
<223> OTHER INFORMATION: Synthetic: mmu-miR-125b*

<400> SEQUENCE: 439
acaagucagg uucuugggac cu                                                            22

<210> SEQ ID NO 440
<211> LENGTH: 22
<212> TYPE: RNA
<213> ORGANISM: Artificial Sequence
<220> FEATURE:
<223> OTHER INFORMATION: Synthetic: mmu-miR-669h-3p

<400> SEQUENCE: 440
uaugcauaua cacacaugca ca                                                            22

<210> SEQ ID NO 441
<211> LENGTH: 22
<212> TYPE: RNA
<213> ORGANISM: Artificial Sequence
<220> FEATURE:
<223> OTHER INFORMATION: Synthetic: mmu-miR-1

<400> SEQUENCE: 441
uggaauguaa agaaguaugu au                                                            22

<210> SEQ ID NO 442
<211> LENGTH: 21
<212> TYPE: RNA
<213> ORGANISM: Artificial Sequence
<220> FEATURE:
<223> OTHER INFORMATION: Synthetic: mmu-miR-1942

<400> SEQUENCE: 442
ucagaugucu ucaucugguu g                                                             21

<210> SEQ ID NO 443
<211> LENGTH: 24
<212> TYPE: RNA
<213> ORGANISM: Artificial Sequence
<220> FEATURE:

-continued

<223> OTHER INFORMATION: Synthetic: mmu-miR-669h-5p

<400> SEQUENCE: 443
augcaugggu guauaguuga gugc                                    24

<210> SEQ ID NO 444
<211> LENGTH: 21
<212> TYPE: RNA
<213> ORGANISM: Artificial Sequence
<220> FEATURE:
<223> OTHER INFORMATION: Synthetic: mmu-miR-1191

<400> SEQUENCE: 444
cagucuuacu auguagcccu a                                       21

<210> SEQ ID NO 445
<211> LENGTH: 21
<212> TYPE: RNA
<213> ORGANISM: Artificial Sequence
<220> FEATURE:
<223> OTHER INFORMATION: Synthetic: mmu-miR-215

<400> SEQUENCE: 445
augaccuaug auuugacaga c                                       21

<210> SEQ ID NO 446
<211> LENGTH: 22
<212> TYPE: RNA
<213> ORGANISM: Artificial Sequence
<220> FEATURE:
<223> OTHER INFORMATION: Synthetic: mmu-miR-450b-5p

<400> SEQUENCE: 446
uuuugcagua uguuccugaa ua                                      22

<210> SEQ ID NO 447
<211> LENGTH: 22
<212> TYPE: RNA
<213> ORGANISM: Artificial Sequence
<220> FEATURE:
<223> OTHER INFORMATION: Synthetic: mmu-miR-676*

<400> SEQUENCE: 447
acucuacaac cuuaggacuu gc                                      22

<210> SEQ ID NO 448
<211> LENGTH: 21
<212> TYPE: RNA
<213> ORGANISM: Artificial Sequence
<220> FEATURE:
<223> OTHER INFORMATION: Synthetic: mmu-miR-875-3p

<400> SEQUENCE: 448
ccugaaaaua cugaggcuau g                                       21

<210> SEQ ID NO 449
<211> LENGTH: 21
<212> TYPE: RNA
<213> ORGANISM: Artificial Sequence
<220> FEATURE:
<223> OTHER INFORMATION: Synthetic: mmu-miR-455

<400> SEQUENCE: 449
gcaguccacg ggcauauaca c                                       21

-continued

```
<210> SEQ ID NO 450
<211> LENGTH: 22
<212> TYPE: RNA
<213> ORGANISM: Artificial Sequence
<220> FEATURE:
<223> OTHER INFORMATION: Synthetic: mmu-miR-210

<400> SEQUENCE: 450
cugugcgugu gacagcggcu ga                                          22

<210> SEQ ID NO 451
<211> LENGTH: 22
<212> TYPE: RNA
<213> ORGANISM: Artificial Sequence
<220> FEATURE:
<223> OTHER INFORMATION: Synthetic: mmu-miR-154*

<400> SEQUENCE: 451
aaucauacac gguugaccua uu                                          22

<210> SEQ ID NO 452
<211> LENGTH: 22
<212> TYPE: RNA
<213> ORGANISM: Artificial Sequence
<220> FEATURE:
<223> OTHER INFORMATION: Synthetic: mmu-miR-380-5p

<400> SEQUENCE: 452
augguugacc auagaacaug cg                                          22

<210> SEQ ID NO 453
<211> LENGTH: 22
<212> TYPE: RNA
<213> ORGANISM: Artificial Sequence
<220> FEATURE:
<223> OTHER INFORMATION: Synthetic: mmu-miR-669e

<400> SEQUENCE: 453
ugucuugugu gugcauguuc au                                          22

<210> SEQ ID NO 454
<211> LENGTH: 22
<212> TYPE: RNA
<213> ORGANISM: Artificial Sequence
<220> FEATURE:
<223> OTHER INFORMATION: Synthetic: mmu-miR-93*

<400> SEQUENCE: 454
acugcugagc uagcacuucc cg                                          22

<210> SEQ ID NO 455
<211> LENGTH: 21
<212> TYPE: RNA
<213> ORGANISM: Artificial Sequence
<220> FEATURE:
<223> OTHER INFORMATION: Synthetic: mmu-miR-547

<400> SEQUENCE: 455
cuugguacau cuuugaguga g                                           21

<210> SEQ ID NO 456
<211> LENGTH: 23
<212> TYPE: RNA
<213> ORGANISM: Artificial Sequence
<220> FEATURE:
<223> OTHER INFORMATION: Synthetic: mmu-miR-592
```

-continued

```
<400> SEQUENCE: 456
auugugucaa uaugcgauga ugu                                            23

<210> SEQ ID NO 457
<211> LENGTH: 21
<212> TYPE: RNA
<213> ORGANISM: Artificial Sequence
<220> FEATURE:
<223> OTHER INFORMATION: Synthetic: mmu-miR-721

<400> SEQUENCE: 457
cagugcaauu aaaagggga a                                               21

<210> SEQ ID NO 458
<211> LENGTH: 21
<212> TYPE: RNA
<213> ORGANISM: Artificial Sequence
<220> FEATURE:
<223> OTHER INFORMATION: Synthetic: mmu-miR-1983

<400> SEQUENCE: 458
cucaccugga gcauguuuuc u                                              21

<210> SEQ ID NO 459
<211> LENGTH: 21
<212> TYPE: RNA
<213> ORGANISM: Artificial Sequence
<220> FEATURE:
<223> OTHER INFORMATION: Synthetic: mmu-miR-466d-3p

<400> SEQUENCE: 459
uauacauaca cgcacacaua g                                              21

<210> SEQ ID NO 460
<211> LENGTH: 18
<212> TYPE: RNA
<213> ORGANISM: Artificial Sequence
<220> FEATURE:
<223> OTHER INFORMATION: Synthetic: mmu-miR-696

<400> SEQUENCE: 460
gcgugugcuu gcuguggg                                                  18

<210> SEQ ID NO 461
<211> LENGTH: 27
<212> TYPE: RNA
<213> ORGANISM: Artificial Sequence
<220> FEATURE:
<223> OTHER INFORMATION: Synthetic: mmu-miR-1946a

<400> SEQUENCE: 461
agccgggcag ugguggcaca cacuuuu                                        27

<210> SEQ ID NO 462
<211> LENGTH: 22
<212> TYPE: RNA
<213> ORGANISM: Artificial Sequence
<220> FEATURE:
<223> OTHER INFORMATION: Synthetic: mmu-miR-185

<400> SEQUENCE: 462
uggagagaaa ggcaguuccu ga                                             22

<210> SEQ ID NO 463
<211> LENGTH: 22
```

```
<212> TYPE: RNA
<213> ORGANISM: Artificial Sequence
<220> FEATURE:
<223> OTHER INFORMATION: Synthetic: mmu-miR-467b*

<400> SEQUENCE: 463
auauacauac acacaccaac ac                                              22

<210> SEQ ID NO 464
<211> LENGTH: 22
<212> TYPE: RNA
<213> ORGANISM: Artificial Sequence
<220> FEATURE:
<223> OTHER INFORMATION: Synthetic: mmu-miR-491

<400> SEQUENCE: 464 agugggaac ccuuccauga gg                                               22

<210> SEQ ID NO 465
<211> LENGTH: 22
<212> TYPE: RNA
<213> ORGANISM: Artificial Sequence
<220> FEATURE:
<223> OTHER INFORMATION: Synthetic: mmu-miR-1935

<400> SEQUENCE: 465
aggcagaggc uggcggaucu cu                                              22

<210> SEQ ID NO 466
<211> LENGTH: 22
<212> TYPE: RNA
<213> ORGANISM: Artificial Sequence
<220> FEATURE:
<223> OTHER INFORMATION: Synthetic: mmu-miR-27b*

<400> SEQUENCE: 466
agagcuuagc ugauugguga ac                                              22

<210> SEQ ID NO 467
<211> LENGTH: 26
<212> TYPE: RNA
<213> ORGANISM: Artificial Sequence
<220> FEATURE:
<223> OTHER INFORMATION: Synthetic: mmu-miR-1946b

<400> SEQUENCE: 467
gccgggcagu gguggcacau gcuuuu                                          26

<210> SEQ ID NO 468
<211> LENGTH: 22
<212> TYPE: RNA
<213> ORGANISM: Artificial Sequence
<220> FEATURE:
<223> OTHER INFORMATION: Synthetic: mmu-miR-450b-3p

<400> SEQUENCE: 468
auugggaaca uuuugcaugc au                                              22

<210> SEQ ID NO 469
<211> LENGTH: 22
<212> TYPE: RNA
<213> ORGANISM: Artificial Sequence
<220> FEATURE:
<223> OTHER INFORMATION: Synthetic: mmu-miR-293*

<400> SEQUENCE: 469
```

-continued acucaaacug ugugacauuu ug                                                22

<210> SEQ ID NO 470
<211> LENGTH: 22
<212> TYPE: RNA
<213> ORGANISM: Artificial Sequence
<220> FEATURE:
<223> OTHER INFORMATION: Synthetic: mmu-miR-27a*

<400> SEQUENCE: 470
agggcuuagc ugcuugugag ca                                                22

<210> SEQ ID NO 471
<211> LENGTH: 22
<212> TYPE: RNA
<213> ORGANISM: Artificial Sequence
<220> FEATURE:
<223> OTHER INFORMATION: Synthetic: mmu-miR-743b-3p

<400> SEQUENCE: 471
gaaagacauc augcugaaua ga                                                22

<210> SEQ ID NO 472
<211> LENGTH: 22
<212> TYPE: RNA
<213> ORGANISM: Artificial Sequence
<220> FEATURE:
<223> OTHER INFORMATION: Synthetic: mmu-miR-203*

<400> SEQUENCE: 472
agugguucuu gacaguucaa ca                                                22

<210> SEQ ID NO 473
<211> LENGTH: 22
<212> TYPE: RNA
<213> ORGANISM: Artificial Sequence
<220> FEATURE:
<223> OTHER INFORMATION: Synthetic: mmu-miR-148a*

<400> SEQUENCE: 473
aaaguucuga gacacuccga cu                                                22

<210> SEQ ID NO 474
<211> LENGTH: 21
<212> TYPE: RNA
<213> ORGANISM: Artificial Sequence
<220> FEATURE:
<223> OTHER INFORMATION: Synthetic: mmu-miR-488

<400> SEQUENCE: 474
uugaaaggcu guuucuuggu c                                                 21

<210> SEQ ID NO 475
<211> LENGTH: 22
<212> TYPE: RNA
<213> ORGANISM: Artificial Sequence
<220> FEATURE:
<223> OTHER INFORMATION: Synthetic: mmu-miR-669j

<400> SEQUENCE: 475
ugcauauacu cacaugcaaa ca                                                22

<210> SEQ ID NO 476
<211> LENGTH: 22
<212> TYPE: RNA
<213> ORGANISM: Artificial Sequence -continued

```
<220> FEATURE:
<223> OTHER INFORMATION: Synthetic: mmu-miR-382*

<400> SEQUENCE: 476
ucauucacgg acaacacuuu uu                                                     22

<210> SEQ ID NO 477
<211> LENGTH: 22
<212> TYPE: RNA
<213> ORGANISM: Artificial Sequence
<220> FEATURE:
<223> OTHER INFORMATION: Synthetic: mmu-miR-669d

<400> SEQUENCE: 477
acuugugugu gcauguauau gu                                                     22

<210> SEQ ID NO 478
<211> LENGTH: 22
<212> TYPE: RNA
<213> ORGANISM: Artificial Sequence
<220> FEATURE:
<223> OTHER INFORMATION: Synthetic: mmu-miR-1930

<400> SEQUENCE: 478
accuccauag uaccugcagc gu                                                     22

<210> SEQ ID NO 479
<211> LENGTH: 22
<212> TYPE: RNA
<213> ORGANISM: Artificial Sequence
<220> FEATURE:
<223> OTHER INFORMATION: Synthetic: mmu-miR-340-3p

<400> SEQUENCE: 479
uccgucucag uuacuuuaua gc                                                     22

<210> SEQ ID NO 480
<211> LENGTH: 21
<212> TYPE: RNA
<213> ORGANISM: Artificial Sequence
<220> FEATURE:
<223> OTHER INFORMATION: Synthetic: mmu-miR-701

<400> SEQUENCE: 480
uuagccgcug aaauagaugg a                                                      21

<210> SEQ ID NO 481
<211> LENGTH: 21
<212> TYPE: RNA
<213> ORGANISM: Artificial Sequence
<220> FEATURE:
<223> OTHER INFORMATION: Synthetic: mmu-miR-126-5p

<400> SEQUENCE: 481
cauuauuacu uuuggguacgc g                                                     21

<210> SEQ ID NO 482
<211> LENGTH: 22
<212> TYPE: RNA
<213> ORGANISM: Artificial Sequence
<220> FEATURE:
<223> OTHER INFORMATION: Synthetic: mmu-miR-31

<400> SEQUENCE: 482
aggcaagaug cuggcauagc ug                                                     22
```

-continued

<210> SEQ ID NO 483
<211> LENGTH: 21
<212> TYPE: RNA
<213> ORGANISM: Artificial Sequence
<220> FEATURE:
<223> OTHER INFORMATION: Synthetic: mmu-miR-143

<400> SEQUENCE: 483
ugagaugaag cacuguagcu c                                          21

<210> SEQ ID NO 484
<211> LENGTH: 22
<212> TYPE: RNA
<213> ORGANISM: Artificial Sequence
<220> FEATURE:
<223> OTHER INFORMATION: Synthetic: mmu-miR-196a

<400> SEQUENCE: 484
uagguaguuu cauguuguug gg                                         22

<210> SEQ ID NO 485
<211> LENGTH: 22
<212> TYPE: RNA
<213> ORGANISM: Artificial Sequence
<220> FEATURE:
<223> OTHER INFORMATION: Synthetic: mmu-miR-29b*

<400> SEQUENCE: 485
gcugguuuca uauggugguu ua                                         22

<210> SEQ ID NO 486
<211> LENGTH: 23
<212> TYPE: RNA
<213> ORGANISM: Artificial Sequence
<220> FEATURE:
<223> OTHER INFORMATION: Synthetic: mmu-miR-149

<400> SEQUENCE: 486
ucuggcuccg ugucuucacu ccc                                        23

<210> SEQ ID NO 487
<211> LENGTH: 21
<212> TYPE: RNA
<213> ORGANISM: Artificial Sequence
<220> FEATURE:
<223> OTHER INFORMATION: Synthetic: mmu-miR-128

<400> SEQUENCE: 487
ucacagugaa ccggucucuu u                                          21

<210> SEQ ID NO 488
<211> LENGTH: 22
<212> TYPE: RNA
<213> ORGANISM: Artificial Sequence
<220> FEATURE:
<223> OTHER INFORMATION: Synthetic: mmu-miR-706

<400> SEQUENCE: 488
agagaaaccc ugucucaaaa aa                                         22

<210> SEQ ID NO 489
<211> LENGTH: 22
<212> TYPE: RNA
<213> ORGANISM: Artificial Sequence
<220> FEATURE:
<223> OTHER INFORMATION: Synthetic: mmu-miR-153

-continued

```
<400> SEQUENCE: 489
uugcauaguc acaaaaguga uc                                                   22

<210> SEQ ID NO 490
<211> LENGTH: 22
<212> TYPE: RNA
<213> ORGANISM: Artificial Sequence
<220> FEATURE:
<223> OTHER INFORMATION: Synthetic: mmu-miR-193*

<400> SEQUENCE: 490
ugggucuuug cgggcaagau ga                                                   22

<210> SEQ ID NO 491
<211> LENGTH: 21
<212> TYPE: RNA
<213> ORGANISM: Artificial Sequence
<220> FEATURE:
<223> OTHER INFORMATION: Synthetic: mmu-miR-322*

<400> SEQUENCE: 491
aaacaugaag cgcugcaaca c                                                    21

<210> SEQ ID NO 492
<211> LENGTH: 23
<212> TYPE: RNA
<213> ORGANISM: Artificial Sequence
<220> FEATURE:
<223> OTHER INFORMATION: Synthetic: mmu-miR-9

<400> SEQUENCE: 492
ucuuugguua ucuagcugua uga                                                  23

<210> SEQ ID NO 493
<211> LENGTH: 21
<212> TYPE: RNA
<213> ORGANISM: Artificial Sequence
<220> FEATURE:
<223> OTHER INFORMATION: Synthetic: mmu-miR-190b

<400> SEQUENCE: 493
ugauauguuu gauauugggu u                                                    21

<210> SEQ ID NO 494
<211> LENGTH: 22
<212> TYPE: RNA
<213> ORGANISM: Artificial Sequence
<220> FEATURE:
<223> OTHER INFORMATION: Synthetic: mmu-miR-375

<400> SEQUENCE: 494
uuuguucguu cggcucgcgu ga                                                   22

<210> SEQ ID NO 495
<211> LENGTH: 22
<212> TYPE: RNA
<213> ORGANISM: Artificial Sequence
<220> FEATURE:
<223> OTHER INFORMATION: Synthetic: mmu-miR-92a*

<400> SEQUENCE: 495
agguggggau ugguggcauu ac                                                   22

<210> SEQ ID NO 496
```

-continued

<211> LENGTH: 22
<212> TYPE: RNA
<213> ORGANISM: Artificial Sequence
<220> FEATURE:
<223> OTHER INFORMATION: Synthetic: mmu-miR-20a*

<400> SEQUENCE: 496
acugcauuac gagcacuuaa ag                                                    22

<210> SEQ ID NO 497
<211> LENGTH: 21
<212> TYPE: RNA
<213> ORGANISM: Artificial Sequence
<220> FEATURE:
<223> OTHER INFORMATION: Synthetic: mmu-miR-133a*

<400> SEQUENCE: 497
gcugguaaaa uggaaccaaa u                                                     21

<210> SEQ ID NO 498
<211> LENGTH: 22
<212> TYPE: RNA
<213> ORGANISM: Artificial Sequence
<220> FEATURE:
<223> OTHER INFORMATION: Synthetic: mmu-miR-362-3p

<400> SEQUENCE: 498
aacacaccug uucaaggauu ca                                                    22

<210> SEQ ID NO 499
<211> LENGTH: 23
<212> TYPE: RNA
<213> ORGANISM: Artificial Sequence
<220> FEATURE:
<223> OTHER INFORMATION: Synthetic: mmu-miR-20a

<400> SEQUENCE: 499
uaaagugcuu auagugcagg uag                                                   23

<210> SEQ ID NO 500
<211> LENGTH: 23
<212> TYPE: RNA
<213> ORGANISM: Artificial Sequence
<220> FEATURE:
<223> OTHER INFORMATION: Synthetic: mmu-miR-106a

<400> SEQUENCE: 500
caaagugcua acagugcagg uag                                                   23

<210> SEQ ID NO 501
<211> LENGTH: 22
<212> TYPE: RNA
<213> ORGANISM: Artificial Sequence
<220> FEATURE:
<223> OTHER INFORMATION: Synthetic: mmu-miR-532-5p

<400> SEQUENCE: 501
caugccuuga guguaggacc gu                                                    22

<210> SEQ ID NO 502
<211> LENGTH: 22
<212> TYPE: RNA
<213> ORGANISM: Artificial Sequence
<220> FEATURE:
<223> OTHER INFORMATION: Synthetic: mmu-miR-15b*

<400> SEQUENCE: 502

-continued cgaaucauua uuugcugcuc ua                                                  22

<210> SEQ ID NO 503
<211> LENGTH: 23
<212> TYPE: RNA
<213> ORGANISM: Artificial Sequence
<220> FEATURE:
<223> OTHER INFORMATION: Synthetic: mmu-miR-191

<400> SEQUENCE: 503
caacggaauc ccaaaagcag cug                                                 23

<210> SEQ ID NO 504
<211> LENGTH: 23
<212> TYPE: RNA
<213> ORGANISM: Artificial Sequence
<220> FEATURE:
<223> OTHER INFORMATION: Synthetic: mmu-miR-181b

<400> SEQUENCE: 504
aacauucauu gcugucggug ggu                                                 23

<210> SEQ ID NO 505
<211> LENGTH: 22
<212> TYPE: RNA
<213> ORGANISM: Artificial Sequence
<220> FEATURE:
<223> OTHER INFORMATION: Synthetic: mmu-miR-126-3p

<400> SEQUENCE: 505
ucguaccgug aguaauaaug cg                                                  22

<210> SEQ ID NO 506
<211> LENGTH: 23
<212> TYPE: RNA
<213> ORGANISM: Artificial Sequence
<220> FEATURE:
<223> OTHER INFORMATION: Synthetic: mmu-miR-18a

<400> SEQUENCE: 506
uaaggugcau cuagugcaga uag                                                 23

<210> SEQ ID NO 507
<211> LENGTH: 22
<212> TYPE: RNA
<213> ORGANISM: Artificial Sequence
<220> FEATURE:
<223> OTHER INFORMATION: Synthetic: mmu-miR-22*

<400> SEQUENCE: 507
aguucuucag uggcaagcuu ua                                                  22

<210> SEQ ID NO 508
<211> LENGTH: 23
<212> TYPE: RNA
<213> ORGANISM: Artificial Sequence
<220> FEATURE:
<223> OTHER INFORMATION: Synthetic: mmu-miR-301a

<400> SEQUENCE: 508
cagugcaaua guauugucaa agc                                                 23

<210> SEQ ID NO 509
<211> LENGTH: 23
<212> TYPE: RNA

-continued

<213> ORGANISM: Artificial Sequence
<220> FEATURE:
<223> OTHER INFORMATION: Synthetic: mmu-miR-301b

<400> SEQUENCE: 509
cagugcaaug guauugucaa agc                                              23

<210> SEQ ID NO 510
<211> LENGTH: 23
<212> TYPE: RNA
<213> ORGANISM: Artificial Sequence
<220> FEATURE:
<223> OTHER INFORMATION: Synthetic: mmu-miR-17

<400> SEQUENCE: 510
caaagugcuu acagugcagg uag                                              23

<210> SEQ ID NO 511
<211> LENGTH: 22
<212> TYPE: RNA
<213> ORGANISM: Artificial Sequence
<220> FEATURE:
<223> OTHER INFORMATION: Synthetic: mmu-miR-181a-1*

<400> SEQUENCE: 511
accaucgacc guugauugua cc                                               22

<210> SEQ ID NO 512
<211> LENGTH: 24
<212> TYPE: RNA
<213> ORGANISM: Artificial Sequence
<220> FEATURE:
<223> OTHER INFORMATION: Synthetic: mmu-miR-362-5p

<400> SEQUENCE: 512
aauccuugga accuaggugu gaau                                             24

<210> SEQ ID NO 513
<211> LENGTH: 21
<212> TYPE: RNA
<213> ORGANISM: Artificial Sequence
<220> FEATURE:
<223> OTHER INFORMATION: Synthetic: mmu-miR-499

<400> SEQUENCE: 513
uuaagacuug cagugauguu u                                                21

<210> SEQ ID NO 514
<211> LENGTH: 22
<212> TYPE: RNA
<213> ORGANISM: Artificial Sequence
<220> FEATURE:
<223> OTHER INFORMATION: Synthetic: mmu-miR-29a*

<400> SEQUENCE: 514
acugauuucu uuggguguuc ag                                               22

<210> SEQ ID NO 515
<211> LENGTH: 22
<212> TYPE: RNA
<213> ORGANISM: Artificial Sequence
<220> FEATURE:
<223> OTHER INFORMATION: Synthetic: mmu-miR-193b

<400> SEQUENCE: 515
aacuggccca caaagucccg cu                                               22

```
<210> SEQ ID NO 516
<211> LENGTH: 19
<212> TYPE: RNA
<213> ORGANISM: Artificial Sequence
<220> FEATURE:
<223> OTHER INFORMATION: Synthetic: mmu-miR-2142

<400> SEQUENCE: 516
accgggugcu guaggcuuu                                                     19

<210> SEQ ID NO 517
<211> LENGTH: 20
<212> TYPE: RNA
<213> ORGANISM: Artificial Sequence
<220> FEATURE:
<223> OTHER INFORMATION: Synthetic: mmu-miR-877

<400> SEQUENCE: 517
guagaggaga uggcgcaggg                                                    20

<210> SEQ ID NO 518
<211> LENGTH: 23
<212> TYPE: RNA
<213> ORGANISM: Artificial Sequence
<220> FEATURE:
<223> OTHER INFORMATION: Synthetic: mmu-miR-324-5p

<400> SEQUENCE: 518
cgcauccccu agggcauugg ugu                                                23

<210> SEQ ID NO 519
<211> LENGTH: 21
<212> TYPE: RNA
<213> ORGANISM: Artificial Sequence
<220> FEATURE:
<223> OTHER INFORMATION: Synthetic: mmu-miR-692

<400> SEQUENCE: 519
aucucuuuga gcgccucacu c                                                  21

<210> SEQ ID NO 520
<211> LENGTH: 22
<212> TYPE: RNA
<213> ORGANISM: Artificial Sequence
<220> FEATURE:
<223> OTHER INFORMATION: Synthetic: mmu-miR-214

<400> SEQUENCE: 520
acagcaggca cagacaggca gu                                                 22

<210> SEQ ID NO 521
<211> LENGTH: 22
<212> TYPE: RNA
<213> ORGANISM: Artificial Sequence
<220> FEATURE:
<223> OTHER INFORMATION: Synthetic: mmu-miR-193

<400> SEQUENCE: 521
aacuggccua caaagucccu gu                                                 22

<210> SEQ ID NO 522
<211> LENGTH: 22
<212> TYPE: RNA
<213> ORGANISM: Artificial Sequence
<220> FEATURE:
```

-continued

<223> OTHER INFORMATION: Synthetic: mmu-miR-291a-5p

<400> SEQUENCE: 522
caucaaagug gaggcccucu cu                                          22

<210> SEQ ID NO 523
<211> LENGTH: 19
<212> TYPE: RNA
<213> ORGANISM: Artificial Sequence
<220> FEATURE:
<223> OTHER INFORMATION: Synthetic: mmu-miR-2145

<400> SEQUENCE: 523
agcagggucg ggccugguu                                             19

<210> SEQ ID NO 524
<211> LENGTH: 22
<212> TYPE: RNA
<213> ORGANISM: Artificial Sequence
<220> FEATURE:
<223> OTHER INFORMATION: Synthetic: mmu-miR-770-5p

<400> SEQUENCE: 524
agcaccacgu gucugggcca cg                                          22

<210> SEQ ID NO 525
<211> LENGTH: 23
<212> TYPE: RNA
<213> ORGANISM: Artificial Sequence
<220> FEATURE:
<223> OTHER INFORMATION: Synthetic: mmu-miR-669f

<400> SEQUENCE: 525
cauauacaua cacacacacg uau                                         23

<210> SEQ ID NO 526
<211> LENGTH: 21
<212> TYPE: RNA
<213> ORGANISM: Artificial Sequence
<220> FEATURE:
<223> OTHER INFORMATION: Synthetic: mmu-miR-1224

<400> SEQUENCE: 526
gugaggacug gggaggugga g                                           21

<210> SEQ ID NO 527
<211> LENGTH: 22
<212> TYPE: RNA
<213> ORGANISM: Artificial Sequence
<220> FEATURE:
<223> OTHER INFORMATION: Synthetic: mmu-miR-1892

<400> SEQUENCE: 527 auuugggggac gggagggagg au                                         22

<210> SEQ ID NO 528
<211> LENGTH: 21
<212> TYPE: RNA
<213> ORGANISM: Artificial Sequence
<220> FEATURE:
<223> OTHER INFORMATION: Synthetic: mmu-miR-1965

<400> SEQUENCE: 528
aagccgggcc guaguggcgc a                                           21

-continued

```
<210> SEQ ID NO 529
<211> LENGTH: 19
<212> TYPE: RNA
<213> ORGANISM: Artificial Sequence
<220> FEATURE:
<223> OTHER INFORMATION: Synthetic: mmu-miR-2132

<400> SEQUENCE: 529
ggcgggcguu gacgcgaug                                              19

<210> SEQ ID NO 530
<211> LENGTH: 23
<212> TYPE: RNA
<213> ORGANISM: Artificial Sequence
<220> FEATURE:
<223> OTHER INFORMATION: Synthetic: mmu-miR-708

<400> SEQUENCE: 530
aaggagcuua caaucuagcu ggg                                         23

<210> SEQ ID NO 531
<211> LENGTH: 22
<212> TYPE: RNA
<213> ORGANISM: Artificial Sequence
<220> FEATURE:
<223> OTHER INFORMATION: Synthetic: mmu-miR-130b

<400> SEQUENCE: 531
cagugcaaug augaaagggc au                                          22

<210> SEQ ID NO 532
<211> LENGTH: 21
<212> TYPE: RNA
<213> ORGANISM: Artificial Sequence
<220> FEATURE:
<223> OTHER INFORMATION: Synthetic: mmu-miR-411

<400> SEQUENCE: 532
uaguagaccg uauagcguac g                                           21

<210> SEQ ID NO 533
<211> LENGTH: 19
<212> TYPE: RNA
<213> ORGANISM: Artificial Sequence
<220> FEATURE:
<223> OTHER INFORMATION: Synthetic: mmu-miR-2141

<400> SEQUENCE: 533 aggaggguguc agaaaaguu                                             19

<210> SEQ ID NO 534
<211> LENGTH: 21
<212> TYPE: RNA
<213> ORGANISM: Artificial Sequence
<220> FEATURE:
<223> OTHER INFORMATION: Synthetic: mmu-miR-718

<400> SEQUENCE: 534
cuuccgcccg gccggguguc g                                           21

<210> SEQ ID NO 535
<211> LENGTH: 22
<212> TYPE: RNA
<213> ORGANISM: Artificial Sequence
<220> FEATURE:
<223> OTHER INFORMATION: Synthetic: mmu-miR-328
```

-continued

```
<400> SEQUENCE: 535
cuggcccucu cugcccuucc gu                                          22

<210> SEQ ID NO 536
<211> LENGTH: 22
<212> TYPE: RNA
<213> ORGANISM: Artificial Sequence
<220> FEATURE:
<223> OTHER INFORMATION: Synthetic: mmu-miR-804

<400> SEQUENCE: 536
ugugaguugu uccucaccug ga                                         22

<210> SEQ ID NO 537
<211> LENGTH: 19
<212> TYPE: RNA
<213> ORGANISM: Artificial Sequence
<220> FEATURE:
<223> OTHER INFORMATION: Synthetic: mmu-miR-709

<400> SEQUENCE: 537
ggaggcagag gcaggagga                                             19

<210> SEQ ID NO 538
<211> LENGTH: 22
<212> TYPE: RNA
<213> ORGANISM: Artificial Sequence
<220> FEATURE:
<223> OTHER INFORMATION: Synthetic: mmu-miR-1931

<400> SEQUENCE: 538
augcaagggc uggugcgaug gc                                         22

<210> SEQ ID NO 539
<211> LENGTH: 24
<212> TYPE: RNA
<213> ORGANISM: Artificial Sequence
<220> FEATURE:
<223> OTHER INFORMATION: Synthetic: mmu-miR-1981

<400> SEQUENCE: 539
guaaaggcug ggcuuagacg uggc                                       24

<210> SEQ ID NO 540
<211> LENGTH: 25
<212> TYPE: RNA
<213> ORGANISM: Artificial Sequence
<220> FEATURE:
<223> OTHER INFORMATION: Synthetic: mmu-miR-2144

<400> SEQUENCE: 540
gagugccuag ugggccacuu uuggu                                      25

<210> SEQ ID NO 541
<211> LENGTH: 22
<212> TYPE: RNA
<213> ORGANISM: Artificial Sequence
<220> FEATURE:
<223> OTHER INFORMATION: Synthetic: mmu-miR-135a*

<400> SEQUENCE: 541
uauagggauu ggagccgugg cg                                         22

<210> SEQ ID NO 542
<211> LENGTH: 23
```

-continued

```
<212> TYPE: RNA
<213> ORGANISM: Artificial Sequence
<220> FEATURE:
<223> OTHER INFORMATION: Synthetic: mmu-miR-466b-3p

<400> SEQUENCE: 542
uauacauaca cgcacacaua aga                                            23

<210> SEQ ID NO 543
<211> LENGTH: 22
<212> TYPE: RNA
<213> ORGANISM: Artificial Sequence
<220> FEATURE:
<223> OTHER INFORMATION: Synthetic: mmu-miR-323-5p

<400> SEQUENCE: 543
aggugguccg uggcgcguuc gc                                             22

<210> SEQ ID NO 544
<211> LENGTH: 22
<212> TYPE: RNA
<213> ORGANISM: Artificial Sequence
<220> FEATURE:
<223> OTHER INFORMATION: Synthetic: mmu-let-7c

<400> SEQUENCE: 544
ugagguagua gguuguaugg uu                                             22

<210> SEQ ID NO 545
<211> LENGTH: 22
<212> TYPE: RNA
<213> ORGANISM: Artificial Sequence
<220> FEATURE:
<223> OTHER INFORMATION: Synthetic: mmu-let-7b

<400> SEQUENCE: 545
ugagguagua gguugugugg uu                                             22

<210> SEQ ID NO 546
<211> LENGTH: 21
<212> TYPE: RNA
<213> ORGANISM: Artificial Sequence
<220> FEATURE:
<223> OTHER INFORMATION: Synthetic: mmu-miR-378

<400> SEQUENCE: 546
acuggacuug gagucagaag g                                              21

<210> SEQ ID NO 547
<211> LENGTH: 19
<212> TYPE: RNA
<213> ORGANISM: Artificial Sequence
<220> FEATURE:
<223> OTHER INFORMATION: Synthetic: mmu-miR-2140

<400> SEQUENCE: 547
aggugcagau cuugguggu                                                 19

<210> SEQ ID NO 548
<211> LENGTH: 20
<212> TYPE: RNA
<213> ORGANISM: Artificial Sequence
<220> FEATURE:
<223> OTHER INFORMATION: Synthetic: mmu-miR-2146

<400> SEQUENCE: 548
```

-continued guggagaagg guuccaugug                                                    20

<210> SEQ ID NO 549
<211> LENGTH: 22
<212> TYPE: RNA
<213> ORGANISM: Artificial Sequence
<220> FEATURE:
<223> OTHER INFORMATION: Synthetic: mmu-miR-139-5p

<400> SEQUENCE: 549
ucuacagugc acgugucucc ag                                                 22

<210> SEQ ID NO 550
<211> LENGTH: 22
<212> TYPE: RNA
<213> ORGANISM: Artificial Sequence
<220> FEATURE:
<223> OTHER INFORMATION: Synthetic: mmu-miR-183

<400> SEQUENCE: 550
uauggcacug guagaauuca cu                                                 22

<210> SEQ ID NO 551
<211> LENGTH: 22
<212> TYPE: RNA
<213> ORGANISM: Artificial Sequence
<220> FEATURE:
<223> OTHER INFORMATION: Synthetic: mmu-let-7c-2*

<400> SEQUENCE: 551
cuauacaauc uacugucuuu cc                                                 22

<210> SEQ ID NO 552
<211> LENGTH: 22
<212> TYPE: RNA
<213> ORGANISM: Artificial Sequence
<220> FEATURE:
<223> OTHER INFORMATION: Synthetic: mmu-miR-494

<400> SEQUENCE: 552
ugaaacauac acgggaaacc uc                                                 22

<210> SEQ ID NO 553
<211> LENGTH: 22
<212> TYPE: RNA
<213> ORGANISM: Artificial Sequence
<220> FEATURE:
<223> OTHER INFORMATION: Synthetic: mmu-miR-365

<400> SEQUENCE: 553
uaaugccccu aaaaauccuu au                                                 22

<210> SEQ ID NO 554
<211> LENGTH: 22
<212> TYPE: RNA
<213> ORGANISM: Artificial Sequence
<220> FEATURE:
<223> OTHER INFORMATION: Synthetic: mmu-miR-465c-5p

<400> SEQUENCE: 554
uauuuagaau ggcgcugauc ug                                                 22

<210> SEQ ID NO 555
<211> LENGTH: 21
<212> TYPE: RNA
<213> ORGANISM: Artificial Sequence -continued

```
<220> FEATURE:
<223> OTHER INFORMATION: Synthetic: mmu-miR-467b

<400> SEQUENCE: 555
guaagugccu gcauguauau g                                              21

<210> SEQ ID NO 556
<211> LENGTH: 22
<212> TYPE: RNA
<213> ORGANISM: Artificial Sequence
<220> FEATURE:
<223> OTHER INFORMATION: Synthetic: mmu-miR-673-5p

<400> SEQUENCE: 556
cucacagcuc ugguccuugg ag                                             22

<210> SEQ ID NO 557
<211> LENGTH: 22
<212> TYPE: RNA
<213> ORGANISM: Artificial Sequence
<220> FEATURE:
<223> OTHER INFORMATION: Synthetic: mmu-miR-539

<400> SEQUENCE: 557
ggagaaauua uccuuggugu gu                                             22

<210> SEQ ID NO 558
<211> LENGTH: 21
<212> TYPE: RNA
<213> ORGANISM: Artificial Sequence
<220> FEATURE:
<223> OTHER INFORMATION: Synthetic: mmu-miR-92a

<400> SEQUENCE: 558
uauugcacuu gucccggccu g                                              21

<210> SEQ ID NO 559
<211> LENGTH: 21
<212> TYPE: RNA
<213> ORGANISM: Artificial Sequence
<220> FEATURE:
<223> OTHER INFORMATION: Synthetic: mmu-miR-151-3p

<400> SEQUENCE: 559
cuagacugag gcuccuugag g                                              21

<210> SEQ ID NO 560
<211> LENGTH: 24
<212> TYPE: RNA
<213> ORGANISM: Artificial Sequence
<220> FEATURE:
<223> OTHER INFORMATION: Synthetic: mmu-miR-668

<400> SEQUENCE: 560
ugucacucgg cucggcccac uacc                                           24

<210> SEQ ID NO 561
<211> LENGTH: 22
<212> TYPE: RNA
<213> ORGANISM: Artificial Sequence
<220> FEATURE:
<223> OTHER INFORMATION: Synthetic: mmu-miR-134

<400> SEQUENCE: 561
ugugacuggu ugaccagagg gg                                             22
```

<210> SEQ ID NO 562
<211> LENGTH: 22
<212> TYPE: RNA
<213> ORGANISM: Artificial Sequence
<220> FEATURE:
<223> OTHER INFORMATION: Synthetic: mmu-miR-92b

<400> SEQUENCE: 562
uauugcacuc gucccggccu cc                                                                              22

<210> SEQ ID NO 563
<211> LENGTH: 22
<212> TYPE: RNA
<213> ORGANISM: Artificial Sequence
<220> FEATURE:
<223> OTHER INFORMATION: Synthetic: mmu-miR-34c*

<400> SEQUENCE: 563
aaucacuaac cacacagcca gg                                                                              22

<210> SEQ ID NO 564
<211> LENGTH: 23
<212> TYPE: RNA
<213> ORGANISM: Artificial Sequence
<220> FEATURE:
<223> OTHER INFORMATION: Synthetic: mmu-miR-871

<400> SEQUENCE: 564
uauucagauu agugccaguc aug                                                                             23

<210> SEQ ID NO 565
<211> LENGTH: 22
<212> TYPE: RNA
<213> ORGANISM: Artificial Sequence
<220> FEATURE:
<223> OTHER INFORMATION: Synthetic: mmu-miR-2133

<400> SEQUENCE: 565
gucccgcggg gcccgaagcg uu                                                                              22

<210> SEQ ID NO 566
<211> LENGTH: 21
<212> TYPE: RNA
<213> ORGANISM: Artificial Sequence
<220> FEATURE:
<223> OTHER INFORMATION: Synthetic: mmu-miR-767

<400> SEQUENCE: 566
ugcaccaugg uugucugagc a                                                                               21

<210> SEQ ID NO 567
<211> LENGTH: 22
<212> TYPE: RNA
<213> ORGANISM: Artificial Sequence
<220> FEATURE:
<223> OTHER INFORMATION: Synthetic: mmu-miR-9*

<400> SEQUENCE: 567
auaaagcuag auaaccgaaa gu                                                                              22

<210> SEQ ID NO 568
<211> LENGTH: 23
<212> TYPE: RNA
<213> ORGANISM: Artificial Sequence
<220> FEATURE:
<223> OTHER INFORMATION: Synthetic: mmu-miR-741

<400> SEQUENCE: 568
ugagagaugc cauucuaugu aga                                    23

<210> SEQ ID NO 569
<211> LENGTH: 23
<212> TYPE: RNA
<213> ORGANISM: Artificial Sequence
<220> FEATURE:
<223> OTHER INFORMATION: Synthetic: mmu-miR-1929

<400> SEQUENCE: 569
uucuaggacu uuauagagca gag                                    23

<210> SEQ ID NO 570
<211> LENGTH: 20
<212> TYPE: RNA
<213> ORGANISM: Artificial Sequence
<220> FEATURE:
<223> OTHER INFORMATION: Synthetic: mmu-miR-1939

<400> SEQUENCE: 570
ucgauucccu gccaaugcac                                        20

<210> SEQ ID NO 571
<211> LENGTH: 21
<212> TYPE: RNA
<213> ORGANISM: Artificial Sequence
<220> FEATURE:
<223> OTHER INFORMATION: Synthetic: mmu-miR-331-3p

<400> SEQUENCE: 571
gccccugggc cuauccuaga a                                      21

<210> SEQ ID NO 572
<211> LENGTH: 21
<212> TYPE: RNA
<213> ORGANISM: Artificial Sequence
<220> FEATURE:
<223> OTHER INFORMATION: Synthetic: mmu-miR-192

<400> SEQUENCE: 572
cugaccuaug aauugacagc c                                      21

<210> SEQ ID NO 573
<211> LENGTH: 23
<212> TYPE: RNA
<213> ORGANISM: Artificial Sequence
<220> FEATURE:
<223> OTHER INFORMATION: Synthetic: mmu-miR-425

<400> SEQUENCE: 573
aaugacacga ucacucccgu uga                                    23

<210> SEQ ID NO 574
<211> LENGTH: 22
<212> TYPE: RNA
<213> ORGANISM: Artificial Sequence
<220> FEATURE:
<223> OTHER INFORMATION: Synthetic: mmu-miR-467a

<400> SEQUENCE: 574
uaagugccug cauguauaug cg                                     22

<210> SEQ ID NO 575

-continued

```
<211> LENGTH: 22
<212> TYPE: RNA
<213> ORGANISM: Artificial Sequence
<220> FEATURE:
<223> OTHER INFORMATION: Synthetic: mmu-miR-1962

<400> SEQUENCE: 575
agaggcuggc acugggacac au                                               22

<210> SEQ ID NO 576
<211> LENGTH: 22
<212> TYPE: RNA
<213> ORGANISM: Artificial Sequence
<220> FEATURE:
<223> OTHER INFORMATION: Synthetic: mmu-let-7d*

<400> SEQUENCE: 576
cuauacgacc ugcugccuuu cu                                               22

<210> SEQ ID NO 577
<211> LENGTH: 23
<212> TYPE: RNA
<213> ORGANISM: Artificial Sequence
<220> FEATURE:
<223> OTHER INFORMATION: Synthetic: mmu-miR-330*

<400> SEQUENCE: 577
gcaaagcaca gggccugcag aga                                              23

<210> SEQ ID NO 578
<211> LENGTH: 22
<212> TYPE: RNA
<213> ORGANISM: Artificial Sequence
<220> FEATURE:
<223> OTHER INFORMATION: Synthetic: mmu-miR-361

<400> SEQUENCE: 578
uuaucagaau cuccaggggu ac                                               22

<210> SEQ ID NO 579
<211> LENGTH: 22
<212> TYPE: RNA
<213> ORGANISM: Artificial Sequence
<220> FEATURE:
<223> OTHER INFORMATION: Synthetic: mmu-miR-378*

<400> SEQUENCE: 579
cuccugacuc cagguccugu gu                                               22

<210> SEQ ID NO 580
<211> LENGTH: 22
<212> TYPE: RNA
<213> ORGANISM: Artificial Sequence
<220> FEATURE:
<223> OTHER INFORMATION: Synthetic: mmu-miR-292-5p

<400> SEQUENCE: 580
acucaaacug ggggcucuuu ug                                               22

<210> SEQ ID NO 581
<211> LENGTH: 22
<212> TYPE: RNA
<213> ORGANISM: Artificial Sequence
<220> FEATURE:
<223> OTHER INFORMATION: Synthetic: mmu-miR-1933-3p

<400> SEQUENCE: 581
```

-continued

--- ccaggaccau cagugugacu au                                          22

<210> SEQ ID NO 582
<211> LENGTH: 22
<212> TYPE: RNA
<213> ORGANISM: Artificial Sequence
<220> FEATURE:
<223> OTHER INFORMATION: Synthetic: mmu-miR-1897-5p

<400> SEQUENCE: 582
cuuuggaugg agaaagaggg gg                                          22

<210> SEQ ID NO 583
<211> LENGTH: 23
<212> TYPE: RNA
<213> ORGANISM: Artificial Sequence
<220> FEATURE:
<223> OTHER INFORMATION: Synthetic: mmu-miR-669g

<400> SEQUENCE: 583
ugcauuguau guguugacau gau                                         23

<210> SEQ ID NO 584
<211> LENGTH: 25
<212> TYPE: RNA
<213> ORGANISM: Artificial Sequence
<220> FEATURE:
<223> OTHER INFORMATION: Synthetic: mmu-miR-182

<400> SEQUENCE: 584
uuuggcaaug guagaacuca caccg                                       25

<210> SEQ ID NO 585
<211> LENGTH: 22
<212> TYPE: RNA
<213> ORGANISM: Artificial Sequence
<220> FEATURE:
<223> OTHER INFORMATION: Synthetic: mmu-miR-30c-2*

<400> SEQUENCE: 585
cugggagaag gcuguuuacu cu                                          22

<210> SEQ ID NO 586
<211> LENGTH: 18
<212> TYPE: RNA
<213> ORGANISM: Artificial Sequence
<220> FEATURE:
<223> OTHER INFORMATION: Synthetic: mmu-miR-720

<400> SEQUENCE: 586
aucucgcugg ggccucca                                               18

<210> SEQ ID NO 587
<211> LENGTH: 22
<212> TYPE: RNA
<213> ORGANISM: Artificial Sequence
<220> FEATURE:
<223> OTHER INFORMATION: Synthetic: mmu-miR-106b*

<400> SEQUENCE: 587
ccgcacugug gguacuugcu gc                                          22

<210> SEQ ID NO 588
<211> LENGTH: 22
<212> TYPE: RNA

-continued

```
<213> ORGANISM: Artificial Sequence
<220> FEATURE:
<223> OTHER INFORMATION: Synthetic: mmu-miR-1900

<400> SEQUENCE: 588
ggccgccctc ucgguccuu ca                                               22

<210> SEQ ID NO 589
<211> LENGTH: 22
<212> TYPE: RNA
<213> ORGANISM: Artificial Sequence
<220> FEATURE:
<223> OTHER INFORMATION: Synthetic: mmu-miR-497

<400> SEQUENCE: 589
cagcagcaca cuggguuug ua                                               22

<210> SEQ ID NO 590
<211> LENGTH: 23
<212> TYPE: RNA
<213> ORGANISM: Artificial Sequence
<220> FEATURE:
<223> OTHER INFORMATION: Synthetic: mmu-miR-339-5p

<400> SEQUENCE: 590
ucccuguccu ccaggagcuc acg                                             23

<210> SEQ ID NO 591
<211> LENGTH: 22
<212> TYPE: RNA
<213> ORGANISM: Artificial Sequence
<220> FEATURE:
<223> OTHER INFORMATION: Synthetic: mmu-miR-1901

<400> SEQUENCE: 591
ccgcucguac ucccgggggu cc                                              22

<210> SEQ ID NO 592
<211> LENGTH: 23
<212> TYPE: RNA
<213> ORGANISM: Artificial Sequence
<220> FEATURE:
<223> OTHER INFORMATION: Synthetic: mmu-miR-145

<400> SEQUENCE: 592
guccaguuuu cccaggaauc ccu                                             23

<210> SEQ ID NO 593
<211> LENGTH: 22
<212> TYPE: RNA
<213> ORGANISM: Artificial Sequence
<220> FEATURE:
<223> OTHER INFORMATION: Synthetic: mmu-miR-690

<400> SEQUENCE: 593
aaaggcuagg cucacaacca aa                                              22

<210> SEQ ID NO 594
<211> LENGTH: 22
<212> TYPE: RNA
<213> ORGANISM: Artificial Sequence
<220> FEATURE:
<223> OTHER INFORMATION: Synthetic: mmu-miR-183*

<400> SEQUENCE: 594
gugaauuacc gaagggccau aa                                              22
```

<210> SEQ ID NO 595
<211> LENGTH: 22
<212> TYPE: RNA
<213> ORGANISM: Artificial Sequence
<220> FEATURE:
<223> OTHER INFORMATION: Synthetic: mmu-miR-881

<400> SEQUENCE: 595
aacugugucu uuucugaaua ga                                                      22

<210> SEQ ID NO 596
<211> LENGTH: 22
<212> TYPE: RNA
<213> ORGANISM: Artificial Sequence
<220> FEATURE:
<223> OTHER INFORMATION: Synthetic: mmu-let-7d

<400> SEQUENCE: 596
agagguagua gguugcauag uu                                                      22

<210> SEQ ID NO 597
<211> LENGTH: 22
<212> TYPE: RNA
<213> ORGANISM: Artificial Sequence
<220> FEATURE:
<223> OTHER INFORMATION: Synthetic: mmu-let-7a

<400> SEQUENCE: 597
ugagguagua gguuguauag uu                                                      22

<210> SEQ ID NO 598
<211> LENGTH: 22
<212> TYPE: RNA
<213> ORGANISM: Artificial Sequence
<220> FEATURE:
<223> OTHER INFORMATION: Synthetic: mmu-miR-1932

<400> SEQUENCE: 598
guugcggaca gcgcuagguc gg                                                      22

<210> SEQ ID NO 599
<211> LENGTH: 23
<212> TYPE: RNA
<213> ORGANISM: Artificial Sequence
<220> FEATURE:
<223> OTHER INFORMATION: Synthetic: mmu-miR-199b*

<400> SEQUENCE: 599
cccaguguuu agacuaccug uuc                                                     23

<210> SEQ ID NO 600
<211> LENGTH: 21
<212> TYPE: RNA
<213> ORGANISM: Artificial Sequence
<220> FEATURE:
<223> OTHER INFORMATION: Synthetic: mmu-miR-26b

<400> SEQUENCE: 600
uucaaguaau ucaggauagg u                                                       21

<210> SEQ ID NO 601
<211> LENGTH: 23
<212> TYPE: RNA
<213> ORGANISM: Artificial Sequence
<220> FEATURE:

<223> OTHER INFORMATION: Synthetic: mmu-miR-421

<400> SEQUENCE: 601
aucaacagac auuaauuggg cgc                                                                                                  23

<210> SEQ ID NO 602
<211> LENGTH: 21
<212> TYPE: RNA
<213> ORGANISM: Artificial Sequence
<220> FEATURE:
<223> OTHER INFORMATION: Synthetic: mmu-miR-151-5p

<400> SEQUENCE: 602
ucgaggagcu cacagucuag u                                                                                                     21

<210> SEQ ID NO 603
<211> LENGTH: 22
<212> TYPE: RNA
<213> ORGANISM: Artificial Sequence
<220> FEATURE:
<223> OTHER INFORMATION: Synthetic: mmu-miR-15b

<400> SEQUENCE: 603
uagcagcaca ucaugguuua ca                                                                                                    22

<210> SEQ ID NO 604
<211> LENGTH: 21
<212> TYPE: RNA
<213> ORGANISM: Artificial Sequence
<220> FEATURE:
<223> OTHER INFORMATION: Synthetic: mmu-miR-218

<400> SEQUENCE: 604
uugugcuuga ucuaaccaug u                                                                                                     21

<210> SEQ ID NO 605
<211> LENGTH: 23
<212> TYPE: RNA
<213> ORGANISM: Artificial Sequence
<220> FEATURE:
<223> OTHER INFORMATION: Synthetic: mmu-miR-24-1*

<400> SEQUENCE: 605
gugccuacug agcugauauc agu                                                                                                   23

<210> SEQ ID NO 606
<211> LENGTH: 22
<212> TYPE: RNA
<213> ORGANISM: Artificial Sequence
<220> FEATURE:
<223> OTHER INFORMATION: Synthetic: mmu-miR-674*

<400> SEQUENCE: 606
cacagcuccc aucucagaac aa                                                                                                    22

<210> SEQ ID NO 607
<211> LENGTH: 22
<212> TYPE: RNA
<213> ORGANISM: Artificial Sequence
<220> FEATURE:
<223> OTHER INFORMATION: Synthetic: mmu-miR-664

<400> SEQUENCE: 607
uauucauuua cuccccagcc ua                                                                                                    22

```
<210> SEQ ID NO 608
<211> LENGTH: 22
<212> TYPE: RNA
<213> ORGANISM: Artificial Sequence
<220> FEATURE:
<223> OTHER INFORMATION: Synthetic: mmu-let-7f

<400> SEQUENCE: 608
ugagguagua gauuguauag uu                                                      22

<210> SEQ ID NO 609
<211> LENGTH: 22
<212> TYPE: RNA
<213> ORGANISM: Artificial Sequence
<220> FEATURE:
<223> OTHER INFORMATION: Synthetic: mmu-miR-98

<400> SEQUENCE: 609
ugagguagua aguuguauug uu                                                      22

<210> SEQ ID NO 610
<211> LENGTH: 22
<212> TYPE: RNA
<213> ORGANISM: Artificial Sequence
<220> FEATURE:
<223> OTHER INFORMATION: Synthetic: mmu-miR-99a

<400> SEQUENCE: 610
aacccguaga uccgaucuug ug                                                      22

<210> SEQ ID NO 611
<211> LENGTH: 21
<212> TYPE: RNA
<213> ORGANISM: Artificial Sequence
<220> FEATURE:
<223> OTHER INFORMATION: Synthetic: mmu-miR-27a

<400> SEQUENCE: 611
uucacagugg cuaaguuccg c                                                       21

<210> SEQ ID NO 612
<211> LENGTH: 21
<212> TYPE: RNA
<213> ORGANISM: Artificial Sequence
<220> FEATURE:
<223> OTHER INFORMATION: Synthetic: mmu-miR-23a

<400> SEQUENCE: 612
aucacauugc cagggauuuc c                                                       21

<210> SEQ ID NO 613
<211> LENGTH: 22
<212> TYPE: RNA
<213> ORGANISM: Artificial Sequence
<220> FEATURE:
<223> OTHER INFORMATION: Synthetic: mmu-miR-26a

<400> SEQUENCE: 613
uucaaguaau ccaggauagg cu                                                      22

<210> SEQ ID NO 614
<211> LENGTH: 22
<212> TYPE: RNA
<213> ORGANISM: Artificial Sequence
<220> FEATURE:
<223> OTHER INFORMATION: Synthetic: mmu-miR-29a
```

-continued

```
<400> SEQUENCE: 614
uagcaccauc ugaaaucggu ua                                        22

<210> SEQ ID NO 615
<211> LENGTH: 23
<212> TYPE: RNA
<213> ORGANISM: Artificial Sequence
<220> FEATURE:
<223> OTHER INFORMATION: Synthetic: mmu-miR-10a

<400> SEQUENCE: 615
uacccuguag auccgaauuu gug                                       23

<210> SEQ ID NO 616
<211> LENGTH: 22
<212> TYPE: RNA
<213> ORGANISM: Artificial Sequence
<220> FEATURE:
<223> OTHER INFORMATION: Synthetic: mmu-miR-125b-5p

<400> SEQUENCE: 616
ucccugagac ccuaacuugu ga                                        22

<210> SEQ ID NO 617
<211> LENGTH: 22
<212> TYPE: RNA
<213> ORGANISM: Artificial Sequence
<220> FEATURE:
<223> OTHER INFORMATION: Synthetic: mmu-miR-484

<400> SEQUENCE: 617
ucaggcucag uccccucccg au                                        22

<210> SEQ ID NO 618
<211> LENGTH: 22
<212> TYPE: RNA
<213> ORGANISM: Artificial Sequence
<220> FEATURE:
<223> OTHER INFORMATION: Synthetic: mmu-miR-29c

<400> SEQUENCE: 618
uagcaccauu ugaaaucggu ua                                        22

<210> SEQ ID NO 619
<211> LENGTH: 22
<212> TYPE: RNA
<213> ORGANISM: Artificial Sequence
<220> FEATURE:
<223> OTHER INFORMATION: Synthetic: mmu-miR-100

<400> SEQUENCE: 619
aacccguaga uccgaacuug ug                                        22

<210> SEQ ID NO 620
<211> LENGTH: 22
<212> TYPE: RNA
<213> ORGANISM: Artificial Sequence
<220> FEATURE:
<223> OTHER INFORMATION: Synthetic: mmu-miR-199a-3p

<400> SEQUENCE: 620
acaguagucu gcacauuggu ua                                        22

<210> SEQ ID NO 621
<211> LENGTH: 22
```

```
<212> TYPE: RNA
<213> ORGANISM: Artificial Sequence
<220> FEATURE:
<223> OTHER INFORMATION: Synthetic: mmu-miR-22

<400> SEQUENCE: 621
aagcugccag uugaagaacu gu                                              22

<210> SEQ ID NO 622
<211> LENGTH: 22
<212> TYPE: RNA
<213> ORGANISM: Artificial Sequence
<220> FEATURE:
<223> OTHER INFORMATION: Synthetic: mmu-miR-21

<400> SEQUENCE: 622
uagcuuauca gacugauguu ga                                              22

<210> SEQ ID NO 623
<211> LENGTH: 23
<212> TYPE: RNA
<213> ORGANISM: Artificial Sequence
<220> FEATURE:
<223> OTHER INFORMATION: Synthetic: mmu-miR-107

<400> SEQUENCE: 623
agcagcauug uacagggcua uca                                             23

<210> SEQ ID NO 624
<211> LENGTH: 24
<212> TYPE: RNA
<213> ORGANISM: Artificial Sequence
<220> FEATURE:
<223> OTHER INFORMATION: Synthetic: mmu-miR-125a-5p

<400> SEQUENCE: 624
ucccugagac ccuuuaaccu guga                                            24

<210> SEQ ID NO 625
<211> LENGTH: 23
<212> TYPE: RNA
<213> ORGANISM: Artificial Sequence
<220> FEATURE:
<223> OTHER INFORMATION: Synthetic: mmu-miR-10b

<400> SEQUENCE: 625
uacccuguag aaccgaauuu gug                                             23

<210> SEQ ID NO 626
<211> LENGTH: 22
<212> TYPE: RNA
<213> ORGANISM: Artificial Sequence
<220> FEATURE:
<223> OTHER INFORMATION: Synthetic: mmu-miR-1274a

<400> SEQUENCE: 626
ucaggucccu guucaggcgc ca                                              22

<210> SEQ ID NO 627
<211> LENGTH: 22
<212> TYPE: RNA
<213> ORGANISM: Artificial Sequence
<220> FEATURE:
<223> OTHER INFORMATION: Synthetic: mmu-miR-28

<400> SEQUENCE: 627
```

-continued aaggagcuca cagucuauug ag                                                   22

<210> SEQ ID NO 628
<211> LENGTH: 22
<212> TYPE: RNA
<213> ORGANISM: Artificial Sequence
<220> FEATURE:
<223> OTHER INFORMATION: Synthetic: mmu-miR-25

<400> SEQUENCE: 628
cauugcacuu gucucggucu ga                                                   22

<210> SEQ ID NO 629
<211> LENGTH: 22
<212> TYPE: RNA
<213> ORGANISM: Artificial Sequence
<220> FEATURE:
<223> OTHER INFORMATION: Synthetic: mmu-miR-24

<400> SEQUENCE: 629
uggcucaguu cagcaggaac ag                                                   22

<210> SEQ ID NO 630
<211> LENGTH: 22
<212> TYPE: RNA
<213> ORGANISM: Artificial Sequence
<220> FEATURE:
<223> OTHER INFORMATION: Synthetic: mmu-miR-199b

<400> SEQUENCE: 630
acaguagucu gcacauuggu ua                                                   22

<210> SEQ ID NO 631
<211> LENGTH: 22
<212> TYPE: RNA
<213> ORGANISM: Artificial Sequence
<220> FEATURE:
<223> OTHER INFORMATION: Synthetic: mmu-let-7g

<400> SEQUENCE: 631
ugagguagua guuuguacag uu                                                   22

<210> SEQ ID NO 632
<211> LENGTH: 22
<212> TYPE: RNA
<213> ORGANISM: Artificial Sequence
<220> FEATURE:
<223> OTHER INFORMATION: Synthetic: mmu-let-7e

<400> SEQUENCE: 632
ugagguagga gguuguauag uu                                                   22

<210> SEQ ID NO 633
<211> LENGTH: 23
<212> TYPE: RNA
<213> ORGANISM: Artificial Sequence
<220> FEATURE:
<223> OTHER INFORMATION: Synthetic: mmu-miR-221

<400> SEQUENCE: 633
agcuacauug ucugcugggu uuc                                                  23

<210> SEQ ID NO 634
<211> LENGTH: 22
<212> TYPE: RNA
<213> ORGANISM: Artificial Sequence -continued
<220> FEATURE:
<223> OTHER INFORMATION: Synthetic: mmu-miR-2182

<400> SEQUENCE: 634
acgccacauu ucccacgccg cg                                                         22

<210> SEQ ID NO 635
<211> LENGTH: 22
<212> TYPE: RNA
<213> ORGANISM: Artificial Sequence
<220> FEATURE:
<223> OTHER INFORMATION: Synthetic: mmu-miR-450a-5p

<400> SEQUENCE: 635
uuuugcgaug uguuccuaau au                                                         22

<210> SEQ ID NO 636
<211> LENGTH: 21
<212> TYPE: RNA
<213> ORGANISM: Artificial Sequence
<220> FEATURE:
<223> OTHER INFORMATION: Synthetic: mmu-miR-222

<400> SEQUENCE: 636
agcuacaucu ggcuacuggg u                                                          21

<210> SEQ ID NO 637
<211> LENGTH: 23
<212> TYPE: RNA
<213> ORGANISM: Artificial Sequence
<220> FEATURE:
<223> OTHER INFORMATION: Synthetic: mmu-miR-29b

<400> SEQUENCE: 637
uagcaccauu ugaaaucagu guu                                                        23

<210> SEQ ID NO 638
<211> LENGTH: 22
<212> TYPE: RNA
<213> ORGANISM: Artificial Sequence
<220> FEATURE:
<223> OTHER INFORMATION: Synthetic: mmu-miR-350

<400> SEQUENCE: 638
uucacaaagc ccauacacuu uc                                                         22

<210> SEQ ID NO 639
<211> LENGTH: 21
<212> TYPE: RNA
<213> ORGANISM: Artificial Sequence
<220> FEATURE:
<223> OTHER INFORMATION: Synthetic: mmu-miR-703

<400> SEQUENCE: 639
aaaaccuuca gaaggaaaga a                                                          21

<210> SEQ ID NO 640
<211> LENGTH: 22
<212> TYPE: RNA
<213> ORGANISM: Artificial Sequence
<220> FEATURE:
<223> OTHER INFORMATION: Synthetic: mmu-miR-374

<400> SEQUENCE: 640
auauaauaca accugcuaag ug                                                         22

-continued

<210> SEQ ID NO 641
<211> LENGTH: 23
<212> TYPE: RNA
<213> ORGANISM: Artificial Sequence
<220> FEATURE:
<223> OTHER INFORMATION: Synthetic: mmu-miR-31*

<400> SEQUENCE: 641
ugcuaugcca acauauugcc auc                                                23

<210> SEQ ID NO 642
<211> LENGTH: 21
<212> TYPE: RNA
<213> ORGANISM: Artificial Sequence
<220> FEATURE:
<223> OTHER INFORMATION: Synthetic: mmu-miR-323-3p

<400> SEQUENCE: 642
cacauuacac ggucgaccuc u                                                  21

<210> SEQ ID NO 643
<211> LENGTH: 24
<212> TYPE: RNA
<213> ORGANISM: Artificial Sequence
<220> FEATURE:
<223> OTHER INFORMATION: Synthetic: mmu-miR-1949

<400> SEQUENCE: 643
cuauaccagg augucagcau aguu                                               24

<210> SEQ ID NO 644
<211> LENGTH: 22
<212> TYPE: RNA
<213> ORGANISM: Artificial Sequence
<220> FEATURE:
<223> OTHER INFORMATION: Synthetic: mmu-miR-470*

<400> SEQUENCE: 644
aaccaguacc uuucugagaa ga                                                 22

<210> SEQ ID NO 645
<211> LENGTH: 23
<212> TYPE: RNA
<213> ORGANISM: Artificial Sequence
<220> FEATURE:
<223> OTHER INFORMATION: Synthetic: mmu-miR-155

<400> SEQUENCE: 645
uuaaugcuaa uugugauagg ggu                                                23

<210> SEQ ID NO 646
<211> LENGTH: 23
<212> TYPE: RNA
<213> ORGANISM: Artificial Sequence
<220> FEATURE:
<223> OTHER INFORMATION: Synthetic: mmu-miR-466e-3p

<400> SEQUENCE: 646
uauacauaca cgcacacaua aga                                                23

<210> SEQ ID NO 647
<211> LENGTH: 21
<212> TYPE: RNA
<213> ORGANISM: Artificial Sequence
<220> FEATURE:
<223> OTHER INFORMATION: Synthetic: mmu-miR-152

-continued

<400> SEQUENCE: 647
ucagugcaug acagaacuug g                                                      21

<210> SEQ ID NO 648
<211> LENGTH: 23
<212> TYPE: RNA
<213> ORGANISM: Artificial Sequence
<220> FEATURE:
<223> OTHER INFORMATION: Synthetic: mmu-miR-34c

<400> SEQUENCE: 648
aggcagugua guuagcugau ugc                                                    23

<210> SEQ ID NO 649
<211> LENGTH: 21
<212> TYPE: RNA
<213> ORGANISM: Artificial Sequence
<220> FEATURE:
<223> OTHER INFORMATION: Synthetic: mmu-miR-702

<400> SEQUENCE: 649
ugcccacccu uuaccccgcu c                                                      21

<210> SEQ ID NO 650
<211> LENGTH: 23
<212> TYPE: RNA
<213> ORGANISM: Artificial Sequence
<220> FEATURE:
<223> OTHER INFORMATION: Synthetic: mmu-miR-96

<400> SEQUENCE: 650
uuuggcacua gcacauuuuu gcu                                                    23

<210> SEQ ID NO 651
<211> LENGTH: 22
<212> TYPE: RNA
<213> ORGANISM: Artificial Sequence
<220> FEATURE:
<223> OTHER INFORMATION: Synthetic: mmu-miR-542-3p

<400> SEQUENCE: 651
ugugacagau ugauaacuga aa                                                     22

<210> SEQ ID NO 652
<211> LENGTH: 20
<212> TYPE: RNA
<213> ORGANISM: Artificial Sequence
<220> FEATURE:
<223> OTHER INFORMATION: Synthetic: mmu-miR-805

<400> SEQUENCE: 652
gaauugauca ggacauaggg                                                        20

<210> SEQ ID NO 653
<211> LENGTH: 27
<212> TYPE: RNA
<213> ORGANISM: Artificial Sequence
<220> FEATURE:
<223> OTHER INFORMATION: Synthetic: mmu-miR-1944

<400> SEQUENCE: 653
cucugugcug aaugucaagu ucugauu                                                27

<210> SEQ ID NO 654

-continued

```
<211> LENGTH: 22
<212> TYPE: RNA
<213> ORGANISM: Artificial Sequence
<220> FEATURE:
<223> OTHER INFORMATION: Synthetic: mmu-miR-677

<400> SEQUENCE: 654
uucagugaug auuagcuucu ga                                            22

<210> SEQ ID NO 655
<211> LENGTH: 21
<212> TYPE: RNA
<213> ORGANISM: Artificial Sequence
<220> FEATURE:
<223> OTHER INFORMATION: Synthetic: mmu-miR-715

<400> SEQUENCE: 655
cuccgugcac acccccgcgu g                                             21

<210> SEQ ID NO 656
<211> LENGTH: 23
<212> TYPE: RNA
<213> ORGANISM: Artificial Sequence
<220> FEATURE:
<223> OTHER INFORMATION: Synthetic: mmu-miR-1839-3p

<400> SEQUENCE: 656
agaccuacuu aucuaccaac agc                                           23

<210> SEQ ID NO 657
<211> LENGTH: 23
<212> TYPE: RNA
<213> ORGANISM: Artificial Sequence
<220> FEATURE:
<223> OTHER INFORMATION: Synthetic: mmu-miR-19b

<400> SEQUENCE: 657
ugugcaaauc caugcaaaac uga                                           23

<210> SEQ ID NO 658
<211> LENGTH: 22
<212> TYPE: RNA
<213> ORGANISM: Artificial Sequence
<220> FEATURE:
<223> OTHER INFORMATION: Synthetic: mmu-miR-148a

<400> SEQUENCE: 658
ucagugcacu acagaacuuu gu                                            22

<210> SEQ ID NO 659
<211> LENGTH: 19
<212> TYPE: RNA
<213> ORGANISM: Artificial Sequence
<220> FEATURE:
<223> OTHER INFORMATION: Synthetic: mmu-miR-1937a

<400> SEQUENCE: 659
aaucccggac gagccccca                                                19

<210> SEQ ID NO 660
<211> LENGTH: 22
<212> TYPE: RNA
<213> ORGANISM: Artificial Sequence
<220> FEATURE:
<223> OTHER INFORMATION: Synthetic: mmu-miR-148b

<400> SEQUENCE: 660
```

-continued

```
ucagugcauc acagaacuuu gu                                           22

<210> SEQ ID NO 661
<211> LENGTH: 21
<212> TYPE: RNA
<213> ORGANISM: Artificial Sequence
<220> FEATURE:
<223> OTHER INFORMATION: Synthetic: mmu-miR-101a

<400> SEQUENCE: 661
uacaguacug ugauaacuga a                                            21

<210> SEQ ID NO 662
<211> LENGTH: 21
<212> TYPE: RNA
<213> ORGANISM: Artificial Sequence
<220> FEATURE:
<223> OTHER INFORMATION: Synthetic: mmu-miR-23b

<400> SEQUENCE: 662
aucacauugc cagggauuac c                                            21

<210> SEQ ID NO 663
<211> LENGTH: 21
<212> TYPE: RNA
<213> ORGANISM: Artificial Sequence
<220> FEATURE:
<223> OTHER INFORMATION: Synthetic: mmu-miR-872

<400> SEQUENCE: 663
aagguuacuu guuaguucag g                                            21

<210> SEQ ID NO 664
<211> LENGTH: 22
<212> TYPE: RNA
<213> ORGANISM: Artificial Sequence
<220> FEATURE:
<223> OTHER INFORMATION: Synthetic: mmu-miR-99b

<400> SEQUENCE: 664
cacccguaga accgaccuug cg                                           22

<210> SEQ ID NO 665
<211> LENGTH: 23
<212> TYPE: RNA
<213> ORGANISM: Artificial Sequence
<220> FEATURE:
<223> OTHER INFORMATION: Synthetic: mmu-miR-19a

<400> SEQUENCE: 665
ugugcaaauc uaugcaaaac uga                                          23

<210> SEQ ID NO 666
<211> LENGTH: 22
<212> TYPE: RNA
<213> ORGANISM: Artificial Sequence
<220> FEATURE:
<223> OTHER INFORMATION: Synthetic: mmu-miR-130a

<400> SEQUENCE: 666
cagugcaaug uuaaaagggc au                                           22

<210> SEQ ID NO 667
<211> LENGTH: 18
<212> TYPE: RNA
```

-continued

```
<213> ORGANISM: Artificial Sequence
<220> FEATURE:
<223> OTHER INFORMATION: Synthetic: mmu-miR-1937b

<400> SEQUENCE: 667
aucccggacg agcccca                                                        18

<210> SEQ ID NO 668
<211> LENGTH: 22
<212> TYPE: RNA
<213> ORGANISM: Artificial Sequence
<220> FEATURE:
<223> OTHER INFORMATION: Synthetic: mmu-let-7a*

<400> SEQUENCE: 668
cuauacaauc uacugucuuu cc                                                   22

<210> SEQ ID NO 669
<211> LENGTH: 22
<212> TYPE: RNA
<213> ORGANISM: Artificial Sequence
<220> FEATURE:
<223> OTHER INFORMATION: Synthetic: mmu-miR-30b

<400> SEQUENCE: 669
uguaaacauc cuacacucag cu                                                   22

<210> SEQ ID NO 670
<211> LENGTH: 22
<212> TYPE: RNA
<213> ORGANISM: Artificial Sequence
<220> FEATURE:
<223> OTHER INFORMATION: Synthetic: mmu-miR-16

<400> SEQUENCE: 670
uagcagcacg uaaauauugg cg                                                   22

<210> SEQ ID NO 671
<211> LENGTH: 22
<212> TYPE: RNA
<213> ORGANISM: Artificial Sequence
<220> FEATURE:
<223> OTHER INFORMATION: Synthetic: mmu-miR-30d

<400> SEQUENCE: 671
uguaaacauc cccgacugga ag                                                   22

<210> SEQ ID NO 672
<211> LENGTH: 22
<212> TYPE: RNA
<213> ORGANISM: Artificial Sequence
<220> FEATURE:
<223> OTHER INFORMATION: Synthetic: mmu-miR-30a

<400> SEQUENCE: 672
uguaaacauc cucgacugga ag                                                   22

<210> SEQ ID NO 673
<211> LENGTH: 21
<212> TYPE: RNA
<213> ORGANISM: Artificial Sequence
<220> FEATURE:
<223> OTHER INFORMATION: Synthetic: mmu-miR-101b

<400> SEQUENCE: 673
uacaguacug ugauagcuga a                                                    21
```

-continued

```
<210> SEQ ID NO 674
<211> LENGTH: 23
<212> TYPE: RNA
<213> ORGANISM: Artificial Sequence
<220> FEATURE:
<223> OTHER INFORMATION: Synthetic: mmu-miR-30c

<400> SEQUENCE: 674
uguaaacauc cuacacucuc agc                                              23

<210> SEQ ID NO 675
<211> LENGTH: 22
<212> TYPE: RNA
<213> ORGANISM: Artificial Sequence
<220> FEATURE:
<223> OTHER INFORMATION: Synthetic: mmu-miR-30e*

<400> SEQUENCE: 675
cuuucagucg gauguuuaca gc                                               22

<210> SEQ ID NO 676
<211> LENGTH: 21
<212> TYPE: RNA
<213> ORGANISM: Artificial Sequence
<220> FEATURE:
<223> OTHER INFORMATION: Synthetic: mmu-miR-27b

<400> SEQUENCE: 676
uucacagugg cuaaguucug c                                                21

<210> SEQ ID NO 677
<211> LENGTH: 22
<212> TYPE: RNA
<213> ORGANISM: Artificial Sequence
<220> FEATURE:
<223> OTHER INFORMATION: Synthetic: mmu-miR-30e

<400> SEQUENCE: 677
uguaaacauc cuugacugga ag                                               22

<210> SEQ ID NO 678
<211> LENGTH: 23
<212> TYPE: RNA
<213> ORGANISM: Artificial Sequence
<220> FEATURE:
<223> OTHER INFORMATION: Synthetic: mmu-miR-103

<400> SEQUENCE: 678
agcagcauug uacagggcua uga                                              23

<210> SEQ ID NO 679
<211> LENGTH: 22
<212> TYPE: RNA
<213> ORGANISM: Artificial Sequence
<220> FEATURE:
<223> OTHER INFORMATION: Synthetic: mmu-miR-15a

<400> SEQUENCE: 679
uagcagcaca uaaugguuug ug                                               22

<210> SEQ ID NO 680
<211> LENGTH: 22
<212> TYPE: RNA
<213> ORGANISM: Artificial Sequence
<220> FEATURE:
```

<223> OTHER INFORMATION: Synthetic: mmu-miR-194

<400> SEQUENCE: 680
uguaacagca acuccaugug ga                                          22

<210> SEQ ID NO 681
<211> LENGTH: 22
<212> TYPE: RNA
<213> ORGANISM: Artificial Sequence
<220> FEATURE:
<223> OTHER INFORMATION: Synthetic: mmu-miR-146b

<400> SEQUENCE: 681
ugagaacuga auuccauagg cu                                          22

<210> SEQ ID NO 682
<211> LENGTH: 22
<212> TYPE: RNA
<213> ORGANISM: Artificial Sequence
<220> FEATURE:
<223> OTHER INFORMATION: Synthetic: mmu-let-7i

<400> SEQUENCE: 682
ugagguagua guuugugcug uu                                          22

<210> SEQ ID NO 683
<211> LENGTH: 18
<212> TYPE: RNA
<213> ORGANISM: Artificial Sequence
<220> FEATURE:
<223> OTHER INFORMATION: Synthetic: mmu-miR-1937c

<400> SEQUENCE: 683
aucccggaag agccccca                                               18

<210> SEQ ID NO 684
<211> LENGTH: 21
<212> TYPE: RNA
<213> ORGANISM: Artificial Sequence
<220> FEATURE:
<223> OTHER INFORMATION: Synthetic: mmu-miR-140*

<400> SEQUENCE: 684
uaccacaggg uagaaccacg g                                           21

<210> SEQ ID NO 685
<211> LENGTH: 22
<212> TYPE: RNA
<213> ORGANISM: Artificial Sequence
<220> FEATURE:
<223> OTHER INFORMATION: Synthetic: mmu-miR-140

<400> SEQUENCE: 685
cagugguuuu acccuauggu ag                                          22

<210> SEQ ID NO 686
<211> LENGTH: 22
<212> TYPE: RNA
<213> ORGANISM: Artificial Sequence
<220> FEATURE:
<223> OTHER INFORMATION: Synthetic: mmu-miR-1839-5p

<400> SEQUENCE: 686
aagguagaua gaacaggucu ug                                          22

-continued

```
<210> SEQ ID NO 687
<211> LENGTH: 21
<212> TYPE: RNA
<213> ORGANISM: Artificial Sequence
<220> FEATURE:
<223> OTHER INFORMATION: Synthetic: mmu-miR-195

<400> SEQUENCE: 687
uagcagcaca gaaauauugg c                                              21

<210> SEQ ID NO 688
<211> LENGTH: 22
<212> TYPE: RNA
<213> ORGANISM: Artificial Sequence
<220> FEATURE:
<223> OTHER INFORMATION: Synthetic: mmu-miR-30a*

<400> SEQUENCE: 688
cuuucagucg gauguuugca gc                                             22

<210> SEQ ID NO 689
<211> LENGTH: 21
<212> TYPE: RNA
<213> ORGANISM: Artificial Sequence
<220> FEATURE:
<223> OTHER INFORMATION: Synthetic: mmu-miR-106b

<400> SEQUENCE: 689
uaaagugcug acagugcaga u                                              21

<210> SEQ ID NO 690
<211> LENGTH: 22
<212> TYPE: RNA
<213> ORGANISM: Artificial Sequence
<220> FEATURE:
<223> OTHER INFORMATION: Synthetic: mmu-miR-322

<400> SEQUENCE: 690
cagcagcaau ucauguuuug ga                                             22

<210> SEQ ID NO 691
<211> LENGTH: 19
<212> TYPE: RNA
<213> ORGANISM: Artificial Sequence
<220> FEATURE:
<223> OTHER INFORMATION: Synthetic: mmu-miR-684

<400> SEQUENCE: 691
aguuuucccu ucaagucaa                                                 19

<210> SEQ ID NO 692
<211> LENGTH: 21
<212> TYPE: RNA
<213> ORGANISM: Artificial Sequence
<220> FEATURE:
<223> OTHER INFORMATION: Synthetic: mmu-miR-653

<400> SEQUENCE: 692
guguugaaac aaucucuacu g                                              21

<210> SEQ ID NO 693
<211> LENGTH: 22
<212> TYPE: RNA
<213> ORGANISM: Artificial Sequence
<220> FEATURE:
<223> OTHER INFORMATION: Synthetic: mmu-miR-370
```

<400> SEQUENCE: 693
gccugcuggg guggaaccug gu                                                22

<210> SEQ ID NO 694
<211> LENGTH: 22
<212> TYPE: RNA
<213> ORGANISM: Artificial Sequence
<220> FEATURE:
<223> OTHER INFORMATION: Synthetic: mmu-miR-455*

<400> SEQUENCE: 694
uaugugccuu uggacuacau cg                                                22

<210> SEQ ID NO 695
<211> LENGTH: 22
<212> TYPE: RNA
<213> ORGANISM: Artificial Sequence
<220> FEATURE:
<223> OTHER INFORMATION: Synthetic: mmu-miR-190

<400> SEQUENCE: 695
ugauauguuu gauauauuag gu                                                22

<210> SEQ ID NO 696
<211> LENGTH: 22
<212> TYPE: RNA
<213> ORGANISM: Artificial Sequence
<220> FEATURE:
<223> OTHER INFORMATION: Synthetic: mmu-let-7c-1*

<400> SEQUENCE: 696
cuguacaacc uucuagcuuu cc                                                22

<210> SEQ ID NO 697
<211> LENGTH: 20
<212> TYPE: RNA
<213> ORGANISM: Artificial Sequence
<220> FEATURE:
<223> OTHER INFORMATION: Synthetic: mmu-miR-343

<400> SEQUENCE: 697
ucucccuuca ugugcccaga                                                   20

<210> SEQ ID NO 698
<211> LENGTH: 22
<212> TYPE: RNA
<213> ORGANISM: Artificial Sequence
<220> FEATURE:
<223> OTHER INFORMATION: Synthetic: mmu-miR-146a

<400> SEQUENCE: 698
ugagaacuga auuccauggg uu                                                22

<210> SEQ ID NO 699
<211> LENGTH: 21
<212> TYPE: RNA
<213> ORGANISM: Artificial Sequence
<220> FEATURE:
<223> OTHER INFORMATION: Synthetic: mmu-miR-219

<400> SEQUENCE: 699
ugauugucca aacgcaauuc u                                                 21

<210> SEQ ID NO 700
<211> LENGTH: 22

-continued

```
<212> TYPE: RNA
<213> ORGANISM: Artificial Sequence
<220> FEATURE:
<223> OTHER INFORMATION: Synthetic: mmu-miR-24-2*

<400> SEQUENCE: 700
gugccuacug agcugaaaca gu                                           22

<210> SEQ ID NO 701
<211> LENGTH: 23
<212> TYPE: RNA
<213> ORGANISM: Artificial Sequence
<220> FEATURE:
<223> OTHER INFORMATION: Synthetic: miR-34c-5p - UGUG

<400> SEQUENCE: 701
aggcagugug uguagcugau ugc                                          23

<210> SEQ ID NO 702
<211> LENGTH: 23
<212> TYPE: RNA
<213> ORGANISM: Artificial Sequence
<220> FEATURE:
<223> OTHER INFORMATION: Synthetic: miR-34c-5p-CAUG

<400> SEQUENCE: 702
aggcagugua guuagcucau ggc                                          23

<210> SEQ ID NO 703
<211> LENGTH: 23
<212> TYPE: RNA
<213> ORGANISM: Artificial Sequence
<220> FEATURE:
<223> OTHER INFORMATION: Synthetic: miR-34c-5p-CGGGAG

<400> SEQUENCE: 703
aggcagugua guuagcggga ggc                                          23

<210> SEQ ID NO 704
<211> LENGTH: 23
<212> TYPE: RNA
<213> ORGANISM: Artificial Sequence
<220> FEATURE:
<223> OTHER INFORMATION: Synthetic: miR-693-3p - mut

<400> SEQUENCE: 704
gcagcuuuca gaucuggcug uaa                                          23
```

TARGETING micro-RNAs FOR EXOSOMAL DELIVERY OR CELLULAR RETENTION

CROSS-REFERENCE TO RELATED APPLICATIONS

This application is a continuation of International Application No. PCT/US2019/043469 filed Jul. 25, 2019, which claims the benefit of U.S. Provisional Application No. 62/703,566 filed Jul. 26, 2018, the contents of which are incorporated herein by reference in their entirety.

STATEMENT OF FEDERAL FUNDING

This invention was made with government support under DK082659 awarded by the National Institute of Health. The government has certain rights in the invention.

BACKGROUND

Extracellular vesicles mediate cell to cell communication and are known to play a role in physiological and pathological processes. Extracellular vesicles may derive from the plasma membrane (e.g., microvesicles) or from the endosomal compartment (e.g., exosomes) and deliver their contents from origin to local or distant sites. microRNAs (miRNAs) are a class of non-coding RNAs that function as negative regulators of translation and are involved in many cellular processes. Exosomes carry mRNA, miRNA and other non-coding RNA that can be transferred to recipient cells. miRNAs were discovered in 1993 and are now known to mediate human disease. See Lee et al. (1993) Cell 75, 843-854. For example, it has been described that two human miRNA genes, mir-15a and mir-16-1, are downregulated or deleted in chronic lymphocytic leukemia (CLL). See Calin et al., Proc. Natl. Acad. Sci. USA (2002) 99, 15524-15529. In addition, miRNAs are being explored clinically for the treatment of hepatitis C virus (HCV) infection. See Lindow, M., and Kauppinen, S. (2012). J. Cell Biol. 199, 407-412.

Exosomes are extracellular lipid vesicles released by every cell. They contain several classes of macromolecules including DNA, mRNA, proteins and micro-RNAs (miR-NAs). Among all these molecules, exosomes seem to be particularly enriched in miRNAs. Exosomes have been demonstrated to be a very efficient delivery tool to transfer macromolecules to target cells where they can exert biological functions. For instance, exosomes can deliver miR-NAs to repress gene expression in the target cell.

Adipose tissue derived exosomes may have an especially potent effect in delivering miRNAs. Adipose tissue-derived miRNAs are released in vivo into the bloodstream and delivered to the liver, among many other potential tissue targets, where they can regulate hepatic expression of major metabolic genes such as fibroblast growth factor (FGF)-21 (see Thomou et al., *Nature,* 542:450-4555 (2017)).

Despite extensive work in the last years, it remains unclear how miRNAs are selected and sorted into exosomes. Santangelo and colleagues described a GGCU motif that can enrich exosomal sorting in the mouse hepatocyte 3A line (see Santangelo et al. *Cell Reports* 17:799-808 (2016)), and Villarroya-Beltri and colleagues described a GGAG motif that can enrich exosomal sorting in in human lymphoblasts (see Villarroya-Beltri et al. *Nature Communications* 2980 (2013)). However, it is not yet clear whether exosomal sorting motifs can be broad to control sorting in a wide range of cells or alternatively if specific exosomal sorting can be cell-selective and limit sorting in only specific types of cells.

The present application describes exosomal sorting and retention motifs that can be used therapeutically to direct miRNAs to desired cellular locations. Described herein are mechanisms that govern the selection of miRNAs into exosomes in a panel of different cell lines. Exosomal sorting motifs showed different levels of enrichment in individual cell lines, meaning that a sorting motif can be optimized to engineer artificial miRNAs by adding or removing a sequence specific to a particular cell type of interest. Similarly, motifs can be engineered to avoid exosomal sorting in particular cell types.

SUMMARY

In accordance with the description, this study analyzed miRNA motifs responsible for exosomal sorting or cellular retention in different cell lines. Five different mouse cell lines resembling major metabolic cells were cultured in vitro: 3T3-L1 (white adipocytes), BAT (brown adipocytes), C2C12 (muscle cells), AML12 (hepatocytes), and SVEC (vascular endothelial cells). Exosomes and cell lysates were collected, and miRNA profiling was performed to analyze miRNA expression. Motifs that regulate sorting of miRNAs into exosomes in cell-specific manner were determined. Conversely, motifs are described that limit exosomal sorting and enrich retention of miRNAs in the cell.

In some embodiments, a method for producing miRNA-containing exosomes or exosome-like vesicles in vitro is provided comprising the steps of modifying a miRNA to include at least one exosomal sorting motif and/or removing any cellular retention motifs, and introducing the modified miRNA into a cell that produces exosomes or exosome-like vesicle under conditions that will result in expression of the modified miRNA. The exosomal sorting motif is selected from UGUG, GGAG, CAUG, GGCA/G, A/CGGG, CUGG, and CGGGAG. The cellular retention motif is selected from CAGU, ACAG, AUUG, UAGC, and CCCG. In some embodiments, the method further comprises collecting the produced exosomes or exosome-like vesicles that contain the modified miRNA.

In some embodiments, the exosomal sorting motif is UGUG.

In some embodiments, the exosomal sorting motif is GGAG.

In some embodiments, the exosomal sorting motif is CAUG.

In some embodiments, the exosomal sorting motif is GGCA/G.

In some embodiments, the exosomal sorting motif is A/CGGG.

In some embodiments, the exosomal sorting motif is CUGG.

In some embodiments, the exosomal sorting motif is CGGGAG.

In some embodiments, the miRNA comprises one exosomal sorting motif. In some embodiments, the miRNA comprises more than one exosomal sorting motif.

In some embodiments, subjects are intravenously injected or otherwise administered culture-derived exosomes containing a miRNA of interest and these exosomes deliver their miRNA cargo to a target cell, leading to the reduction of the expression of the gene of interest. In order to induce or increase the export of the desired miRNA to the exosomes, an exosomal sorting motif can be inserted in, or appended to, the miRNA sequence in the cultured cells and/or a cell retention motif removed. In fact, as different cell types seem to have different usage of the motifs (as shown in FIG. 4), the exosomal enrichment may be further optimized by inserting the specific motif that this particular cell type preferentially uses to export its miRNAs. If the miRNA of interest contains a cellular retention motif, this sequence can be removed and replaced by an exosome-enrichment motif, without which exosomal enrichment and potential clinical use might be very limited.

Therefore, in some embodiments, the method described above further comprises administering the exosome or exosome-like vesicle to a subject.

Therapeutically, exosomes loaded with particular miR-NAs may be used to treat diseases where decreasing the expression of a target gene is desired, such as oncogenes in cancer, or inflammatory, lipogenesis- or gluconeogenis-promoting genes in obesity and type 2 diabetes. Thus, in some embodiments, a method of treating a subject in need of gene silencing is provided comprising administering to the subject an exosome, wherein the exosome is produced in vitro by a) modifying a miRNA to include at least one exosomal sorting motif and/or removing any cellular retention motifs, and b) introducing the modified miRNA into a cell that produces exosomes or exosome-like vesicles under conditions that will result in expression of the modified miRNA, and collecting the produced exosome comprising the modified miRNA, wherein the exosomal sorting motif is selected from UGUG, GGAG, CAUG, GGCA/G, A/CGGG, CUGG, and CGGGAG and the cellular retention motif, if present, is selected from CAGU, ACAG, AUUG, UAGC, and CCCG.

In some embodiments, modifying the miRNA with an exosomal sorting motif results in more miRNA in the exosome as compared to an exosome produced with a miRNA not modified with an exosomal sorting motif. In some embodiments, the removal of the cellular retention motif results in more miRNA in the exosome as compared to an exosome produced with a miRNA comprising a cellular retention motif.

In some embodiments, the miRNA contains a cellular retention motif and the cellular retention motif is removed.

Conversely, other applications might require miRNA production and retention into the cell. For instance, ex vivo cellular therapies imply the induction of the expression of genes in cells isolated from patients and later reintroduction of those back into the patient. If that gene is a miRNA, a cellular retention motif may be incorporated into its sequence in order to optimize the number of miRNAs that will be retained in the cells and reduce as much as possible its loss through exosomal secretion. In addition, this strategy may reduce the effect in other cells different from the transplanted by limiting the export and transfer of the inserted miRNA to other cells in the organism through exosomes when they are introduced back to the patient.

Thus, in some embodiments, a method for retaining miRNA inside a cell in vitro is provided comprising modifying a miRNA to include at least one cell retention motif and/or removing any exosomal sorting motifs, and introducing the modified miRNA into a cell that produces an exosome or exosome-like vesicle under conditions that will result in expression of the modified miRNA, wherein the cell retention motif is CAGU, ACAG, AUUG, UAGC, or CCCG, and the exosomal sorting motif, if present, is UGUG, GGAG, CAUG, GGCA/G, A/CGGG, CUGG, or CGGGAG.

In some embodiments, a method of treating a subject in need of gene silencing is provided comprising collecting the subject's cells and manipulating them ex vivo to express an miRNA having at least one cellular retention motif and/or removing any exosomal sorting motifs, and b) administering the ex vivo manipulated cell comprising the modified miRNA to the same or different subject from which it was collected, wherein the cellular retention motif is selected from CAGU, ACAG, AUUG, UAGC, and CCCG, and the exosomal sorting motif, if present, is selected from UGUG, GGAG, CAUG, GGCA/G, A/CGGG, CUGG, and CGG-GAG.

In some embodiments, the cellular retention motif is CAGU.

In some embodiments, the cellular retention motif is ACAG.

In some embodiments, the cellular retention motif is AUUG.

In some embodiments, the cellular retention motif is UAGC.

In some embodiments, the cellular retention motif is CCCG.

In some embodiments, the miRNA comprises one cellular retention motif. In some embodiments, the miRNA comprises more than one cellular retention motif.

In some embodiments, the addition of the cellular retention motif reduces the export of the miRNA into an exosome or exosomal-like vesicle. In some embodiments, the removal of the exosomal sorting motif reduces the export of the miRNA into an exosome or exosomal-like vesicle.

In some embodiments, the method further comprises administering the cell to a subject.

In some embodiments, the miRNA levels in non-implanted cell-types after administration to the subject are reduced as compared to levels in subject administered a non-modified miRNA containing cell.

In some embodiments, the cell is an adipocyte, muscle cell, hepatocyte, or vascular endothelial cell. In some embodiments, the adipocyte is a white adipocyte or brown adipocyte. In some embodiments, the white adipocyte is a 3T3-L1 cell. In some embodiments, the brown adipocyte is a BAT cell. In some embodiments, the muscle cell is a C2C12 cell. In some embodiments, the hepatocyte is an AML12 cell. In some embodiments, the vascular endothelial cell is a SVEC cell.

In some embodiments when the cell is a hepatocyte or endothelial cell, the sorting motifs are A/CGGG; CUGG; GGAG; and CGGGAG.

In some embodiments when the cell is a brown adipocyte, white adipocyte, or muscle cell, the exosomal sorting motifs are UGUG; CAUG; CUGG; and CGGGAG.

In some embodiments, the miRNA is any one of the miRNAs of SEQ ID Nos: 1-704.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 2A-2E shows analysis of the exosome- and cell lysate-enriched miRNAs for each cell type. The cell lysate refers to the lysate generated from the cell pellet. Most of the miRNAs are specifically found only in the exosomes or in the cell lysate, suggesting the existence of a selective mechanism for exosomal sorting of miRNAs that varies for every cell type. Each cell type also had a smaller number of miRNAs that were present in both the exosome and in the cell lysate (shown in the overlapping region of the exosome and lysate fractions). In some cases, miRNAs detected in exosomes where not detected in the cell lysate and vice-versa; therefore, the total number of miRNAs for each cell type may not match the values in FIG. 1.

FIGS. 4A and 4B show the main nucleotide motifs significantly enriched in miRNAs that are preferentially sorted into exosomes (FIG. 4A) or retained in cells (FIG. 4B). The numbers in the table indicate the percentage of miRNAs containing those motifs in each cell type. The presence of two nucleotides at a position means miRNAs were enriched when they contained a motif with either nucleotide at that position. The "total" value represents the percentage of miRNAs from each cell types that contained at least one of the motifs. Some miRNAs contained more than one motif. In this situation, the miRNA is only counted once for the total value, whereas it is counted in both columns referring to those two individual motifs.

FIGS. 5A-5E shows the main nucleotide motifs significantly enriched in miRNAs that preferentially are sorted to exosomes or retained in the cell and the number of miRNAs containing that sequence. The numbers in the left column indicate the order of abundance.

FIG. 6A shows the name, mature miRNA sequence, and introduced motif for the new miRNA constructs from miR-34c-5p and its wild-type version. Bold underlined text indicate nucleotides that were replaced. The miRNA constructs tested were miR-34c-5p wt (SEQ ID NO: 648), miR-34c-5p-UGUG (SEQ ID NO: 701), miR-34c-5p-CAUG (SEQ ID NO: 702), and miR-34c-5p-CGGGAG (SEQ ID NO: 703). FIG. 6B shows the predicted hairpin structure upon the nucleotide replacements (arrows) in the changes in the nucleotides in the guide strand (described in FIG. 6A) and the passenger strand. High pairing possibility between nucleotides is shown in black, while low pairing probability in gray. FIG. 6C shows exosomal enrichment measured as the difference between normalized expression of each miRNA version in exosomes divided by the normalized expression in the cell. In both exosomes and cells, expression was normalized in respect to miR-138b-5p, which was shown to be equally abundant in both exosomes and cells. *P-value<0.05.

FIG. 6D shows the name, mature miRNA sequence, and introduced motif for a new miRNA construct miR-693-3p-mut (SEQ ID NO: 704) and wild-type miR-693-3p (SEQ ID NO: 6). Bold underlined text indicates the nucleotide that was replaced. FIG. 6E shows the predicted hairpin structure for miR-693-3p wild-type and the mutated version upon the nucleotide replacements (arrow) in the changes in the nucleotides in the guide strand (described in FIG. 6D) and the passenger strand. High pairing possibility between nucleotides is shown in black, while low pairing probability in gray. FIG. 6F shows exosomal enrichment measured as the difference between normalized expression of each miRNA version in exosomes divided by normalized expression in the cell. In both exosomes and cells, expression was normalized in respect to miR-138b-5p. **P-value<0.01.

DESCRIPTION OF THE EMBODIMENTS

Figure 1A:
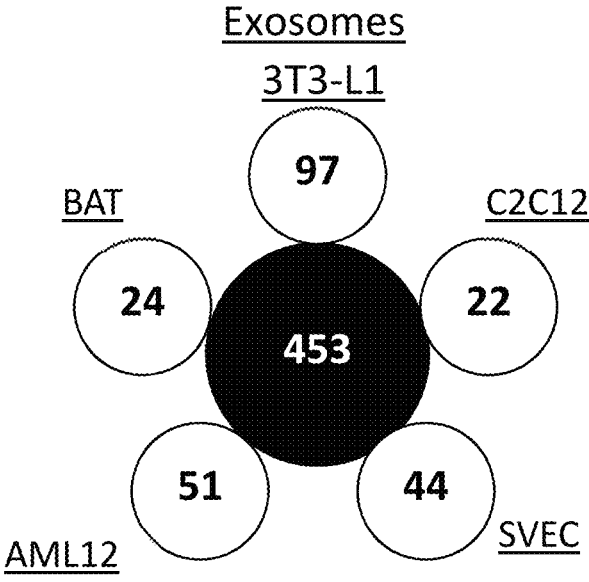
FIGS. 1A-1D show comparisons of miRNAs among the different cell lines both in the exosomes and cell pellets. By comparing the expression of each miRNA in each cell line with respect to the other four, several cell-type enriched miRNAs for each cell type were identified (shown as outer circles labeled with cell type) in exosomes (FIG. 1A) and in the cell pellets (FIG. 1C). Other miRNAs were not particularly enriched in any of the studied cell lines (shown as large inner circles). The top-10 enriched miRNAs for each type in the exosomes (FIG. 1B) and cell pellets (FIG. 1D) are shown.

"Exosomes" as used herein are membrane-surrounded, endosomal-derived vesicles that are present in many biological fluids, including blood, urine, and cultured medium of cell cultures. Exosomes may also be referred to as secreted vesicles. It will be understood that exosomes as described herein may, in certain non-limiting embodiments, also encompass exosome-like vesicles that may vary somewhat from typical exosomes but are still functionally and/or structurally similar or related. Reference to exosome-producing cells herein may include other suitable exosome-like vesicle-producing cells which produce exosome-like vesicles which may vary somewhat from typical exosomes but are still functionally and/or structurally similar or related. For instance, exosomes as described herein may include, in certain non-limiting embodiments, other suitable exosome-like vesicles between 50-150 nm (which contain exosomal markers), and/or larger exosome-like vesicles of 100-600 nm.

"microRNA" or "miRNA" as used herein refers to small non-coding RNA molecules that are evolutionary conserved. miRNAs are naturally occurring in an organism. Alternatively, a miRNA may be designed artificially and not be present in any organism. A miRNA may be chemically modified, for example, to improve stability. A miRNA may affect RNA silencing and post-transcriptional regulation of gene expression.

"Protein" as used herein, is a protein, polypeptide, or peptide. As such, a "protein" as used in this application may refer to only a portion of a full-length protein that is the product of a gene.

"Cell (or cellular) retention motif," as used herein, refers to a sequence of nucleotides that when naturally or artificially present or appended to a miRNA cause the miRNA to be substantially retained in the endosome.

"Exosome (or exosomal) sorting motif," as used herein, refers to a sequence of nucleotides that when naturally or artificially present or appended to a miRNA cause the miRNA to be substantially present or exported to or into an exosome.

miRNA constructs (also sometimes referred to herein as "miRNA") as described herein may be chemically synthesized using, for example, solid phase synthesis, or other methods known in the art. miRNA may also be prepared by cellular or in vitro expression from a suitable expression vector as will be known in the art. Variants, chemically modified analogues, and structural mimics of miRNA as described herein may also be possible.

miRNA constructs may be introduced into a cell, expressed in a cell, or caused to be produced by a cell, using any of a number of well-known methods. Introduction of a miRNA into a cell may include expression of the nucleic acid construct within a cell using a method as described herein, or using a suitable method known in the art, and/or may include direct introduction of the miRNA construct into the cell via, for example, transfection. Expression vectors (either viral, plasmid, or other) may be transfected, electroporated, or otherwise introduced into cells, which may then express the miRNA construct(s). Alternatively, nucleic acid constructs themselves may be directly introduced into cells, for example via transfection or electroporation (i.e. using a transfection reagent such as but not limited to Lipofectamine™, Oligofectamine, or any other suitable delivery agent known in the art), or via targeted gene or nucleic acid delivery vehicles known in the art. Many delivery vehicles and/or agents are well-known in the art, several of which are commercially available. Delivery strategies for nucleic acids are described in, for example, Yuan et al., Expert Opin. Drug Deliv. (2011) 8:521-536; Juliano et al, (2012) Acc. Chem. Res. 45: 1067-1076; and Rettig et al. Mol. Ther. (2012) 20: 483-512. Examples of transfection methods are described in, for example, Ausubel et al. (1994) Current Protocols in Molecular Biology, John Wiley & Sons, New York. Expression vector examples are described in, for example, Cloning Vectors: A Laboratory Manual (Pouwels et al., 1985, Supp. 1987). It will be understood that introduction of a nucleic acid construct into a cell may refer to the production of a nucleic acid within a cell from a gene (i.e. transcription), such an exogenous gene which has been introduced into the cell.

In some embodiments, a cell already expresses a miRNA and that miRNA is modified in vitro to contain an exosomal sorting or cellular retention motif.

In some embodiments, the miRNA comprises a native sequence that is present in the subject organism. In some embodiments, the miRNA does not comprise a native sequence. In some embodiments, the miRNA is non-natural.

In some embodiments, the miRNA is non-naturally prepared ex vivo. In some embodiments, the miRNA alters gene function.

Autologous or heterologous exosomes may be prepared.

In some embodiments, autologous exosomes are prepared. "Autologous exosomes" refers to exosomes that are prepared from the same subject who would receive the exosomes after ex vivo manipulation.

In some embodiments, heterologous exosomes are prepared. "Heterologous exosomes" refer to exosomes that are prepared from a different individual than the subject who receives the exosomes after ex vivo manipulation.

In some embodiments, the exosomes are produced by cells in vitro. In some embodiments, the isolated exosomes are formed inside the cell in compartments known as multivesicular endosomes (MVE) or multivesicular body (MVB). In some embodiments, exosomes are released from a cell without a trigger or signal. In some embodiments, exosomes are released from a cell based on a signal, such as binding of a cell-surface receptor.

In some embodiments, exosomes are approximately 30 to 100 nm, 20 to 90 nm, 30 to 80 nm, 40 to 70 nm, or 50 to 60 nm. In some embodiments, exosomes are approximately 30, 40, 50, 60, 70, 80, 90, 100, 110, 120, 130, 140, 150, or 200 nm in size.

In some embodiments, the exosomes are derived from adipose tissue. In some embodiments, exosomes secreted from fat or adipose tissue may be termed fat-derived exosomes. In some embodiments, this adipose tissue can be inguinal, epididymal, or brown adipose tissue (BAT). In some embodiments, this adipose tissue can be brown fat, beige fat, or white fat.

In some embodiments, an exosome is derived from BAT tissue. In some embodiments, BAT is characterized by numerous small lipid droplets and a higher concentration of mitochondria compared with white fat. In some embodiments, BAT occurs in high concentrations in certain anatomical locations, such as between the shoulder blades, surrounding the kidneys, the neck and supraclavicular area, and along the spinal cord. In some embodiments, BAT occurs in the upper chest and neck, especially paravertebrally.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1. Cell Lines

This study analyzed 5 different mouse cell lines resembling major metabolic cells: 3T3-L1 (white adipocytes), BAT (brown adipocytes), C2C12 (muscle cells), AML12 (hepatocytes) and SVEC (vascular endothelial cells).

3T3-L1 cells (ATCC, catalog nr CL-173) were grown in growth medium (DMEM-high glucose supplemented with 10% fetal bovine serum, 1% penicillin/streptomycin, and 0.2% normocin). For the experiments, cells were grown to reach full confluence and differentiated to mature adipocytes. Upon addition of differentiation cocktail containing 0.5 mM IBMX, insulin 5 µg/mL and dexamethasone 0.25 µM in growth medium for 72 hours, cells were maintained in growth medium only supplemented with insulin 5 µg/ml for 8 days to obtain fully differentiated adipocytes.

Brown pre-adipocytes (BAT) were generated as described previously (Fasshauer M et al., *J Biol Chem* 275(33):25494-501 (2000)) and grown in DMEM-high glucose, 20% fetal bovine serum, 1% penicillin/streptomycin and 0.2% normocin. For the experiments, cells were grown to full confluence and differentiated to mature brown adipocytes. To induce differentiation, cells were incubated for 24 hours in growth medium supplemented with 0.5 mM IBMX, 0.125 mM indomethacin, 2 μg/ml dexamethasone, 20 nM insulin, and 1 nM T3 hormone. After that, cells were grown in culture medium only supplemented with 20 nM insulin and 1 nM T3 for 6 days. All reagents for 3T3-L1 and BAT differentiation were purchased from Millipore-Sigma.

AML12 hepatocytes were purchased from ATCC (catalog nr CRL-2254) and grown in DMEM/F12 high glucose, 10% fetal bovine serum, 1% penicillin/streptomycin and 0.2% normocin supplemented with insulin-transferrin-selenium-sodium pyruvate mixture (ITS-A, Thermofisher), 2.5 mM L-Glutamine (Thermofisher), 15 mM HEPES (Millipore-Sigma) and dexamethasone 40 ng/ml.

SVEC endothelial cells were purchased from ATCC (catalog nr CRL-2181) and cultured in growth medium.

C2C12 myoblasts (ATCC, catalog nr CRL-1772) were grown in growth medium. Upon confluence, cells were differentiated by growing the cells in DMEM-high glucose supplemented with 2% horse serum, 1% penicillin/streptomycin and 0.2% normicin for 6 days and used for the experiments.

Example 2. Exosome Isolation and Analysis

For exosome isolation, all cell lines cells were grown to full confluence. When cells required differentiation (3T3-L1, BAT, and C2C12), they were differentiated as described in Example 1. To collect exosomes, cells were washed with PBS and incubated for 72 hours in exosome-free medium consisting of DMEM-high glucose, 10% exosome-depleted fetal bovine serum (SBI), and 1% penicillin/streptomycin. Medium was collected and exosomes were isolated by differential centrifugation protocol (Thery C et al., *Curr Protoc Cell Biol Chapter* 3: Unit 3.22 (2006)). Briefly, medium was successively centrifuged at 500 g, 2,000 g and 10,000 g. Supernatant was later ultracentrifuged at 100,000 g for 70 min using a SW-28 rotor. Pellets were washed with PBS and centrifuged again at 100,000 g for 70 min. Pellets were resuspended in 1 mL TRIzol reagent (Thermofisher) to generate a cell lysate for further RNA isolation.

Similarly, cells that had produced the exosomes were washed with PBS after the incubation in exosome-free medium and 1 mL TRIzol reagent was added for further RNA isolation. This sample represents the cell lysate.

For RNA isolation and miRNA profiling, samples in TRIzol were added to 200 μL chloroform (Millipore-Sigma). After mixing, samples were centrifuged at 12,000 g for 15 min. Upper liquid phase was collected and RNA was precipitated by adding 2-propanol (Millipore-Sigma) and ammonium acetate (Millipore-Sigma) and incubating at −20° C. overnight. Samples were centrifuged at 12,000 g for 30 min and RNA pellets were washed twice with 70% ethanol and resuspended in nuclease-free water (Qiagen). Both exosomal and cell pellet miRNA profilings were performed using a mouse a QuantiMir for cDNA synthesis (SBI) and miRNome miRNA profiling kit (SBI) following manufacturer's protocol. RNA amount used for the experiment was 275 ng per sample.

For bioinformatic analysis, an arbitrary threshold (80) was used to extract ct value from the qPCRs. Samples that did not have ct value<=35 in at least 2 of the replicates for a given miRNA were considered non-detected and therefore filtered out. Ct values were normalized using mean ct of all detected miRNAs of each sample. Package Limma for R software (Ritchie M E et al., *Nucleic Acids Research* 43(7), e47 (2015)) was used for the analysis. Bioinformatics was used to compare the normalized expression in the cell and in the exosome of each given miRNAs with a false discovery rate (FDR) of <0.1. When the FDR for a given miRNA was <0.1, it was considered significant.

Example 3. Identification of Cell Type-Enriched miRNAs in Exosomal and Cellular Fractions Cells described in Example 1 were cultured in exosome-free medium, and exosomes were collected from the medium after 72 hours. RNA was isolated from the collected exosomes as well as from the cell pellets, converted to cDNA and subjected to a qPCR-based miRNA profiling to detect miRNA expression.

Figure 1B:
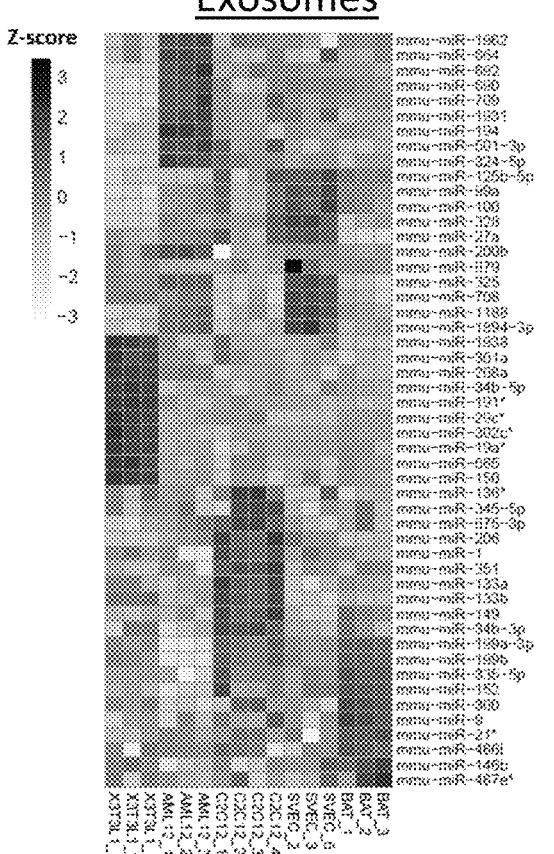
Figure 1C:
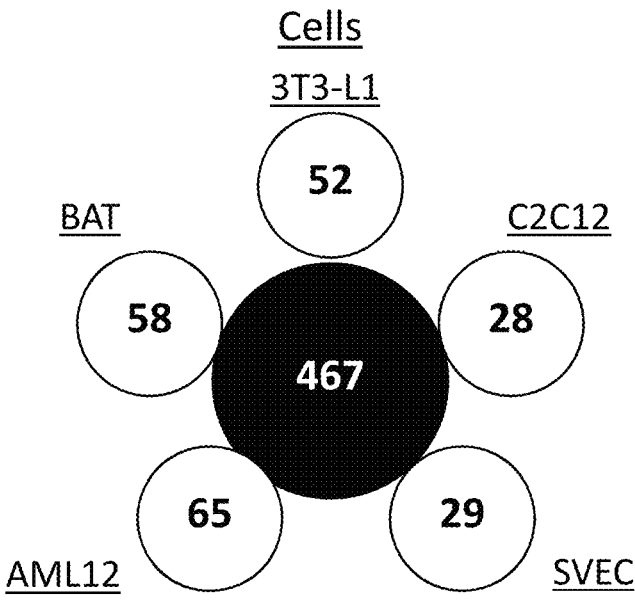

Among the 709 mouse miRNAs analyzed included in the miRNA profiling kit, 697 were detected in at least one of the cell types. By comparing the expression of each miRNA in each cell type to the expression in the other four, several miRNAs were identified that were particularly enriched in the exosomes derived from one of the cell types. FIGS. 1A (exosomes) and 1C (cell pellets) shows overall counts of miRNAs that had enrichment in a particular cell type. The outer circles in FIGS. 1A and 1C show the number of miRNAs with enrichment in a particular cell type. Similarly, some other miRNAs were found selectively in the cell pellets from one particular cell type.

Figure 1D:
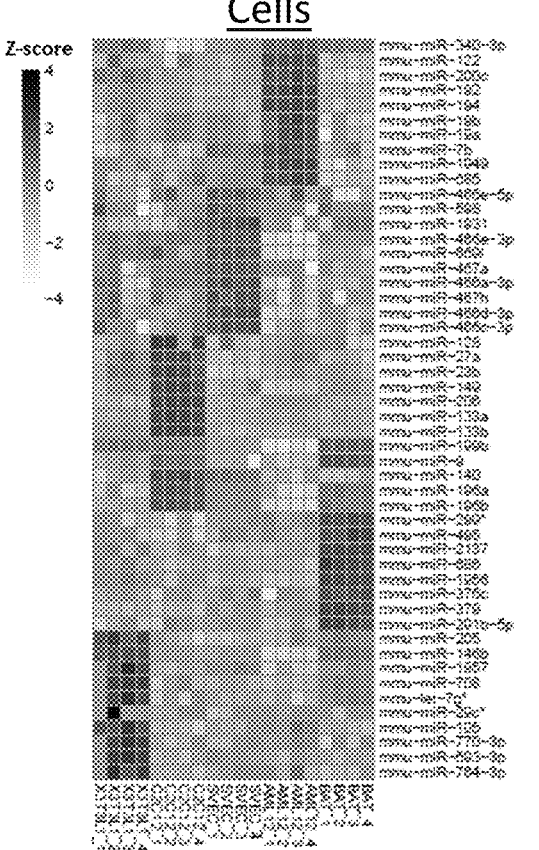

The top-10 enriched miRNAs for each cell type in exosomes (FIG. 1B) and cell pellets (FIG. 1D). Different cell types had different miRNAs with higher enrichment, and miRNAs that were enriched in one particular cell type were not necessarily highly expressed in other cell types.

As expected, most measured miRNAs were not uniquely representative of one of the cell types either in the exosomal (453 miRNAs) or in the cellular fraction (467 miRNAs) (FIGS. 1A and 1C). Some of the cell-enriched miRNAs were previously reported to mediate important functions in the tissues that these cells resemble. For instance, miR-19a and miR-122 that were significantly higher in AML12 hepatocytes (FIGS. 1B and 1D) are known to be expressed in mouse liver where they regulate glycogen synthesis and lipid metabolism, respectively (see Dou L et al., *Sci Rep* 26(5):11602 (2015) and Esau C et al., *Cell Metab* 3(2):87-98 (2006)). Other examples are miR-1 and miR-133a/b that were found to be enriched in C2C12 myotubes and previously reported to mediate crucial functions in skeletal muscle and heart (see Zhao Y et al., Cell 129(2):303-317 (2007) and Chen J F et al., *Nat Genet* 38(2):228-33 (2006)). Similarly, miR-146b seems to activate adipogenesis and was enriched in 3T3-L1 adipocytes (see Ahn J et al., *EMBO Mol Med* 10:1602-12 (2013)). All these data suggest that this study efficiently identified cell-type enriched miRNAs and that the cell lines used here resemble metabolic distinct tissues.

After identifying exosome and cell pellet-specific miRNAs, the miRNA population contained in the exosomes was compared to the cellular content of each cell type. If exosomes simply represent a sample of the miRNAs that are found in the cell, there should be a perfect match between the specific miRNAs found in exosomes and the cell pellets for each cell type. If, in contrast, there is selectivity in the loading of exosomes, populations of exosomal and cellular miRNAs would be at least partially different.

As shown in FIGS. 2A-2E, there is an incomplete match in the miRNA population between exosome and cell lysate samples from each cell type. Some miRNAs are cell type-specific regarding both compartments, as shown by the number of miRNAs contained in the region of overlap between the exosome and lysate samples for each cell type.

However, many other miRNAs were selectively found in the cellular or in the exosome fraction of a given cell type, and they were not specifically found in the other fraction. These data suggest the presence of a sorting mechanism of miR-NAs into exosomes that is specific for one cell type versus another.

Example 4. Enrichment and Depletion of miRNAs from Exosomes

Figure 3:
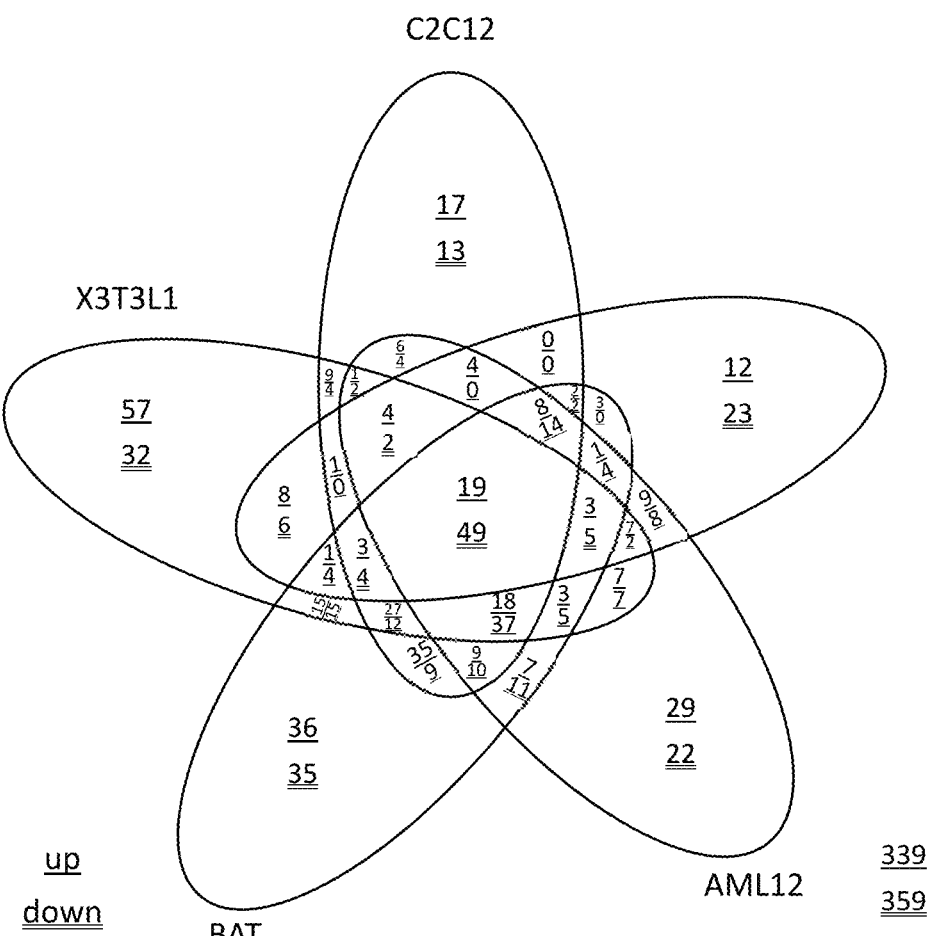
FIG. 3 shows a Venn diagram representing the number of miRNAs with a significant exosomal enrichment (top ["up"] numbers) or cellular enrichment (bottom ["down"] numbers) in each cell type. Overlapping regions indicate the number of miRNAs showing similar enrichment in more than one cell type.

In order to understand how some miRNAs are preferentially loaded into the exosomes whereas others preferentially remain in the cell, the expression of each particular miRNA was compared between the exosomal and the cellular fraction. This approach allowed separation of miRNAs that are particularly enriched in the exosomes compared to the cells where they were produced (expression in exosomes would be significantly higher than in the cell), or in contrast miRNAs that are enriched in the cell pellets but rarely go to the exosomes (expression significantly lower in the exosomes than in the cell). As shown in FIG. 3, miRNAs were identified with a significant enrichment in the exosomes (top ["up"] values) or in the cell pellet (bottom ["down"] values) in each cell type. The sorting into up and down groups was done by comparing the normalized expression of a miRNA in the exosome (measured by comparing to the mean of all detected miRNAs) to the normalized expression in the cell pellet. For a miRNA to be placed "up", it needed to have a significant higher expression in the exosome compared to cell lysate as determined by a cut-off<0.1 in the false discovery rate. Similarly for a miRNA to be placed "down," it needed to have a significant higher expression in the cell pellet compared to cell lysate as determined by a cut-off<0.1 in the false discovery rate.

A total of 19 miRNAs were identified that were significantly enriched in the exosomes from every cell type, and 49 miRNAs were identified that were significantly depleted from the exosomes of all cell lines analyzed in this study; these data are shown in the center values that overlapped between all cell types. Another interesting finding is the high degree of similarity between brown adipocytes (BAT) and muscle cells (C2C12) regarding which miRNAs are enriched or depleted in the exosomes (FIG. 3), as represented by the high number of miRNAs (35) enriched in exosomes shared by both cell types. Similarly, the number of miRNAs (27) in the intersection of BAT, C2C12, and 3T3-L1 cells is also high, which further contributes to the finding of similarity in enrichment data between BAT and C2C12 cells.

Example 5. Identification of RNA Motifs Associated with Exosomal or Cellular miRNA Enrichment in Different Cell Types The potential mechanism that made some miRNAs preferentially sorted to exosomes or be retained in the cell was explored. In particular, nucleotide sequences of the miRNAs were investigated to determine if they could determine the fate of the sorting.

Table 1 shows all detected miRNAs and their mature sequences. The code 1 indicates significant enrichment of that miRNA expression in exosomes from the cell type referred in the column, code −1 indicates significant cell enrichment, and code 0 indicates no difference between exosomal and cellular expression. The identified exosomal enrichment motifs are highlighted in bold whereas the cellular enrichment motifs are underlined. Some miRNAs did not comprise either an exosomal sorting motif or a cellular retention motif. Some miRNAs comprised both an exosomal sorting motif and in a cellular retention motif. Nucleotides that were within both an exosomal sorting and within a cellular retention motif are noted with bold underlined font.

TABLE 1

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 1 | gggggucccc<u>ggugcucggauc</u> | mmu-miR-615-5p | 1 | 1 | 1 | 1 | 1 |
| 2 | <u>auugcuucccagacggugaaga</u> | mmu-miR-686 | 1 | 1 | 1 | 1 | 1 |
| 3 | cgugggccugacguggagcugg | mmu-miR-770-3p | 1 | 1 | 1 | 1 | 1 |
| 4 | aaaucuaccugccucugccu | mmu-miR-1196 | 1 | 1 | 1 | 1 | 1 |
| 5 | aggaagcccuggaggggcuggag | mmu-miR-671-5p | 1 | 1 | 1 | 1 | 1 |
| 6 | gcagcuuucagauguggcuguaa | mmu-miR-693-3p | 1 | 1 | 1 | 1 | 1 |
| 7 | gucugc<u>ccc</u>gagugccugccucu | mmu-miR-346 | 1 | 1 | 1 | 1 | 1 |
| 8 | ggcgcgggcgcuggacgccucg | mmu-miR-1893 | 1 | 1 | 1 | 1 | 1 |
| 9 | uaaggcacgcggugaaugcc | mmu-miR-124 | 1 | 1 | 1 | 1 | 1 |
| 10 | gagcagcagaggaucuggaggu | mmu-miR-1907 | 1 | 1 | 1 | 1 | 1 |
| 11 | acguuggcucugguggugaug | mmu-miR-1306 | 1 | 1 | 1 | 1 | 1 |
| 12 | auaguuguguguggaugugugu | mmu-miR-669c | 1 | 1 | 1 | 1 | 1 |
| 13 | aggca<u>guguuguuag</u>cuggc | mmu-miR-449b | 1 | 1 | 1 | 1 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 14 | gcuucuccuggcucuccucccuc | mmu-miR-207 | 1 | 1 | 1 | 1 | 1 |
| 15 | gucucggugcaaggacuggagg | mmu-miR-678 | 1 | 1 | 1 | 1 | 1 |
| 16 | accaggaggcugaggucccu | mmu-miR-665 | 1 | 1 | 1 | 1 | 1 |
| 17 | aagggaggaucugggcaccugga | mmu-miR-1943 | 1 | 1 | 1 | 1 | 1 |
| 18 | cugguacaggccugggggauag | mmu-miR-150* | 1 | 1 | 1 | 1 | 1 |
| 19 | cagccucgcuggcaggcagcu | mmu-miR-681 | 1 | 1 | 1 | 1 | 1 |
| 20 | uuu<u>auug</u>agcaccuccuaucaa | mmu-miR-325 | 1 | 1 | 1 | 1 | 0 |
| 21 | aggucagaggucgauccugg | mmu-miR-540-3p | 1 | 1 | 1 | 1 | 0 |
| 22 | uuugaaccaucacucgacuccu | mmu-miR-434-3p | 1 | 1 | 1 | 1 | 0 |
| 23 | acguacaggccacugccuugc | mmu-let-7g* | 1 | 1 | 1 | 1 | -1 |
| 24 | aggca<u>gugcauug</u>cuagcugg | mmu-miR-449c | 1 | 1 | 1 | 0 | 1 |
| 25 | ugaagguccuacugugugccagg | mmu-miR-493 | 1 | 1 | 1 | 0 | 1 |
| 26 | aaacaaacauggugcacuucuu | mmu-miR-495 | 1 | 1 | 1 | 0 | 0 |
| 27 | ugaucu<u>agcc</u>aaagccgacugu | mmu-miR-344 | 1 | 1 | 1 | -1 | 1 |
| 28 | auguaugugugcaugugcaugu | mmu-miR-297a | 1 | 1 | 0 | 1 | 1 |
| 29 | ugugugcaugugcauguguguaa | mmu-miR-466j | 1 | 1 | 0 | 1 | 1 |
| 30 | acguguguggcaugugcaugu | mmu-miR-466f | 1 | 1 | 0 | 1 | 1 |
| 31 | ugagugugugugugagugugu | mmu-miR-574-5p | 1 | 1 | 0 | 1 | 1 |
| 32 | aguugugugug cauguauaugu | mmu-miR-6691 | 1 | 1 | 0 | 1 | 1 |
| 33 | ugugugcaugugcuugugugua | mmu-miR-466h | 1 | 1 | 0 | 1 | 1 |
| 34 | auaagugugugcauguauaugu | mmu-miR-467h | 1 | 1 | 0 | 1 | 1 |
| 35 | uauguguguguauguguguaa | mmu-miR-1187 | 1 | 1 | 0 | 1 | 1 |
| 36 | uacguguguggcaugugcaug | mmu-miR-466f-5p | 1 | 1 | 0 | 1 | 1 |
| 37 | ggugcucacauguccuccu | mmu-miR-764-5p | 1 | 1 | 0 | 1 | 1 |
| 38 | ccucugggcccuuccuc<u>cagu</u> | mmu-miR-326 | 1 | 1 | 0 | 1 | 1 |
| 39 | ccacugcccaggugcugcu | mmu-miR-324-3p | 1 | 1 | 0 | 1 | 1 |
| 40 | uucccuuugucauccuuugccu | mmu-miR-211 | 1 | 1 | 0 | 1 | 1 |
| 41 | uaagugcuuccauguuugagugu | mmu-miR-302d | 1 | 1 | 0 | 1 | 1 |
| 42 | gcacugagaugggagugguggua | mmu-miR-674 | 1 | 1 | 0 | 1 | 1 |
| 43 | caagggucaccucugacucugu | mmu-miR-540-5p | 1 | 1 | 0 | 1 | 1 |
| 44 | ugucuugcaggccgucaugca | mmu-miR-431 | 1 | 1 | 0 | 1 | 1 |
| 45 | ccugaacuaggggucuggagac | mmu-miR-345-3p | 1 | 1 | 0 | 1 | 1 |
| 46 | agucauacacggcucuccucuc | mmu-miR-485* | 1 | 1 | 0 | 1 | 0 |
| 47 | auuugugugggagugugugu | mmu-miR-669n | 1 | 1 | 0 | 0 | 1 |
| 48 | ggcagaggagggcuguucuuccc | mmu-miR-298 | 1 | 1 | 0 | 0 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 49 | ugugucacugggauaggcuuug | mmu-miR-1970 | 1 | 1 | 0 | 0 | 1 |
| 50 | gaugugugugugcauguacaua | mmu-miR-466c-5p | 1 | 1 | 0 | 0 | 1 |
| 51 | cgucaacacuugcugguuuucu | mmu-miR-505 | 1 | 1 | 0 | 0 | 1 |
| 52 | ucucccaacccuuguacc<u>agug</u> | mmu-miR-150 | 1 | 1 | 0 | 0 | 1 |
| 53 | uguguguguacauguacauguga | mmu-miR-466k | 1 | 1 | 0 | 0 | 1 |
| 54 | aagugcuuccauguuuc<u>agugg</u> | mmu-miR-302c | 1 | 1 | 0 | 0 | 1 |
| 55 | aggaggccauaguggcaacugu | mmu-miR-764-3p | 1 | 1 | 0 | 0 | 1 |
| 56 | ugcagcagcugaggcagggcu | mmu-miR-1906 | 1 | 1 | 0 | 0 | 1 |
| 57 | agaggu<u>gcagua</u>ggcaugacuu | mmu-miR-1902 | 1 | 1 | 0 | 0 | 1 |
| 58 | acggguuaggcucuugggagcu | mmu-miR-125b-3p | 1 | 1 | 0 | 0 | 1 |
| 59 | uaugacugaugugcgugugucug | mmu-miR-468 | 1 | 1 | 0 | 0 | 1 |
| 60 | uauacaagggcaagcucucugu | mmu-miR-381 | 1 | 1 | 0 | 0 | 1 |
| 61 | caaccuggaggacuccaugcug | mmu-miR-490 | 1 | 1 | 0 | 0 | 1 |
| 62 | aaagugccgccuaguuuuaagccc | mmu-miR-290-3p | 1 | 1 | 0 | 0 | 1 |
| 63 | aaugacaccacauauauggcagc | mmu-miR-489 | 1 | 1 | 0 | 0 | 1 |
| 64 | aaucgua<u>cagggu</u>cauccacuu | mmu-miR-487b | 1 | 1 | 0 | 0 | 1 |
| 65 | auguaugugugcauguacaugu | mmu-miR-297c | 1 | 1 | 0 | 0 | 1 |
| 66 | ugccucuuuc<u>auug</u>aucuuggu gucc | mmu-miR-469 | 1 | 1 | 0 | 0 | 1 |
| 67 | uaacacugucugguaaagaugg | mmu-miR-141 | 1 | 1 | 0 | 0 | 1 |
| 68 | agggagaugcugguacagaggcuu | mmu-miR-1941-5p | 1 | 1 | 0 | 0 | 1 |
| 69 | uauguaguaugguccacaucuu | mmu-miR-380-3p | 1 | 1 | 0 | 0 | 1 |
| 70 | aaagugcauccauuuuguuugu | mmu-miR-291b-3p | 1 | 1 | 0 | 0 | 1 |
| 71 | uacguaguauagugcuuuucac | mmu-miR-471 | 1 | 1 | 0 | 0 | 1 |
| 72 | uucagcuccuauaugaugccu | mmu-miR-337-3p | 1 | 1 | 0 | 0 | 0 |
| 73 | uuuuucauu<u>auug</u>cuccugacc | mmu-miR-335-3p | 1 | 1 | 0 | 0 | 0 |
| 74 | aacauagaggaaauuucacgu | mmu-miR-376c | 1 | 1 | 0 | 0 | 0 |
| 75 | ugaccgauuucuccugguguuc | mmu-miR-29c* | 1 | 1 | 0 | 0 | 0 |
| 76 | gcagcagggugaaacugacaca | mmu-miR-761 | 1 | 1 | 0 | 0 | 0 |
| 77 | <u>cagucaug</u>ccgcuugccuacg | mmu-miR-707 | 1 | 1 | 0 | 0 | 0 |
| 78 | uuauaaagcaaugagacugauu | mmu-miR-340-5p | 1 | 1 | 0 | 0 | 0 |
| 79 | aucacacaaggcaacuuuugu | mmu-miR-377 | 1 | 1 | 0 | 0 | 0 |
| 80 | ugcacugaaggca<u>cacagc</u> | mmu-miR-713 | 1 | 1 | 0 | -1 | 0 |
| 81 | aauauaacacaga<u>uggccugu</u> | mmu-miR-410 | 1 | 1 | -1 | 0 | 1 |
| 82 | auguaugugugcaugaacaugu | mmu-miR-297b-5p | 1 | 1 | -1 | 0 | 1 |
| 83 | ucacuccuccccucc<u>cgucuu</u> | mmu-miR-483* | 1 | 0 | 1 | 1 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 84 | gagcuuauucauaaaagugcag | mmu-miR-590-5p | 1 | 0 | 1 | 1 | 1 |
| 85 | ucgugucuuguguugcagccgg | mmu-miR-187 | 1 | 0 | 1 | 1 | 1 |
| 86 | gaguauguuuccacugccugg | mmu-miR-503* | 1 | 0 | 1 | 1 | 0 |
| 87 | aaugcaccugggcaaggguuca | mmu-miR-500 | 1 | 0 | 1 | 1 | 0 |
| 88 | auccaugaugggcuccucggugu | mmu-miR-433 | 1 | 0 | 1 | 1 | 0 |
| 89 | gaacggcguccaugcaggaguu | mmu-miR-337-5p | 1 | 0 | 1 | 1 | 0 |
| 90 | uccuguacugagcugccccgag | mmu-miR-486 | 1 | 0 | 1 | 1 | 0 |
| 91 | ugcgagucacccccggguguug | mmu-miR-712* | 1 | 0 | 1 | 1 | −1 |
| 92 | ucggucgaucggucggucggu | mmu-miR-341 | 1 | 0 | 1 | 1 | −1 |
| 93 | cucggggaucaucaugucacga | mmu-miR-542-5p | 1 | 0 | 1 | 0 | 0 |
| 94 | uuauugcuuaagaauacgcguag | mmu-miR-137 | 1 | 0 | 1 | 0 | 0 |
| 95 | ucuucgcggguacugucgggac | mmu-miR-1945 | 1 | 0 | 1 | 0 | 0 |
| 96 | cauaaaguagaaagcacuacu | mmu-miR-142-5p | 1 | 0 | 1 | 0 | 0 |
| 97 | caugguucugucaagcaccgcg | mmu-miR-218-2* | 1 | 0 | 1 | 0 | −1 |
| 98 | ccaagugcucagaugcuuguggu | mmu-miR-105 | 1 | 0 | 1 | −1 | 0 |
| 99 | augaggacugagaagguggagcaguu | mmu-miR-1940 | 1 | 0 | 1 | −1 | 0 |
| 100 | uaugugggacgguaaaccgcuu | mmu-miR-299 | 1 | 0 | 0 | 1 | 1 |
| 101 | aggucaagguucacagggggauc | mmu-miR-1898 | 1 | 0 | 0 | 1 | 0 |
| 102 | ugcagcuguuaaggaugguggacu | mmu-miR-1968 | 1 | 0 | 0 | 1 | 0 |
| 103 | auaagacgagcaaaaagcuugu | mmu-miR-208a | 1 | 0 | 0 | 1 | 0 |
| 104 | cagugguagagcauaugac | mmu-miR-1957 | 1 | 0 | 0 | 1 | 0 |
| 105 | uacuccagaauguggcaaucau | mmu-miR-509-5p | 1 | 0 | 0 | 1 | 0 |
| 106 | uaagugcgcgcauguauaugcg | mmu-miR-467d | 1 | 0 | 0 | 1 | 0 |
| 107 | gauguguguguaccauguacaua | mmu-miR-466e-5p | 1 | 0 | 0 | 0 | 1 |
| 108 | uagcagcgggaacaguacugcag | mmu-miR-503 | 1 | 0 | 0 | 0 | 1 |
| 109 | guaaaggcugggcugaga | mmu-miR-1971 | 1 | 0 | 0 | 0 | 1 |
| 110 | uucaccugguccacuagccg | mmu-miR-412 | 1 | 0 | 0 | 0 | 1 |
| 111 | uucccuuugucauccuaugccu | mmu-miR-204 | 1 | 0 | 0 | 0 | 1 |
| 112 | uccagcaucagugauuuuguug | mmu-miR-338-3p | 1 | 0 | 0 | 0 | 1 |
| 113 | uacucaguaaggcauuguucuu | mmu-miR-201 | 1 | 0 | 0 | 0 | 1 |
| 114 | auuccuagaaauuguucacaau | mmu-miR-384-3p | 1 | 0 | 0 | 0 | 1 |
| 115 | acaggugagguucuugggagcc | mmu-miR-125a-3p | 1 | 0 | 0 | 0 | 1 |
| 116 | uauacauacacgcacacauaaga | mmu-miR-466c-3p | 1 | 0 | 0 | 0 | 1 |
| 117 | uacugcaucaggaacugacugga | mmu-miR-217 | 1 | 0 | 0 | 0 | 1 |
| 118 | aucguagaggaaaauccacgu | mmu-miR-376a | 1 | 0 | 0 | 0 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 119 | aauugcacuuu<u>ag</u>caauggu<u>ga</u> | mmu-miR-367 | 1 | 0 | 0 | 0 | 0 |
| 120 | aggggugcuaucugug<u>au</u>u<u>ga</u>g | mmu-miR-342-5p | 1 | 0 | 0 | 0 | 0 |
| 121 | acuccauuuguuuugaugaugg | mmu-miR-136 | 1 | 0 | 0 | 0 | 0 |
| 122 | uaaggugcaucuagugcuguuag | mmu-miR-18b | 1 | 0 | 0 | 0 | 0 |
| 123 | gaaagccaccaugcuggguaaa | mmu-miR-742 | 1 | 0 | 0 | 0 | 0 |
| 124 | aauggcgccacuaggguu<u>gug</u> | mmu-miR-652 | 1 | 0 | 0 | 0 | 0 |
| 125 | uuugugaccugguccacua | mmu-miR-758 | 1 | 0 | 0 | 0 | 0 |
| 126 | ccuaguaggugcuc<u>ag</u>uaagugu | mmu-miR-325* | 1 | 0 | 0 | 0 | 0 |
| 127 | caacuagacugugagcuucuag | mmu-miR-708* | 1 | 0 | 0 | 0 | 0 |
| 128 | cuggagaggguuguuuacucc | mmu-miR-30c-1* | 1 | 0 | 0 | 0 | 0 |
| 129 | ua<u>cag</u>uauagaugauguacu | mmu-miR-144 | 1 | 0 | 0 | 0 | 0 |
| 130 | cggugggacuuguaguucgguc | mmu-miR-1938 | 1 | 0 | 0 | 0 | 0 |
| 131 | guaguggagacugguguggcua | mmu-miR-1951 | 1 | 0 | 0 | 0 | 0 |
| 132 | acucaaaauggaggcccuaucu | mmu-miR-294* | 1 | 0 | 0 | 0 | 0 |
| 133 | aggagagaguu<u>agcg</u>cauuagu | mmu-miR-882 | 1 | 0 | 0 | 0 | 0 |
| 134 | ccuguugaacaacugaacccaa | mmu-miR-582-3p | 1 | 0 | 0 | 0 | 0 |
| 135 | uauuuagaauggcacugauguga | mmu-miR-465a-5p | 1 | 0 | 0 | 0 | 0 |
| 136 | aaacauucgcggugcacuucuu | mmu-miR-543 | 1 | 0 | 0 | 0 | 0 |
| 137 | cugggauguggauguuuacguc | mmu-miR-30b* | 1 | 0 | 0 | 0 | 0 |
| 138 | uggca<u>gug</u>uauuguuagcuggu | mmu-miR-449a | 1 | 0 | 0 | 0 | 0 |
| 139 | ccuucuucuucuuccugagaca | mmu-miR-1903 | 1 | 0 | 0 | 0 | 0 |
| 140 | uaauacugucugguaaugccgu | mmu-miR-429 | 1 | 0 | 0 | 0 | 0 |
| 141 | aaagugcuacuacuuuugagucu | mmu-miR-295 | 1 | 0 | 0 | 0 | 0 |
| 142 | aaaccguuaccauuacugaguu | mmu-miR-451 | 1 | 0 | 0 | 0 | 0 |
| 143 | uggauuucucugugaaucacua | mmu-miR-876-5p | 1 | 0 | 0 | 0 | 0 |
| 144 | ucgagu<u>ccc</u>ggucgcgcgg | mmu-miR-1199 | 1 | 0 | 0 | 0 | −1 |
| 145 | gaccucuggauguuagggacuga | mmu-miR-1927 | 1 | 0 | 0 | 0 | −1 |
| 146 | uauguaacacgguccacuaacc | mmu-miR-411* | 1 | 0 | 0 | 0 | −1 |
| 147 | caucuuacugggca<u>gc</u>auugga | mmu-miR-200b* | 1 | 0 | 0 | 0 | −1 |
| 148 | gaaguuguucgguggugauucg | mmu-miR-382 | 1 | 0 | 0 | 0 | −1 |
| 149 | caaagugcucauagugcagguag | mmu-miR-20b | 1 | 0 | 0 | 0 | −1 |
| 150 | caucuuaccggacagugcugga | mmu-miR-200a* | 1 | 0 | 0 | 0 | −1 |
| 151 | gcucgacucauguuugaacca | mmu-miR-434-5p | 1 | 0 | 0 | 0 | −1 |
| 152 | cugcccugg<u>ccc</u>gagggaccga | mmu-miR-874 | 1 | 0 | 0 | 0 | −1 |
| 153 | gugugcggaaaugcuucugcua | mmu-miR-147 | 1 | 0 | 0 | −1 | 1 |
| 154 | ucuggaguagau<u>cag</u>ugggcag | mmu-miR-432 | 1 | 0 | 0 | −1 | 0 |

TABLE 1-continued

| | Detected miRNAs and their sorting in different cells | | | | | | |
|---|---|---|---|---|---|---|---|
| SEQ ID No | Sequence [Exosomal sorting motifs are in bold and cellular retention motifs are in underline | miRNAs | 3T3-L1 | C2C12 | SVEC | AML12 | RAT |
| 155 | gcuuuaacaugggguuaccugc | mmu-miR-302c* | 1 | 0 | 0 | -1 | 0 |
| 156 | caucccuugcaugguggaggg | mmu-miR-188-5p | 1 | 0 | 0 | -1 | 0 |
| 157 | caacaaauc<u>acagu</u>cugccaua | mmu-miR-7a* | 1 | 0 | 0 | -1 | -1 |
| 158 | acugc<u>agug</u>agggcacuuguag | mmu-miR-17* | 1 | 0 | 0 | -1 | -1 |
| 159 | cuauccuggaaugcagcaauga | mmu-miR-687 | 1 | 0 | -1 | 0 | 1 |
| 160 | acuuuaacaugggaaugcuuucu | mmu-miR-302b* | 1 | 0 | -1 | 0 | 0 |
| 161 | ugaggauccuggggagaagaugc | mmu-miR-1967 | 1 | 0 | -1 | 0 | 0 |
| 162 | uc<u>aguu</u>auc<u>acagu</u>gcugaugc | mmu-miR-101a* | 1 | 0 | -1 | -1 | 1 |
| 163 | aagggauucugauguuggucacacu | mmu-miR-541 | 1 | 0 | -1 | -1 | 0 |
| 164 | agguugccucauagugagcuugca | mmu-miR-453 | 1 | 0 | -1 | -1 | -1 |
| 165 | caauguuuc<u>cacagu</u>gcaucac | mmu-miR-33* | 1 | 0 | -1 | -1 | -1 |
| 166 | uggaauguaaggaagugugugg | mmu-miR-206 | 1 | -1 | 1 | 0 | 1 |
| 167 | aacauucaacgcugucggugagu | mmu-miR-181a | 1 | -1 | 1 | -1 | -1 |
| 168 | uuugguccccuucaaccagcua | mmu-miR-133b | 1 | -1 | 0 | 1 | 1 |
| 169 | uuugguccccuucaaccagcug | mmu-miR-133a | 1 | -1 | 0 | 1 | 1 |
| 170 | uagguaguuuccuguuguuggg | mmu-miR-196b | 1 | -1 | 0 | 1 | -1 |
| 171 | aacauucaaccugucggugagu | mmu-miR-181c | 1 | -1 | 0 | 0 | 0 |
| 172 | gugcauguaguugcauugca | mmu-miR-33 | 1 | -1 | 0 | 0 | 0 |
| 173 | uaggaaaguggaag<u>cagu</u>aagu | mmu-miR-1958 | 1 | -1 | 0 | 0 | 0 |
| 174 | aacauucauuguugucggugggu | mmu-miR-181d | 1 | -1 | 0 | -1 | 0 |
| 175 | uaguuuugcauaguugcacuac | mmu-miR-19a* | 1 | -1 | 0 | -1 | -1 |
| 176 | uggca<u>gu</u>gucuuagcugguugu | mmu-miR-34a | 1 | -1 | 0 | -1 | -1 |
| 177 | aggca<u>gu</u>guaauuagcugauugu | mmu-miR-34b-5p | 1 | -1 | -1 | -1 | -1 |
| 178 | ugguagacuauggaacguagg | mmu-miR-379 | 1 | -1 | -1 | -1 | -1 |
| 179 | cucccacaugcaggguuugca | mmu-miR-188-3p | 1 | -1 | -1 | -1 | -1 |
| 180 | agucccaggaugcacugcagcuuuu | mmu-miR-1955 | 1 | -1 | -1 | -1 | -1 |
| 181 | caaagugcuguucgugcagguag | mmu-miR-93 | 1 | -1 | -1 | -1 | -1 |
| 182 | u<u>acagu</u>uguucaaccaguuacu | mmu-miR-582-5p | 1 | -1 | -1 | -1 | -1 |
| 183 | auaagacgaacaaaagguuugu | mmu-miR-208b | 1 | -1 | -1 | -1 | -1 |
| 184 | aguccagggcugagucagcgga | mmu-miR-1956 | 0 | 1 | 1 | 1 | 1 |
| 185 | gccggcgggagccccagggag | mmu-miR-2137 | 0 | 1 | 1 | 1 | 1 |
| 186 | uggugugagguugggccagga | mmu-miR-1188 | 0 | 1 | 1 | 1 | 1 |
| 187 | aagacgggagaagagaagggag | mmu-miR-483 | 0 | 1 | 1 | 1 | 1 |
| 188 | aagggaacgggcuuggcggaau | mmu-miR-2138 | 0 | 1 | 1 | 1 | 1 |
| 189 | ccguccugagguuguugagcu | mmu-miR-676 | 0 | 1 | 1 | 1 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 190 | gaggguugggguggaggcucucc | mmu-miR-296-3p | 0 | 1 | 1 | 1 | 1 |
| 191 | gcaagggagagggugaagggag | mmu-miR-1894-3p | 0 | 1 | 1 | 1 | 1 |
| 192 | uccuucauuccaccggagucug | mmu-miR-205 | 0 | 1 | 1 | 1 | 0 |
| 193 | agcucggucugaggcccc<u>ucagu</u> | mmu-miR-423-3p | 0 | 1 | 1 | 1 | 0 |
| 194 | acugagaauggg<u>uagcaguc</u>a | mmu-miR-883b-5p | 0 | 1 | 1 | 0 | 1 |
| 195 | ucaauggcugaggugaggcac | mmu-miR-685 | 0 | 1 | 1 | 0 | 1 |
| 196 | cuagguauggucccagggaucc | mmu-miR-331-5p | 0 | 1 | 0 | 1 | 1 |
| 197 | agcuac<u>auug</u>ccagcuc | mmu-miR-1928 | 0 | 1 | 0 | 1 | 1 |
| 198 | ucuccacccuccuucug | mmu-miR-1952 | 0 | 1 | 0 | 1 | 1 |
| 199 | au<u>aca</u>gacacaugcacacaca | mmu-miR-466g | 0 | 1 | 0 | 1 | 1 |
| 200 | aguugugugug cauguucaugu | mmu-miR-669a | 0 | 1 | 0 | 1 | 1 |
| 201 | cacgcucaugcacacacccaca | mmu-miR-574-3p | 0 | 1 | 0 | 1 | 1 |
| 202 | uguuugcagaggaaacugagac | mmu-miR-452 | 0 | 1 | 0 | 1 | 1 |
| 203 | cucucccuaccaccugccucu | mmu-miR-1894-5p | 0 | 1 | 0 | 1 | 1 |
| 204 | acuugaggggcaugaggau | mmu-miR-327 | 0 | 1 | 0 | 1 | 1 |
| 205 | ucucac<u>acag</u>aaaucgca<u>cccg</u>u | mmu-miR-342-3p | 0 | 1 | 0 | 1 | 0 |
| 206 | aaacaugguuccgucaagcacc | mmu-miR-218-1* | 0 | 1 | 0 | 1 | 0 |
| 207 | cagauucgauucuaggggaaua | mmu-miR-10b* | 0 | 1 | 0 | 1 | 0 |
| 208 | gagugcuggaauuaaaggcaug | mmu-miR-1186 | 0 | 1 | 0 | 0 | 1 |
| 209 | uauguguguguacacauguacaua | mmu-miR-466a-5p | 0 | 1 | 0 | 0 | 1 |
| 210 | uggugcggaaagggccc<u>acagu</u> | mmu-miR-675-5p | 0 | 1 | 0 | 0 | 1 |
| 211 | uaagugcgugcauguauaugug | mmu-miR-467c | 0 | 1 | 0 | 0 | 1 |
| 212 | gaaugaguaacugcuagauccu | mmu-miR-1194 | 0 | 1 | 0 | 0 | 1 |
| 213 | aguuuugugugcaugugcaugu | mmu-miR-669b | 0 | 1 | 0 | 0 | 1 |
| 214 | cggcuacuucacaacaccaggg | mmu-miR-138* | 0 | 1 | 0 | 0 | 1 |
| 215 | gggcaucugcugacauggggg | mmu-miR-680 | 0 | 1 | 0 | 0 | 1 |
| 216 | ugaggggcagagagcgagacuuu | mmu-miR-423-5p | 0 | 1 | 0 | 0 | 1 |
| 217 | ccacc<u>acag</u>ugucagacacuu | mmu-miR-220 | 0 | 1 | 0 | 0 | 1 |
| 218 | uaguugugugug cauguuuaugu | mmu-miR-6690 | 0 | 1 | 0 | 0 | 1 |
| 219 | ccagcuggaagaaccagu<u>ggc</u> | mmu-miR-763 | 0 | 1 | 0 | 0 | 1 |
| 220 | agaucagaaggugacuguggcu | mmu-miR-383 | 0 | 1 | 0 | 0 | 1 |
| 221 | acucaaaugugggcacacuuc | mmu-miR-295* | 0 | 1 | 0 | 0 | 1 |
| 222 | ugagguugguguacuguguga | mmu-miR-672 | 0 | 1 | 0 | 0 | 1 |
| 223 | uaugcaagggcaagcucucuuc | mmu-miR-300 | 0 | 1 | 0 | 0 | 1 |
| 224 | ucagcugagguuccccucuguc | mmu-miR-1190 | 0 | 1 | 0 | 0 | 1 |
| 225 | ugcauauacacacaugcauac | mmu-miR-669i | 0 | 1 | 0 | 0 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 226 | uugaaccccugaccuccu | mmu-miR-2183 | 0 | 1 | 0 | 0 | 1 |
| 227 | ccugcuguaagcuguguccuc | mmu-miR-683 | 0 | 1 | 0 | 0 | 1 |
| 228 | cauacacacacacauacacac | mmu-miR-466f-3p | 0 | 1 | 0 | 0 | 1 |
| 229 | aucauagaggaacauccacuu | mmu-miR-376b | 0 | 1 | 0 | 0 | 1 |
| 230 | uggagugugacaaugguguuug | mmu-miR-122 | 0 | 1 | 0 | 0 | 1 |
| 231 | ggacugugaggugacucuuggu | mmu-miR-679 | 0 | 1 | 0 | 0 | 1 |
| 232 | aauugcacgguauccaucugua | mmu-miR-363 | 0 | 1 | 0 | 0 | 1 |
| 233 | cauucucguuuccuucccu | mmu-miR-698 | 0 | 1 | 0 | 0 | 1 |
| 234 | gcgacccauacuugguuucag | mmu-miR-551b | 0 | 1 | 0 | 0 | 1 |
| 235 | uggagacgcggcccuguuggag | mmu-miR-139-3p | 0 | 1 | 0 | 0 | 1 |
| 236 | uauguguuccuggcuggcuugg | mmu-miR-1198 | 0 | 1 | 0 | 0 | 1 |
| 237 | aacaauauccuggugcugagug | mmu-miR-338-5p | 0 | 1 | 0 | 0 | 1 |
| 238 | ggugggagguggggugggca | mmu-miR-705 | 0 | 1 | 0 | 0 | 1 |
| 239 | ccaagucuuggggagaguugag | mmu-miR-710 | 0 | 1 | 0 | 0 | 1 |
| 240 | acugcagugugagcacuucag | mmu-miR-20b* | 0 | 1 | 0 | 0 | 0 |
| 241 | aacacacccagcuaaccuuuuu | mmu-miR-329 | 0 | 1 | 0 | 0 | 0 |
| 242 | uugggaggguccugggagg | mmu-miR-1982* | 0 | 1 | 0 | 0 | 0 |
| 243 | cugaaaauguugccugaag | mmu-miR-694 | 0 | 1 | 0 | 0 | 0 |
| 244 | agaggcuggccgugaugaauuc | mmu-miR-485 | 0 | 1 | 0 | 0 | 0 |
| 245 | augccuuuugcucugcacuca | mmu-miR-511 | 0 | 1 | 0 | 0 | 0 |
| 246 | cagccacauccgaaaguuuuc | mmu-miR-693-5p | 0 | 1 | 0 | 0 | 0 |
| 247 | cccccgaggaggacgaggagga | mmu-miR-1895 | 0 | 1 | 0 | 0 | 0 |
| 248 | gcugaccccuaguccagugcuu | mmu-miR-345-5p | 0 | 1 | 0 | 0 | 0 |
| 249 | cugaagcucagagggcucugau | mmu-miR-127* | 0 | 1 | 0 | 0 | 0 |
| 250 | aaucacuaacuccacugccauc | mmu-miR-34b-3p | 0 | 1 | 0 | 0 | 0 |
| 251 | auucugcauuuuuagcaagcuc | mmu-miR-544 | 0 | 1 | −1 | 0 | 1 |
| 252 | gcaggaacuugugagucuccu | mmu-miR-873 | 0 | 1 | −1 | 0 | 1 |
| 253 | ccaguauugacugugcugcuga | mmu-miR-16* | 0 | 1 | −1 | −1 | 0 |
| 254 | cgaggugggaucccgaggccucuccmmu-miR-2143 | | 0 | 0 | 1 | 1 | 0 |
| 255 | uccgggggcugaguucugugcacc | mmu-miR-673-3p | 0 | 0 | 1 | 1 | 0 |
| 256 | cggcucugggucugugggga | mmu-miR-760 | 0 | 0 | 1 | 0 | 1 |
| 257 | gggacccggggagagauguaag | mmu-miR-711 | 0 | 0 | 1 | 0 | 1 |
| 258 | caucuuccagugcaguguugga | mmu-miR-141* | 0 | 0 | 1 | 0 | 0 |
| 259 | ugaguauuacauggccaaucuc | mmu-miR-496 | 0 | 0 | 1 | 0 | 0 |
| 260 | uaugcauauacacgcaugcaa | mmu-miR-669k | 0 | 0 | 1 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 261 | uaccaaguuuauucugugagaua | mmu-miR-464 | 0 | 0 | 1 | 0 | 0 |
| 262 | aaacaaacaaac<u>agac</u>caaauu | mmu-miR-1192 | 0 | 0 | 1 | 0 | 0 |
| 263 | ucggauccgucugagcuuggcu | mmu-miR-127 | 0 | 0 | 1 | 0 | −1 |
| 264 | cac<u>cagu</u>cccaccacgcgguag | mmu-miR-1905 | 0 | 0 | 1 | −1 | 0 |
| 265 | acucaaacuaugggggcacuuu | mmu-miR-290-5p | 0 | 0 | 0 | 1 | 1 |
| 266 | ugaguucgaggccagccugcuca | mmu-miR-1195 | 0 | 0 | 0 | 1 | 1 |
| 267 | uguccucuucucccuccuccca | mmu-miR-877* | 0 | 0 | 0 | 1 | 1 |
| 268 | uauacauacacacauacccaua | mmu-miR-297b-3p | 0 | 0 | 0 | 1 | 1 |
| 269 | ucucacccuauguucucc<u>cacag</u> | mmu-miR-1982.1 | 0 | 0 | 0 | 1 | 1 |
| 270 | caucu<u>uagcagu</u>aucucccau | mmu-miR-1941-3p | 0 | 0 | 0 | 1 | 1 |
| 271 | guucugcuccucuggagggagg | mmu-miR-1904 | 0 | 0 | 0 | 1 | 1 |
| 272 | aaugcacccgggcaaggauuug | mmu-miR-501-3p | 0 | 0 | 0 | 1 | 0 |
| 273 | cuggguguugacugagaugug | mmu-miR-2136 | 0 | 0 | 0 | 1 | 0 |
| 274 | ucaacucguucuguccggugag | mmu-miR-1897-3p | 0 | 0 | 0 | 1 | 0 |
| 275 | uaacugaccugcugugaacuggc | mmu-miR-1936 | 0 | 0 | 0 | 1 | 0 |
| 276 | cguugccacuaaccucaaccu | mmu-miR-744* | 0 | 0 | 0 | 1 | 0 |
| 277 | aauacauacacgcacacauaaga | mmu-miR-466b-3-3p | 0 | 0 | 0 | 1 | 0 |
| 278 | aaagugccgccagguuuugagugu | mmu-miR-292-3p | 0 | 0 | 0 | 1 | 0 |
| 279 | ugggaaaguucucaggcuucug | mmu-miR-1953 | 0 | 0 | 0 | 1 | 0 |
| 280 | cug<u>cagu</u>cacagugaagucug | mmu-miR-682 | 0 | 0 | 0 | 1 | −1 |
| 281 | uaa<u>cagu</u>cuccagucacggcca | mmu-miR-212 | 0 | 0 | 0 | 1 | −1 |
| 282 | uagguuauccguguugccuucg | mmu-miR-154 | 0 | 0 | 0 | 1 | −1 |
| 283 | auauacacacacacaccuaca | mmu-miR-467f | 0 | 0 | 0 | 0 | 1 |
| 284 | auacacacacacauacacacua | mmu-miR-466i | 0 | 0 | 0 | 0 | 1 |
| 285 | cuccuucacccgggcgguacc | mmu-miR-712 | 0 | 0 | 0 | 0 | 1 |
| 286 | auauacauacacacaccuauau | mmu-miR-467e* | 0 | 0 | 0 | 0 | 1 |
| 287 | agacccuggucugcacucuauc | mmu-miR-504 | 0 | 0 | 0 | 0 | 1 |
| 288 | gaucagggccuuucuaaguaga | mmu-miR-465b-3p | 0 | 0 | 0 | 0 | 1 |
| 289 | auauacauacacacaccuacac | mmu-miR-467d* | 0 | 0 | 0 | 0 | 1 |
| 290 | <u>auuggggg</u>augcuuugcauucau | mmu-miR-450a-3p | 0 | 0 | 0 | 0 | 1 |
| 291 | ucugguccccugcuucguccucu | mmu-miR-1934 | 0 | 0 | 0 | 0 | 1 |
| 292 | uauacauacacacacauauau | mmu-miR-467g | 0 | 0 | 0 | 0 | 1 |
| 293 | auaagugugagccauguauaugu | mmu-miR-467e | 0 | 0 | 0 | 0 | 1 |
| 294 | uaagugcuucccauguuuugguga | mmu-miR-302a | 0 | 0 | 0 | 0 | 1 |
| 295 | ucugcaucuaaggauaugguca | mmu-miR-1950 | 0 | 0 | 0 | 0 | 1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 296 | aacauccugguccuguggaga | mmu-miR-697 | 0 | 0 | 0 | 0 | 1 |
| 297 | ugugugugcguacauguacaug | mmu-miR-466d-5p | 0 | 0 | 0 | 0 | 1 |
| 298 | uaacugcaacaucucuca<u>guau</u> | mmu-miR-883b-3p | 0 | 0 | 0 | 0 | 1 |
| 299 | agacaugugcucugcuccuag | mmu-miR-704 | 0 | 0 | 0 | 0 | 1 |
| 300 | uauaaauacaugcacacauauu | mmu-miR-4661 | 0 | 0 | 0 | 0 | 1 |
| 301 | agaggcuugggggccgaaac | mmu-miR-2135 | 0 | 0 | 0 | 0 | 1 |
| 302 | uaaucucagcuggcaacuguga | mmu-miR-216a | 0 | 0 | 0 | 0 | 1 |
| 303 | uguucagacugguguccauca | mmu-miR-743b-5p | 0 | 0 | 0 | 0 | 1 |
| 304 | uaagugcuuccauguuuuaguag | mmu-miR-302b | 0 | 0 | 0 | 0 | 1 |
| 305 | ugacaccugccacccagcccaag | mmu-miR-667 | 0 | 0 | 0 | 0 | 0 |
| 306 | ucucugggccugugucuuaggc | mmu-miR-330 | 0 | 0 | 0 | 0 | 0 |
| 307 | uuuaggcagagcacucg<u>uacag</u> | mmu-miR-1948 | 0 | 0 | 0 | 0 | 0 |
| 308 | uaucuaguuggaugucaagaca | mmu-miR-878-5p | 0 | 0 | 0 | 0 | 0 |
| 309 | uauacauacacgcacacauaaga | mmu-miR-466a-3p | 0 | 0 | 0 | 0 | 0 |
| 310 | uccgagccugggucucccucuu | mmu-miR-615-3p | 0 | 0 | 0 | 0 | 0 |
| 311 | aagcccuuaccccaaaaagcau | mmu-miR-129-3p | 0 | 0 | 0 | 0 | 0 |
| 312 | agcugcgcugcuccugguaacugc | mmu-miR-2139 | 0 | 0 | 0 | 0 | 0 |
| 313 | uagugguuuacaaaguaauuca | mmu-miR-876-3p | 0 | 0 | 0 | 0 | 0 |
| 314 | uauaccuc<u>aguuuu</u>aucaggug | mmu-miR-875-5p | 0 | 0 | 0 | 0 | 0 |
| 315 | augguggcacggaguc | mmu-miR-546 | 0 | 0 | 0 | 0 | 0 |
| 316 | acugcccuaagugcuccuucug | mmu-miR-18a* | 0 | 0 | 0 | 0 | 0 |
| 317 | uauuuagaauggugcugaucug | mmu-miR-465b-5p | 0 | 0 | 0 | 0 | 0 |
| 318 | uggacggagaacugauaagggu | mmu-miR-184 | 0 | 0 | 0 | 0 | 0 |
| 319 | agcgauggccgaaucugcuucc | mmu-miR-1899 | 0 | 0 | 0 | 0 | 0 |
| 320 | uaggacacauggucuacuucu | mmu-miR-1197 | 0 | 0 | 0 | 0 | 0 |
| 321 | gaaagacaccaagcugaguaga | mmu-miR-743a | 0 | 0 | 0 | 0 | 0 |
| 322 | cgucuuacccag<u>cagu</u>guuugg | mmu-miR-200c* | 0 | 0 | 0 | 0 | 0 |
| 323 | ucaagagcaauaacgaaaaaugu | mmu-miR-335-5p | 0 | 0 | 0 | 0 | 0 |
| 324 | agucaugguguucggcuuaguuu | mmu-miR-1933-5p | 0 | 0 | 0 | 0 | 0 |
| 325 | ugggacgagaucaugaggccuuc | mmu-miR-1963 | 0 | 0 | 0 | 0 | 0 |
| 326 | uguaaacaauuccuaggcaaugu | mmu-miR-384-5p | 0 | 0 | 0 | 0 | 0 |
| 327 | aga<u>uu</u>ggcauaggugacugaa | mmu-miR-695 | 0 | 0 | 0 | 0 | 0 |
| 328 | uucuuggacuggcacuggugagu | mmu-miR-470 | 0 | 0 | 0 | 0 | 0 |
| 329 | acuuaaacgugguuguacuugc | mmu-miR-302a* | 0 | 0 | 0 | 0 | 0 |
| 330 | cacuagau<u>ugug</u>agcugccugga | mmu-miR-28* | 0 | 0 | 0 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 331 | uaagucacuaguggguuccguu | mmu-miR-224 | 0 | 0 | 0 | 0 | 0 |
| 332 | aagggagcuggcucaggagagagucmmu-miR-1966 | | 0 | 0 | 0 | 0 | 0 |
| 333 | accgaccguugacuguaccuug | mmu-miR-181a-2* | 0 | 0 | 0 | 0 | 0 |
| 334 | aagauggagacuuuaacaugggu | mmu-miR-1969 | 0 | 0 | 0 | 0 | 0 |
| 335 | aaagugcuuccacuuugugugc | mmu-miR-291a-3p | 0 | 0 | 0 | 0 | 0 |
| 336 | gguuguauuaucauugu<u>ccga</u>g | mmu-miR-374* | 0 | 0 | 0 | 0 | 0 |
| 337 | cagagagaua<u>acagu</u>cacaucu | mmu-miR-881* | 0 | 0 | 0 | 0 | 0 |
| 338 | uauggcuuuucauuccuauguga | mmu-miR-135b | 0 | 0 | 0 | 0 | 0 |
| 339 | ggcugcagcgugaucgccugcu | mmu-miR-666-3p | 0 | 0 | 0 | 0 | 0 |
| 340 | aucaucgucucaaaugagucuu | mmu-miR-136* | 0 | 0 | 0 | 0 | 0 |
| 341 | aggacgagc<u>uagc</u>ugagugcug | mmu-miR-1947 | 0 | 0 | 0 | 0 | 0 |
| 342 | ugcugagagaa<u>guag</u>caguuac | mmu-miR-883a-5p | 0 | 0 | 0 | 0 | 0 |
| 343 | acucuuucccuguugcacuacu | mmu-miR-130b* | 0 | 0 | 0 | 0 | 0 |
| 344 | caggucgucuugcagggcuucu | mmu-miR-431* | 0 | 0 | 0 | 0 | 0 |
| 345 | ca<u>acagcagu</u>cgaugggcuguc | mmu-miR-21* | 0 | 0 | 0 | 0 | 0 |
| 346 | uacauacuucuuuacauucca | mmu-miR-1-2-as | 0 | 0 | 0 | 0 | 0 |
| 347 | acugcagagugagacccuguu | mmu-miR-1954 | 0 | 0 | 0 | 0 | 0 |
| 348 | caggccauacugugcugccuca | mmu-miR-15a* | 0 | 0 | 0 | 0 | 0 |
| 349 | uauggcuuuuuauuccuauguga | mmu-miR-135a | 0 | 0 | 0 | 0 | 0 |
| 350 | gucuugggaaacggggugc | mmu-miR-2134 | 0 | 0 | 0 | 0 | 0 |
| 351 | gaucagggccuuucuaaguaga | mmu-miR-465a-3p | 0 | 0 | 0 | 0 | 0 |
| 352 | uacucacaugguugcuaauca | mmu-miR-742* | 0 | 0 | 0 | 0 | 0 |
| 353 | uccgguucucagggcuccacc | mmu-miR-671-3p | 0 | 0 | 0 | 0 | 0 |
| 354 | gcccuaaggugaauuuuuuggg | mmu-miR-186* | 0 | 0 | 0 | 0 | 0 |
| 355 | agguua<u>ccc</u>gagcaacuuugcau | mmu-miR-409-5p | 0 | 0 | 0 | 0 | 0 |
| 356 | gcaugacaccacacuggguaga | mmu-miR-878-3p | 0 | 0 | 0 | 0 | 0 |
| 357 | gaauguugcucggugaaccccu | mmu-miR-409-3p | 0 | 0 | 0 | 0 | 0 |
| 358 | auuccuggaaauacuguucuug | mmu-miR-145* | 0 | 0 | 0 | 0 | 0 |
| 359 | uugcauauguaggaugucccau | mmu-miR-448 | 0 | 0 | 0 | 0 | 0 |
| 360 | uacuccauccucucugaguaga | mmu-miR-880 | 0 | 0 | 0 | 0 | 0 |
| 361 | ccguucuccauuacuuggcuc | mmu-miR-26b* | 0 | 0 | 0 | 0 | 0 |
| 362 | caagcucgucucuguggguccg | mmu-miR-99b* | 0 | 0 | 0 | 0 | 0 |
| 363 | ccagugcguuuagaagagggcu | mmu-miR-1960 | 0 | 0 | 0 | 0 | 0 |
| 364 | ugccugucuacacugcugugc | mmu-miR-214* | 0 | 0 | 0 | 0 | 0 |
| 365 | ucggcaacaagaaacugccuga | mmu-miR-196a* | 0 | 0 | 0 | 0 | 0 |
| 366 | cuauacaaucu<u>auug</u>ccuuccc | mmu-let-7f* | 0 | 0 | 0 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 367 | gaucagggccuuucuaaguaga | mmu-miR-465c-3p | 0 | 0 | 0 | 0 | 0 |
| 368 | auauacauacacacaccuacac | mmu-miR-467a* | 0 | 0 | 0 | 0 | 0 |
| 369 | cucucugauggugggugaggag | mmu-miR-1896 | 0 | 0 | 0 | 0 | 0 |
| 370 | uca<u>gu</u>aacaaagauucauccuu | mmu-miR-802 | 0 | 0 | 0 | 0 | 0 |
| 371 | uacggugagccugucauuauuc | mmu-miR-433* | 0 | 0 | 0 | 0 | 0 |
| 372 | uaccuaauuuguuguccaucau | mmu-miR-463* | 0 | 0 | 0 | 0 | 0 |
| 373 | aaagugcuucccuuuugugugu | mmu-miR-294 | 0 | 0 | 0 | 0 | 0 |
| 374 | cguuuc<u>acag</u>cggaccuugau | mmu-miR-124* | 0 | 0 | 0 | 0 | 0 |
| 375 | uguaguguuuccuacuuuaugga | mmu-miR-142-3p | 0 | 0 | 0 | 0 | 0 |
| 376 | cccagaua<u>au</u>agcacucucaa | mmu-miR-488* | 0 | 0 | 0 | 0 | 0 |
| 377 | guggauauuccuucuaugguua | mmu-miR-376b* | 0 | 0 | 0 | 0 | 0 |
| 378 | ggggauguagcucaguggag | mmu-miR-1959 | 0 | 0 | 0 | 0 | 0 |
| 379 | aaaucucugcaggcaaauguga | mmu-miR-216b | 0 | 0 | 0 | 0 | 0 |
| 380 | cuauacaaccuacugccuuccc | mmu-let-7b* | 0 | 0 | 0 | 0 | 0 |
| 381 | uauacauacacacauacccaua | mmu-miR-297a* | 0 | 0 | 0 | 0 | 0 |
| 382 | aucccugaguguauguggugaa | mmu-miR-670 | 0 | 0 | 0 | 0 | 0 |
| 383 | uggaagacuugugauuuuguugu | mmu-miR-7b | 0 | 0 | 0 | 0 | 0 |
| 384 | uuguguc<u>ag</u>uuuaucaaac | mmu-miR-599 | 0 | 0 | 0 | 0 | 0 |
| 385 | caaauucguaucuaggggaaua | mmu-miR-10a* | 0 | 0 | 0 | 0 | 0 |
| 386 | auauacauccacacaaacauau | mmu-miR-669m | 0 | 0 | 0 | 0 | 0 |
| 387 | uugaagagagguuauccuuugu | mmu-miR-300* | 0 | 0 | 0 | 0 | 0 |
| 388 | agcugguguugugaaucaggccg | mmu-miR-138 | 0 | 0 | 0 | 0 | 0 |
| 389 | aaaagcuggguugagagggcga | mmu-miR-320 | 0 | 0 | 0 | 0 | 0 |
| 390 | ugcggggcuagggcuaacagca | mmu-miR-744 | 0 | 0 | 0 | 0 | 0 |
| 391 | cucag<u>ac</u>agagauaccuucucu | mmu-miR-717 | 0 | 0 | 0 | 0 | 0 |
| 392 | uauacauacacacauacccaua | mmu-miR-297c* | 0 | 0 | 0 | 0 | 0 |
| 393 | ugu<u>ca</u>guuugucaaauaccccca | mmu-miR-223 | 0 | 0 | 0 | 0 | 0 |
| 394 | cguuaugcccuaaccgcuc<u>agu</u> | mmu-miR-675-3p | 0 | 0 | 0 | 0 | 0 |
| 395 | uggaagacuagugauuuuguugu | mmu-miR-7a | 0 | 0 | 0 | 0 | 0 |
| 396 | gcuuauggcuucaagcuuucgg | mmu-miR-879* | 0 | 0 | 0 | 0 | 0 |
| 397 | gcccuagggacucaguucuggu | mmu-miR-146b* | 0 | 0 | 0 | 0 | 0 |
| 398 | ucccugaggagcccuuugagccug | mmu-miR-351 | 0 | 0 | 0 | 0 | 0 |
| 399 | <u>ua</u>uugcacauuacuaaguugca | mmu-miR-32 | 0 | 0 | 0 | 0 | 0 |
| 400 | agugccgcagaguuuguagugu | mmu-miR-293 | 0 | 0 | 0 | 0 | 0 |
| 401 | aauccuuugucccugggugaaa | mmu-miR-501-5p | 0 | 0 | 0 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 402 | uaacugc<u>aacagc</u>cu<u>cuc</u>aguau | mmu-miR-883a-3p | 0 | 0 | 0 | 0 | 0 |
| 403 | aucucggcu<u>acaga</u>aaaauguu | mmu-miR-719 | 0 | 0 | 0 | 0 | 0 |
| 404 | caaagaauucuccuuuugggcu | mmu-miR-186 | 0 | 0 | 0 | 0 | 0 |
| 405 | uucaccaccuucuccacccagc | mmu-miR-197 | 0 | 0 | 0 | 0 | 0 |
| 406 | ccc<u>agu</u>guucagacuaccuguuc | mmu-miR-199a-5p | 0 | 0 | 0 | 0 | 0 |
| 407 | uaacacugucugguaacgaugu | mmu-miR-200a | 0 | 0 | 0 | 0 | 0 |
| 408 | uaauacugccggguaaugaugga | mmu-miR-200c | 0 | 0 | 0 | 0 | 0 |
| 409 | agagguauagcgcaugggaaga | mmu-miR-202-3p | 0 | 0 | 0 | 0 | 0 |
| 410 | uuccuaugcauauacuucuuu | mmu-miR-202-5p | 0 | 0 | 0 | 0 | 0 |
| 411 | gugaaauguuuaggaccacuag | mmu-miR-203 | 0 | 0 | 0 | 0 | 0 |
| 412 | agggcccccccucaauccugu | mmu-miR-296-5p | 0 | 0 | 0 | 0 | 0 |
| 413 | ugagcgccucggcg<u>acag</u>agccg | mmu-miR-339-3p | 0 | 0 | 0 | 0 | 0 |
| 414 | ugauagacaccauauaagguag | mmu-miR-463 | 0 | 0 | 0 | 0 | 0 |
| 415 | ucgcaggcgacuacuuauuc | mmu-miR-688 | 0 | 0 | 0 | 0 | 0 |
| 416 | gcagagugcaaacaauuuugac | mmu-miR-759 | 0 | 0 | 0 | 0 | 0 |
| 417 | ggggcuggggccgggac<u>ag</u>agc | mmu-miR-762 | 0 | 0 | 0 | 0 | 0 |
| 418 | gaucaaaguggaggcccucucc | mmu-miR-291b-5p | 0 | 0 | 0 | 0 | −1 |
| 419 | ugguuuaccgucccacauacau | mmu-miR-299* | 0 | 0 | 0 | 0 | −1 |
| 420 | ccucccacacccaaggcuugca | mmu-miR-532-3p | 0 | 0 | 0 | 0 | −1 |
| 421 | gcugcacuuggauuucguuccc | mmu-miR-191* | 0 | 0 | 0 | 0 | −1 |
| 422 | uaa<u>cagu</u>cuacagccauggucg | mmu-miR-132 | 0 | 0 | 0 | 0 | −1 |
| 423 | ugaacu<u>auug</u>caguagccuccu | mmu-miR-872* | 0 | 0 | 0 | 0 | −1 |
| 424 | uaauacugccugguaaugauga | mmu-miR-200b | 0 | 0 | 0 | 0 | −1 |
| 425 | uaggucac<u>ccg</u>uuuuacuauc | mmu-miR-1193 | 0 | 0 | 0 | 0 | −1 |
| 426 | cgacgagggccggucggucgc | mmu-miR-714 | 0 | 0 | 0 | 0 | −1 |
| 427 | auccugaagagaggcagaaaa | mmu-miR-691 | 0 | 0 | 0 | 0 | −1 |
| 428 | agaucgaccguguuauauucgc | mmu-miR-369-5p | 0 | 0 | 0 | 0 | −1 |
| 429 | aucgggaaugucguguccgcc | mmu-miR-425* | 0 | 0 | 0 | 0 | −1 |
| 430 | uaugucugcugaccaucaccuu | mmu-miR-654-3p | 0 | 0 | 0 | 0 | −1 |
| 431 | cacgcgggaaccgaguccacc | mmu-miR-700 | 0 | 0 | 0 | 0 | −1 |
| 432 | ccgacuucugggcuccggcuuu | mmu-miR-1964 | 0 | 0 | 0 | 0 | −1 |
| 433 | gguagauucuccuucuaugagu | mmu-miR-376a* | 0 | 0 | 0 | 0 | −1 |
| 434 | uacgucaucgucgucaucguua | mmu-miR-598 | 0 | 0 | 0 | 0 | −1 |
| 435 | aauaauacaugguugaucuuu | mmu-miR-369-3p | 0 | 0 | 0 | 0 | −1 |
| 436 | ugguaagcugcagaacaugugu | mmu-miR-654-5p | 0 | 0 | 0 | −1 | 1 |
| 437 | cuuuuugcggucugggcuugc | mmu-miR-129-5p | 0 | 0 | 0 | −1 | 1 |

TABLE 1-continued

| | Detected miRNAs and their sorting in different cells | | | | | | |
|---|---|---|---|---|---|---|---|
| SEQ ID No | Sequence [Exosomal sorting motifs are in bold and cellular retention motifs are in underline | miRNAs | 3T3-L1 | C2C12 | SVEC | AML12 | RAT |
| 438 | cugcgcaagcuacugccuugcu | mmu-let-7i* | 0 | 0 | 0 | −1 | 0 |
| 439 | acaagucagguucuugggaccu | mmu-miR-125b* | 0 | 0 | 0 | −1 | 0 |
| 440 | uaugcauauacacacaugcaca | mmu-miR-669h-3p | 0 | 0 | 0 | −1 | 0 |
| 441 | uggaauguaaagaaguauguau | mmu-miR-1 | 0 | 0 | 0 | −1 | 0 |
| 442 | ucagaugucuucaucugguug | mmu-miR-1942 | 0 | 0 | 0 | −1 | 0 |
| 443 | augcauggguguauaguugagugc | mmu-miR-669h-5p | 0 | 0 | 0 | −1 | 0 |
| 444 | cagucuuacuau<u>guag</u>cccua | mmu-miR-1191 | 0 | 0 | 0 | −1 | 0 |
| 445 | augaccuaugauuuga<u>cagac</u> | mmu-miR-215 | 0 | 0 | 0 | −1 | 0 |
| 446 | uuuug<u>cag</u>uauguuccugaaua | mmu-miR-450b-5p | 0 | 0 | 0 | −1 | 0 |
| 447 | acucuacaaccuuaggacuugc | mmu-miR-676* | 0 | 0 | 0 | −1 | 0 |
| 448 | ccugaaaauacugaggcuaug | mmu-miR-875-3p | 0 | 0 | 0 | −1 | 0 |
| 449 | gcaguccacgggcauauacac | mmu-miR-455 | 0 | 0 | 0 | −1 | −1 |
| 450 | cugugc<u>gugug</u>acagcggcuga | mmu-miR-210 | 0 | 0 | 0 | −1 | −1 |
| 451 | aaucauacacgguugaccuauu | mmu-miR-154* | 0 | 0 | 0 | −1 | −1 |
| 452 | augguugaccauagaacaugcg | mmu-miR-380-5p | 0 | 0 | 0 | −1 | −1 |
| 453 | ugucuugugugugcauguucau | mmu-miR-669e | 0 | 0 | 0 | −1 | −1 |
| 454 | acugcugagcua<u>gcacuuccg</u> | mmu-miR-93* | 0 | 0 | 0 | −1 | −1 |
| 455 | cuugguacaucuuugagugag | mmu-miR-547 | 0 | 0 | 0 | −1 | −1 |
| 456 | <u>auugug</u>ucaauaugcgaugaugu | mmu-miR-592 | 0 | 0 | 0 | −1 | −1 |
| 457 | <u>cag</u>ugcaauuaaaagggggaa | mmu-miR-721 | 0 | 0 | 0 | −1 | −1 |
| 458 | cucaccuggagcauguuuucu | mmu-miR-1983 | 0 | 0 | −1 | 1 | 0 |
| 459 | uauacauacacgcacacauag | mmu-miR-466d-3p | 0 | 0 | −1 | 1 | 0 |
| 460 | gcgugugcuugcuguggg | mmu-miR-696 | 0 | 0 | −1 | 0 | 1 |
| 461 | agccgggcagug<u>guggca</u>cacacuummu-miR-1946a uu | | 0 | 0 | −1 | 0 | 1 |
| 462 | uggagagaaaggcaguuccuga | mmu-miR-185 | 0 | 0 | −1 | 0 | 1 |
| 463 | auauacauacacacaccaacac | mmu-miR-467b* | 0 | 0 | −1 | 0 | 1 |
| 464 | aguggggaacccuuccaugagg | mmu-miR-491 | 0 | 0 | −1 | 0 | 1 |
| 465 | aggcagaggcuggcggaucucu | mmu-miR-1935 | 0 | 0 | −1 | 0 | 1 |
| 466 | agagcuu<u>ag</u>cugauuggugaac | mmu-miR-27b* | 0 | 0 | −1 | 0 | 1 |
| 467 | gccgggcagug<u>guggca</u>caug cuuuu | mmu-miR-1946b | 0 | 0 | −1 | 0 | 1 |
| 468 | <u>au</u>ugggaacauuuugcaugcau | mmu-miR-450b-3p | 0 | 0 | −1 | 0 | 0 |
| 469 | acucaaacugugugacauuuug | mmu-miR-293* | 0 | 0 | −1 | 0 | 0 |
| 470 | agggcuu<u>ag</u>cugcuuugugagca | mmu-miR-27a* | 0 | 0 | −1 | 0 | 0 |
| 471 | gaaagacaucaugcugaauaga | mmu-miR-743b-3p | 0 | 0 | −1 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 472 | agugguucuugacaguucaaca | mmu-miR-203* | 0 | 0 | -1 | 0 | 0 |
| 473 | aaaguucugagacacuccgacu | mmu-miR-148a* | 0 | 0 | -1 | 0 | 0 |
| 474 | uugaaaggcuguuucuugguc | mmu-miR-488 | 0 | 0 | -1 | -1 | 1 |
| 475 | ugcauauacucacaugcaaaca | mmu-miR-669j | 0 | 0 | -1 | -1 | 0 |
| 476 | ucauucacggacaacacuuuuu | mmu-miR-382* | 0 | 0 | -1 | -1 | 0 |
| 477 | acuugugugugcauguauaugu | mmu-miR-669d | 0 | 0 | -1 | -1 | 0 |
| 478 | accuccauaguaccugcagcgu | mmu-miR-1930 | 0 | 0 | -1 | -1 | 0 |
| 479 | uccgucucaguuacuuuaugc | mmu-miR-340-3p | 0 | 0 | -1 | -1 | -1 |
| 480 | uuagccgcgaaauagaugga | mmu-miR-701 | 0 | 0 | -1 | -1 | -1 |
| 481 | cauuauuacuuuugguacgcg | mmu-miR-126-5p | 0 | -1 | 1 | 1 | -1 |
| 482 | aggcaagaugcuggcauagcug | mmu-miR-31 | 0 | -1 | 1 | 0 | 0 |
| 483 | ugagaugaagcacuguagcuc | mmu-miR-143 | 0 | -1 | 0 | 1 | 0 |
| 484 | uagguaguuucauguuguuggg | mmu-miR-196a | 0 | -1 | 0 | 1 | -1 |
| 485 | gcugguuucauauggugguuua | mmu-miR-29b* | 0 | -1 | 0 | 1 | -1 |
| 486 | ucuggcuccgugucuucacuccc | mmu-miR-149 | 0 | -1 | 0 | 0 | 0 |
| 487 | ucacagugaaccggucucuuu | mmu-miR-128 | 0 | -1 | 0 | 0 | 0 |
| 488 | agagaaacccugucucaaaaaa | mmu-miR-706 | 0 | -1 | 0 | 0 | 0 |
| 489 | uugcauagucacaaaagugauc | mmu-miR-153 | 0 | -1 | 0 | 0 | 0 |
| 490 | ugggucuuugcgggcaagauga | mmu-miR-193* | 0 | -1 | 0 | 0 | 0 |
| 491 | aaacaugaagcgcugcaacac | mmu-miR-322* | 0 | -1 | 0 | 0 | -1 |
| 492 | ucuuugguuaucuagcuguauga | mmu-miR-9 | 0 | -1 | 0 | 0 | -1 |
| 493 | ugauauguuugauauuggguu | mmu-miR-190b | 0 | -1 | 0 | 0 | -1 |
| 494 | uuuguucguucggcucgcguga | mmu-miR-375 | 0 | -1 | 0 | 0 | -1 |
| 495 | aggugggauugguggcauuac | mmu-miR-92a* | 0 | -1 | 0 | 0 | -1 |
| 496 | acugcauuacgagcacuuaaag | mmu-miR-20a* | 0 | -1 | 0 | -1 | 0 |
| 497 | gcugguaaaauggaaccaaau | mmu-miR-133a* | 0 | -1 | 0 | -1 | 0 |
| 498 | aacacaccuguucaaggauuca | mmu-miR-362-3p | 0 | -1 | 0 | -1 | 0 |
| 499 | uaaagugcuuauagugcagguag | mmu-miR-20a | 0 | -1 | 0 | -1 | -1 |
| 500 | caaagugcuaacagugcagguag | mmu-miR-106a | 0 | -1 | 0 | -1 | -1 |
| 501 | caugccuggaguguaggaccgu | mmu-miR-532-5p | 0 | -1 | 0 | -1 | -1 |
| 502 | cgaaucauuauuugcugcucua | mmu-miR-15b* | 0 | -1 | 0 | -1 | -1 |
| 503 | caacggaaucccaaaagcagcug | mmu-miR-191 | 0 | -1 | 0 | -1 | -1 |
| 504 | aacauucauugcugucgguggu | mmu-miR-181b | 0 | -1 | 0 | -1 | -1 |
| 505 | ucguaccgugaguaauaaugcg | mmu-miR-126-3p | 0 | -1 | 0 | -1 | -1 |
| 506 | uaaggugcaucuagugcagauag | mmu-miR-18a | 0 | -1 | -1 | 0 | -1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 507 | aguucuucaguggcaagcuuua | mmu-miR-22* | 0 | -1 | -1 | 0 | -1 |
| 508 | <u>cagugcaa</u>uagu<u>auu</u>gucaaagc | mmu-miR-301a | 0 | -1 | -1 | -1 | -1 |
| 509 | <u>cagugcaa</u>ug<u>guauu</u>gucaaagc | mmu-miR-301b | 0 | -1 | -1 | -1 | -1 |
| 510 | caaagugcuu<u>acagu</u>gcagguag | mmu-miR-17 | 0 | -1 | -1 | -1 | -1 |
| 511 | accaucgaccguug<u>auu</u>guacc | mmu-miR-181a-1* | 0 | -1 | -1 | -1 | -1 |
| 512 | aauccuuggaaccuaggugugaau | mmu-miR-362-5p | 0 | -1 | -1 | -1 | -1 |
| 513 | uuaagacuugc<u>agu</u>gauguuu | mmu-miR-499 | 0 | -1 | -1 | -1 | -1 |
| 514 | acug<u>auu</u>ucuuuuggug<u>uu</u>cag | mmu-miR-29a* | 0 | -1 | -1 | -1 | -1 |
| 515 | aacuggcccacaaagu<u>ccc</u>gcu | mmu-miR-193b | -1 | 1 | 1 | 1 | 0 |
| 516 | accgggugcuguaggcuuu | mmu-miR-2142 | -1 | 1 | 1 | 1 | 0 |
| 517 | guagaggagauggcgcaggg | mmu-miR-877 | -1 | 1 | 0 | 1 | 0 |
| 518 | cgcaucccuagggcauu<u>ggu</u>gu | mmu-miR-324-5p | -1 | 1 | 0 | 1 | -1 |
| 519 | aucucuuugagcgccucacuc | mmu-miR-692 | -1 | 1 | 0 | 1 | -1 |
| 520 | acagcaggcacagacaggca<u>gu</u> | mmu-miR-214 | -1 | 1 | 0 | 0 | 1 |
| 521 | aacuggccuacaaagu<u>ccc</u>agu | mmu-miR-193 | -1 | 1 | 0 | 0 | 0 |
| 522 | caucaaaguggaggcccucucu | mmu-miR-291a-5p | -1 | 1 | 0 | 0 | 0 |
| 523 | agcagggucgggccugguu | mmu-miR-2145 | -1 | 1 | 0 | 0 | -1 |
| 524 | agcaccacgugucugggccacg | mmu-miR-770-5p | -1 | 1 | 0 | -1 | 0 |
| 525 | cauauacauacacacacguau | mmu-miR-669f | -1 | 1 | 0 | -1 | -1 |
| 526 | gugaggacuggggagguggag | mmu-miR-1224 | -1 | 0 | 1 | 1 | 1 |
| 527 | auuugggacgggagggaggau | mmu-miR-1892 | -1 | 0 | 1 | 1 | 0 |
| 528 | aagccgggccguaguggcgca | mmu-miR-1965 | -1 | 0 | 1 | 1 | 0 |
| 529 | ggcggguguugacgcgaug | mmu-miR-2132 | -1 | 0 | 1 | 1 | 0 |
| 530 | aaggagcuuacaaucuagcuggg | mmu-miR-708 | -1 | 0 | 1 | 1 | -1 |
| 531 | <u>cagugcaa</u>ugaugaaagggcau | mmu-miR-130b | -1 | 0 | 1 | 1 | -1 |
| 532 | uaguagaccgau<u>uagc</u>guacg | mmu-miR-411 | -1 | 0 | 1 | 1 | -1 |
| 533 | aggaggugucagaaaaguu | mmu-miR-2141 | -1 | 0 | 1 | 0 | 1 |
| 534 | cuuccgc<u>ccg</u>gccgggugucg | mmu-miR-718 | -1 | 0 | 1 | 0 | 0 |
| 535 | cuggcccucucugcccuuccgu | mmu-miR-328 | -1 | 0 | 1 | 0 | -1 |
| 536 | ugugaguuguuccucaccugga | mmu-miR-804 | -1 | 0 | 1 | 0 | -1 |
| 537 | ggaggcagaggcaggagga | mmu-miR-709 | -1 | 0 | 0 | 1 | 0 |
| 538 | augcaagggcuggugcgauggc | mmu-miR-1931 | -1 | 0 | 0 | 1 | 0 |
| 539 | guaaaggcuggcuuagacguggc | mmu-miR-1981 | -1 | 0 | 0 | 1 | 0 |
| 540 | gagugccuagugggccacuuuuggu | mmu-miR-2144 | -1 | 0 | 0 | 1 | 0 |
| 541 | uauagggauuggagccguggcg | mmu-miR-135a* | -1 | 0 | 0 | 1 | 0 |
| 542 | uauacauacacgcacacauaaga | mmu-miR-466b-3p | -1 | 0 | 0 | 1 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 543 | aggugguccguggcgcguucgc | mmu-miR-323-5p | -1 | 0 | 0 | 1 | -1 |
| 544 | ugagguaguagguuguaugguu | mmu-let-7c | -1 | 0 | 0 | 0 | 0 |
| 545 | ugagguaguagguugugugguu | mmu-let-7b | -1 | 0 | 0 | 0 | 0 |
| 546 | acuggacuuggagucagaagg | mmu-miR-378 | -1 | 0 | 0 | 0 | 0 |
| 547 | aggugcagaucuuggugu | mmu-miR-2140 | -1 | 0 | 0 | 0 | 0 |
| 548 | guggagaaggguuccaugug | mmu-miR-2146 | -1 | 0 | 0 | 0 | 0 |
| 549 | ucuac<u>agug</u>cacgugucuccag | mmu-miR-139-5p | -1 | 0 | 0 | 0 | 0 |
| 550 | uauggcacugguagaauucacu | mmu-miR-183 | -1 | 0 | 0 | 0 | 0 |
| 551 | cuauacaaucuacugucuuucc | mmu-let-7c-2* | -1 | 0 | 0 | 0 | 0 |
| 552 | ugaaacauacacgggaaaccuc | mmu-miR-494 | -1 | 0 | 0 | 0 | 0 |
| 553 | uaaugccccuaaaaauccuuau | mmu-miR-365 | -1 | 0 | 0 | 0 | 0 |
| 554 | uauuuagaauggcgcugaucug | mmu-miR-465c-5p | -1 | 0 | 0 | 0 | 0 |
| 555 | guaagugccugcauguauaug | mmu-miR-467b | -1 | 0 | 0 | 0 | 0 |
| 556 | cuc<u>acag</u>cucugguccuuggag | mmu-miR-673-5p | -1 | 0 | 0 | 0 | 0 |
| 557 | ggagaaauuauccuuggugugu | mmu-miR-539 | -1 | 0 | 0 | 0 | 0 |
| 558 | uauugcacuugu<u>cccg</u>gccug | mmu-miR-92a | -1 | 0 | 0 | 0 | -1 |
| 559 | cuagacugaggcuccuugagg | mmu-miR-151-3p | -1 | 0 | 0 | 0 | -1 |
| 560 | ugucacucggcucggcccacuacc | mmu-miR-668 | -1 | 0 | 0 | 0 | -1 |
| 561 | ugugacugguugaccagagggg | mmu-miR-134 | -1 | 0 | 0 | 0 | -1 |
| 562 | uauugcacucgu<u>cccg</u>gccucc | mmu-miR-92b | -1 | 0 | 0 | 0 | -1 |
| 563 | aaucacuaaccac<u>acag</u>ccagg | mmu-miR-34c* | -1 | 0 | 0 | 0 | -1 |
| 564 | uauucagauuagugccagucaug | mmu-miR-871 | -1 | 0 | 0 | -1 | 1 |
| 565 | gucccgcggggcccgaagcguu | mmu-miR-2133 | -1 | 0 | 0 | -1 | 0 |
| 566 | ugcaccauguugucugagca | mmu-miR-767 | -1 | 0 | 0 | -1 | 0 |
| 567 | auaaagcuagauaaccgaaagu | mmu-miR-9* | -1 | 0 | 0 | -1 | 0 |
| 568 | ugagagaugccauucuauguaga | mmu-miR-741 | -1 | 0 | 0 | -1 | 0 |
| 569 | uucuaggacuuuauagagcagag | mmu-miR-1929 | -1 | 0 | 0 | -1 | 0 |
| 570 | ucgauucccugccaaugcac | mmu-miR-1939 | -1 | 0 | 0 | -1 | -1 |
| 571 | gccccugggccuauccuagaa | mmu-miR-331-3p | -1 | 0 | 0 | -1 | -1 |
| 572 | cugaccuaugaauugacagcc | mmu-miR-192 | -1 | 0 | 0 | -1 | -1 |
| 573 | aaugacacgaucacuc<u>ccg</u>uuga | mmu-miR-425 | -1 | 0 | 0 | -1 | -1 |
| 574 | uaagugccugcauguauaugcg | mmu-miR-467a | -1 | 0 | -1 | 1 | 0 |
| 575 | agaggcuggcacugggacacau | mmu-miR-1962 | -1 | 0 | -1 | 1 | -1 |
| 576 | cuauacgaccugcugccuuucu | mmu-let-7d* | -1 | 0 | -1 | 0 | 0 |
| 577 | gcaaagcacagggccugcagaga | mmu-miR-330* | -1 | 0 | -1 | 0 | 0 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 578 | uuaucagaaucuccagggguac | mmu-miR-361 | -1 | 0 | -1 | 0 | 0 |
| 579 | cuccugacuccagguccugugu | mmu-miR-378* | -1 | 0 | -1 | 0 | 0 |
| 580 | acucaaacugggggcucuuuug | mmu-miR-292-5p | -1 | 0 | -1 | 0 | 0 |
| 581 | ccaggaccaucag<u>ugug</u>acuau | mmu-miR-1933-3p | -1 | 0 | -1 | 0 | -1 |
| 582 | cuuuggauggagaaagaggggg | mmu-miR-1897-5p | -1 | 0 | -1 | 0 | -1 |
| 583 | ugc<u>auug</u>uauguguugacaugau | mmu-miR-669g | -1 | 0 | -1 | 0 | -1 |
| 584 | uuuggcaaugguagaacucacaccg | mmu-miR-182 | -1 | 0 | -1 | -1 | 0 |
| 585 | cugggagaaggcuguuuacucu | mmu-miR-30c-2* | -1 | 0 | -1 | -1 | 0 |
| 586 | aucucgcuggggccucca | mmu-miR-720 | -1 | 0 | -1 | -1 | -1 |
| 587 | ccgcacuguggguacuugcugc | mmu-miR-106b* | -1 | 0 | -1 | -1 | -1 |
| 588 | ggccgcccucucugguccuuca | mmu-miR-1900 | -1 | 0 | -1 | -1 | -1 |
| 589 | cagcagcacacugugguuugua | mmu-miR-497 | -1 | 0 | -1 | -1 | -1 |
| 590 | ucccuguccuccaggagcucacg | mmu-miR-339-5p | -1 | 0 | -1 | -1 | -1 |
| 591 | ccgcucguacucccgggggucc | mmu-miR-1901 | -1 | -1 | 1 | -1 | -1 |
| 592 | guc<u>cag</u>uuuucccaggaaucccu | mmu-miR-145 | -1 | -1 | 0 | 1 | -1 |
| 593 | aaaggcuaggcucacaaccaaa | mmu-miR-690 | -1 | -1 | 0 | 1 | -1 |
| 594 | gugaauuaccgaagggccauaa | mmu-miR-183* | -1 | -1 | 0 | 1 | -1 |
| 595 | aacugugucuuuucugaauaga | mmu-miR-881 | -1 | -1 | 0 | 0 | 1 |
| 596 | agagguaguagguugcauaguu | mmu-let-7d | -1 | -1 | 0 | 0 | 0 |
| 597 | ugagguaguagguuguauaguu | mmu-let-7a | -1 | -1 | 0 | 0 | 0 |
| 598 | guugcgg<u>acag</u>cgcuaggucgg | mmu-miR-1932 | -1 | -1 | 0 | 0 | 0 |
| 599 | ccc<u>cag</u>uguuuagacuaccuguuc | mmu-miR-199b* | -1 | -1 | 0 | 0 | -1 |
| 600 | uucaaguaauucaggauaggu | mmu-miR-26b | -1 | -1 | 0 | 0 | -1 |
| 601 | aucaacagacauuaauugggcgc | mmu-miR-421 | -1 | -1 | 0 | 0 | -1 |
| 602 | ucgaggagcuc<u>acag</u>ucuagu | mmu-miR-151-5p | -1 | -1 | 0 | 0 | -1 |
| 603 | <u>uagc</u>agcacaucaugguuuaca | mmu-miR-15b | -1 | -1 | 0 | 0 | -1 |
| 604 | uugugcuugaucuaaccaugu | mmu-miR-218 | -1 | -1 | 0 | 0 | -1 |
| 605 | gugccacugagcugauau<u>cagu</u> | mmu-miR-24-1* | -1 | -1 | 0 | 0 | -1 |
| 606 | cacagcucccaucucagaacaa | mmu-miR-674* | -1 | -1 | 0 | 0 | -1 |
| 607 | uauucauuuacuccccagccua | mmu-miR-664 | -1 | -1 | 0 | 0 | -1 |
| 608 | ugagguaguagauuguauaguu | mmu-let-7f | -1 | -1 | 0 | -1 | 0 |
| 609 | ugagguaguaaguuguauuguu | mmu-miR-98 | -1 | -1 | 0 | -1 | 0 |
| 610 | aacccguagauccgaucuugug | mmu-miR-99a | -1 | -1 | 0 | -1 | -1 |
| 611 | uuc<u>acag</u>uggcuaaguuccgc | mmu-miR-27a | -1 | -1 | 0 | -1 | -1 |
| 612 | aucac<u>auug</u>ccagggauuucc | mmu-miR-23a | -1 | -1 | 0 | -1 | -1 |
| 613 | uucaaguaauccaggauaggcu | mmu-miR-26a | -1 | -1 | 0 | -1 | -1 |

TABLE 1-continued

| | Detected miRNAs and their sorting in different cells | | | | | | |
|---|---|---|---|---|---|---|---|
| SEQ ID No | Sequence [Exosomal sorting motifs are in bold and cellular retention motifs are in underline | miRNAs | 3T3-L1 | C2C12 | SVEC | AML12 | RAT |
| 614 | uagcaccaucugaaaucgguua | mmu-miR-29a | -1 | -1 | 0 | -1 | -1 |
| 615 | uacccguagauccgaauuugug | mmu-miR-10a | -1 | -1 | 0 | -1 | -1 |
| 616 | ucccugagacccuaacuuguga | mmu-miR-125b-5p | -1 | -1 | 0 | -1 | -1 |
| 617 | ucaggcucaguccccucccgau | mmu-miR-484 | -1 | -1 | 0 | -1 | -1 |
| 618 | uagcaccauuugaaaucgguua | mmu-miR-29c | -1 | -1 | 0 | -1 | -1 |
| 619 | aacccguagauccgaacuugug | mmu-miR-100 | -1 | -1 | 0 | -1 | -1 |
| 620 | acaguagucugcacauugguua | mmu-miR-199a-3p | -1 | -1 | 0 | -1 | -1 |
| 621 | aagcugccaguugaagaacugu | mmu-miR-22 | -1 | -1 | 0 | -1 | -1 |
| 622 | uagcuuaucagacugauguuga | mmu-miR-21 | -1 | -1 | 0 | -1 | -1 |
| 623 | agcagcauuguacagggcuauca | mmu-miR-107 | -1 | -1 | 0 | -1 | -1 |
| 624 | ucccugagacccuuuaaccuguga | mmu-miR-125a-5p | -1 | -1 | 0 | -1 | -1 |
| 625 | uacccguagaaccgaauuugug | mmu-miR-10b | -1 | -1 | 0 | -1 | -1 |
| 626 | ucaggucccguucaggcgcca | mmu-miR-1274a | -1 | -1 | 0 | -1 | -1 |
| 627 | aaggagcucacagucuauugag | mmu-miR-28 | -1 | -1 | 0 | -1 | -1 |
| 628 | cauugcacuugucucggucuga | mmu-miR-25 | -1 | -1 | 0 | -1 | -1 |
| 629 | uggcucaguucagcaggaacag | mmu-miR-24 | -1 | -1 | 0 | -1 | -1 |
| 630 | acaguagucugcacauugguua | mmu-miR-199b | -1 | -1 | 0 | -1 | -1 |
| 631 | ugagguaguaguuuguacaguu | mmu-let-7g | -1 | -1 | 0 | -1 | -1 |
| 632 | ugagguaggagguuguauaguu | mmu-let-7e | -1 | -1 | 0 | -1 | -1 |
| 633 | agcuacauugucugcuggguuuc | mmu-miR-221 | -1 | -1 | 0 | -1 | -1 |
| 634 | acgccacauuucccacgccgcg | mmu-miR-2182 | -1 | -1 | 0 | -1 | -1 |
| 635 | uuuugcgauguguuccuaauau | mmu-miR-450a-5p | -1 | -1 | 0 | -1 | -1 |
| 636 | agcuacaucuggcuacugggu | mmu-miR-222 | -1 | -1 | 0 | -1 | -1 |
| 637 | uagcaccauuugaaaucaguguu | mmu-miR-29b | -1 | -1 | 0 | -1 | -1 |
| 638 | uucacaaagcccauacacuuuc | mmu-miR-350 | -1 | -1 | 0 | -1 | -1 |
| 639 | aaaaccuucagaaggaaagaa | mmu-miR-703 | -1 | -1 | 0 | -1 | -1 |
| 640 | auauaauacaaccugcuaagug | mmu-miR-374 | -1 | -1 | 0 | -1 | -1 |
| 641 | ugcuaugccaacauauugccauc | mmu-miR-31* | -1 | -1 | 0 | -1 | -1 |
| 642 | cacauuacacggucgaccucu | mmu-miR-323-3p | -1 | -1 | 0 | -1 | -1 |
| 643 | cuauaccaggaugucagcauaguu | mmu-miR-1949 | -1 | -1 | 0 | -1 | -1 |
| 644 | aaccaguaccuuucugagaaga | mmu-miR-470* | -1 | -1 | 0 | -1 | -1 |
| 645 | uuaaugcuaauugugauaaggggu | mmu-miR-155 | -1 | -1 | 0 | -1 | -1 |
| 646 | uauacauacacgcacacauaaga | mmu-miR-466e-3p | -1 | -1 | -1 | 1 | -1 |
| 647 | ucagugcaugacagaacuugg | mmu-miR-152 | -1 | -1 | -1 | 0 | -1 |
| 648 | aggcaguaguaguuagcugauugc | mmu-miR-34c | -1 | -1 | -1 | 0 | -1 |

TABLE 1-continued

| | Detected miRNAs and their sorting in different cells | | | | | | |
|---|---|---|---|---|---|---|---|
| SEQ ID No | Sequence [Exosomal sorting motifs are in bold and cellular retention motifs are in underline | miRNAs | 3T3-L1 | C2C12 | SVEC | AML12 | RAT |
| 649 | ugcccacccuuuac<u>cccg</u>cuc | mmu-miR-702 | -1 | -1 | -1 | 0 | -1 |
| 650 | uuuggca<u>cuag</u>cacauuuuugcu | mmu-miR-96 | -1 | -1 | -1 | -1 | 1 |
| 651 | ugugacagauugauaacugaaa | mmu-miR-542-3p | -1 | -1 | -1 | -1 | 0 |
| 652 | gaa<u>uuga</u>ucaggacauaggg | mmu-miR-805 | -1 | -1 | -1 | -1 | -1 |
| 653 | cucugugcugaaugucaaguu cugauu | mmu-miR-1944 | -1 | -1 | -1 | -1 | -1 |
| 654 | uucagugaugau<u>uag</u>cuucuga | mmu-miR-677 | -1 | -1 | -1 | -1 | -1 |
| 655 | cuccgugcacac<u>cccg</u>cgug | mmu-miR-715 | -1 | -1 | -1 | -1 | -1 |
| 656 | agaccacuuaucuaccaa<u>cagc</u> | mmu-miR-1839-3p | -1 | -1 | -1 | -1 | -1 |
| 657 | ugugcaauccaugcaaaacuga | mmu-miR-19b | -1 | -1 | -1 | -1 | -1 |
| 658 | ucagugcacuacagaacuuugu | mmu-miR-148a | -1 | -1 | -1 | -1 | -1 |
| 659 | aau<u>cccg</u>gacgagcccca | mmu-miR-1937a | -1 | -1 | -1 | -1 | -1 |
| 660 | ucagugcaucacagaacuuugu | mmu-miR-148b | -1 | -1 | -1 | -1 | -1 |
| 661 | uacaguacugugauaacugaa | mmu-miR-101a | -1 | -1 | -1 | -1 | -1 |
| 662 | aucacauugccagggauuacc | mmu-miR-23b | -1 | -1 | -1 | -1 | -1 |
| 663 | aagguuacuuguuaguucagg | mmu-miR-872 | -1 | -1 | -1 | -1 | -1 |
| 664 | cac<u>ccg</u>uagaaccgaccuugcg | mmu-miR-99b | -1 | -1 | -1 | -1 | -1 |
| 665 | ugugcaaucuaugcaaaacuga | mmu-miR-19a | -1 | -1 | -1 | -1 | -1 |
| 666 | <u>cagug</u>caauguuaaaagggcau | mmu-miR-130a | -1 | -1 | -1 | -1 | -1 |
| 667 | au<u>cccg</u>gacgagcccca | mmu-miR-1937b | -1 | -1 | -1 | -1 | -1 |
| 668 | cuauacaaucuacugucuuucc | mmu-let-7a* | -1 | -1 | -1 | -1 | -1 |
| 669 | uguaaacauccuacacucagcu | mmu-miR-30b | -1 | -1 | -1 | -1 | -1 |
| 670 | <u>uagc</u>agcacguaaauauuggcg | mmu-miR-16 | -1 | -1 | -1 | -1 | -1 |
| 671 | uguaaacaucccgacuggaag | mmu-miR-30d | -1 | -1 | -1 | -1 | -1 |
| 672 | uguaaacauccucgacuggaag | mmu-miR-30a | -1 | -1 | -1 | -1 | -1 |
| 673 | uacaguacugugau<u>agc</u>ugaa | mmu-miR-101b | -1 | -1 | -1 | -1 | -1 |
| 674 | uguaaacauccacacucucagc | mmu-miR-30c | -1 | -1 | -1 | -1 | -1 |
| 675 | cuuu<u>cagu</u>cggauguuuacagc | mmu-miR-30e* | -1 | -1 | -1 | -1 | -1 |
| 676 | uucacaguggcuaaguucugc | mmu-miR-27b | -1 | -1 | -1 | -1 | -1 |
| 677 | uguaaacauccuugacuggaag | mmu-miR-30e | -1 | -1 | -1 | -1 | -1 |
| 678 | agcagcauuguacagggcuauga | mmu-miR-103 | -1 | -1 | -1 | -1 | -1 |
| 679 | <u>uagc</u>agcacauaaugguuugug | mmu-miR-15a | -1 | -1 | -1 | -1 | -1 |
| 680 | uguaacagcaacuccaugugga | mmu-miR-194 | -1 | -1 | -1 | -1 | -1 |
| 681 | ugagaacugaauuccauaggcu | mmu-miR-146b | -1 | -1 | -1 | -1 | -1 |
| 682 | ugagguaguaguuugugcuguu | mmu-let-7i | -1 | -1 | -1 | -1 | -1 |
| 683 | au<u>cccg</u>gaagagcccca | mmu-miR-1937c | -1 | -1 | -1 | -1 | -1 |

TABLE 1-continued

Detected miRNAs and their sorting in different cells

| SEQ ID No | Sequence [Exosomal sorting motifs are in bold and cellular retention motifs are in underline | miRNAs | 3T3-L1 | C2C12 | SVEC | AML12 | RAT |
|---|---|---|---|---|---|---|---|
| 684 | uaccacaggguagaaccacgg | mmu-miR-140* | -1 | -1 | -1 | -1 | -1 |
| 685 | cagug<u>guuuu</u>acccuaugguag | mmu-miR-140 | -1 | -1 | -1 | -1 | -1 |
| 686 | aagguagauagaa<u>ca</u>ggucuug | mmu-miR-1839-5p | -1 | -1 | -1 | -1 | -1 |
| 687 | <u>uagc</u>agcacagaaauauuggc | mmu-miR-195 | -1 | -1 | -1 | -1 | -1 |
| 688 | cuuuca<u>gu</u>cggauguuugcagc | mmu-miR-30a* | -1 | -1 | -1 | -1 | -1 |
| 689 | uaaagugcuga<u>ca</u>gugcagau | mmu-miR-106b | -1 | -1 | -1 | -1 | -1 |
| 690 | cagcagcaauucauguuuugga | mmu-miR-322 | -1 | -1 | -1 | -1 | -1 |
| 691 | aguuuucccuucaagucaa | mmu-miR-684 | -1 | -1 | -1 | -1 | -1 |
| 692 | guguugaaacaaucucuacug | mmu-miR-653 | -1 | -1 | -1 | -1 | -1 |
| 693 | gccugcugggguggaaccuggu | mmu-miR-370 | -1 | -1 | -1 | -1 | -1 |
| 694 | uaugugccuuuggacuacaucg | mmu-miR-455* | -1 | -1 | -1 | -1 | -1 |
| 695 | ugauauguuugauauauuaggu | mmu-miR-190 | -1 | -1 | -1 | -1 | -1 |
| 696 | cguacaaccuu<u>cuag</u>cuuucc | mmu-let-7c-1* | -1 | -1 | -1 | -1 | -1 |
| 697 | ucucccuucaugu<u>g</u>cccaga | mmu-miR-343 | -1 | -1 | -1 | -1 | -1 |
| 698 | ugagaacugaauuccauggguu | mmu-miR-146a | -1 | -1 | -1 | -1 | -1 |
| 699 | ugau<u>u</u>guccaaacgcaauucu | mmu-miR-219 | -1 | -1 | -1 | -1 | -1 |
| 700 | gugccuacugagcuga<u>aacagu</u> | mmu-miR-24-2* | -1 | -1 | -1 | -1 | -1 |
| 701 | AGGCAGUGUGUGUAGCUGAUUGC | miR-34c-5p-UGUG | Not availa ble (N/A) | N/A | N/A | N/A | N/A |
| 702 | AGGCAGUGUAGUUAGCU<u>C</u>AU<u>G</u>GC | miR-34c-5p-CAUG | N/A | N/A | N/A | N/A | N/A |
| 703 | AGGCAGUGUAGUUAGC<u>GGGA</u>GGC | miR-34c-5p-CGGGAG | N/A | N/A | N/A | N/A | N/A |
| 704 | GCAGCUUUCAGAU<u>C</u>UGGCUGUAA | miR-693-3p-mut | N/A | N/A | N/A | N/A | N/A |

As shown in FIG. 4A, 6 main nucleotide motifs in the mature miRNAs were identified that were significantly more abundant in the miRNAs that had preferential sorting to exosomes. All values for individual cell types indicates the percentage of miRNAs in the exosome fraction of that cell type that contained a given motif. The "total" value represents the percentage of miRNAs from each cell types that contained at least one miRNA containing one of the motifs. These motifs could be found anywhere in the miRNA sequence.

The presence of these specific sequences was able to explain between 62-70% of the miRNA enrichment in the exosomes of the different cell lines. One of these sequences (GGAG) was previously reported to mediate exosome sorting in a cell type not studied here (human lymphoblasts, see Ritchie 2015), which suggests that these motifs might be evolutionarily conserved.

Interestingly, BAT (FIG. 5A), C2C12 (FIG. 5B) and 3T3-L1 (FIG. 5C) show a very similar pattern in the abundance of these exosomal sorting motifs, predominantly using UGUG; CAUG; or CUGG. In contrast, AML12 (FIG. 5D) and SVEC (FIG. 5E) predominantly use A/CGGG; CUGG; or GGAG exosomal sorting motifs.

Likewise, nucleotide motifs that might be associated with cellular enrichment and guide their retention were investigated. As shown in FIG. 4B, five nucleotides sequences in the mature miRNA were significantly more abundant in those miRNAs that were retained in the cell. In this case, these five motifs were able to explain 34-56% of the miRNAs significantly enriched in the cells. As shown in FIG. 5, there is a clear hierarchy in the abundance of these cellular enrichment motifs, being CAGU>ACAG>AUUG>UAGC>CCCG in almost all the cases.

Thus, these data describe sorting motifs for enrichment of miRNAs in exosomal and cellular fractions. Some of these miRNA motifs were unique to particular types of cells, while other motifs were found across a range of cell types.

Example 6. Introduction or Removal of Motifs

In order to analyze whether the discovered motifs play a role in exosome sorting, experiments were performed to introduce or remove some of these motifs. Wild-type sequences for pre-miR-34c and pre-miR-693 and their flanking genomic 100 base pairs upstream and downstream were obtained from Ensembl database, flanked by restriction enzyme sites and ordered through Integrated DNA Technologies. For the mutations of the sequences in order to introduce or remove exosomal motifs, indicated nucleotides were changed in the guide strand sequence as well as complementary nucleotides in the passenger strand to maintain the same pre-miRNA structure, as predicted by RNAfold Web Server (University of Wien). These sequences were equally flanked by genomic 100 bp upstream and downstream and restriction enzymes. For both wild-type and mutated version, the sequences were cloned into the backbone lentivirus vector upon removal of the scramble miRNA cassette (MMIR000, System Biosciences). Plasmids were used to transfect BAT pre-adipocytes and positively incorporated cells were selected 6 days later by Flow Cytometry (MoFlo Cell Sorter, Beckman Coulter) for GFP signal.

Figures 6A, 6B:
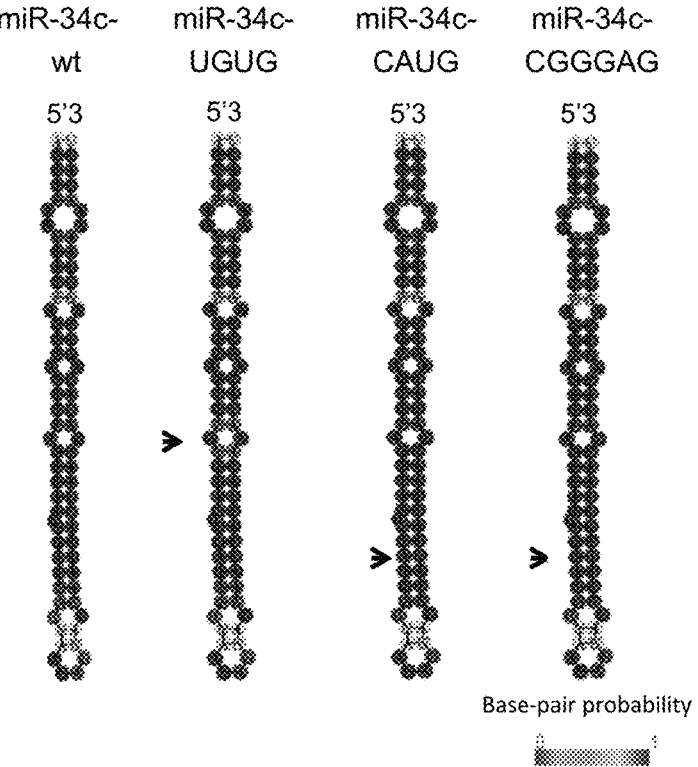
FIGS. 6A-6F show the effects of introducing or removing some sorting motifs.
Figures 6C, 6D:
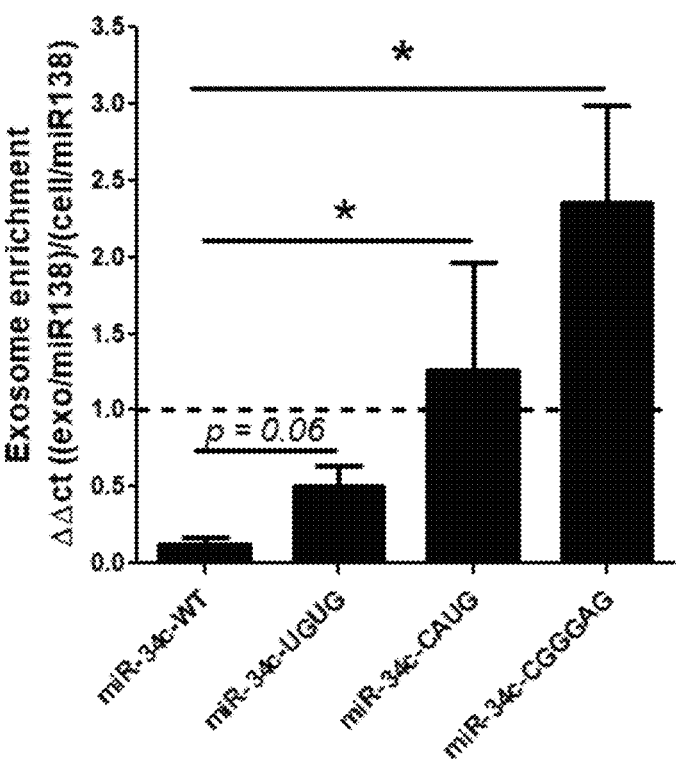

Exosome isolation was performed again by ultracentrifugation method. RNA was isolated from the exosomes and cell bodies by TRIzol method. In order to measure the presence of the wild-type or mutated versions of miR-34c-5p and miR-693-3p, RNA was retrotranscribed by miR-CURY LNA RT Kit (Qiagen 339320) following manufacturer's instructions. Specific LNA primers (Qiagen) were used in quantitative real-time PCR (qPCR) to distinguish wild-type and mutated versions of these two miRNAs. Expression for each miRNA was normalized respect to miR-138-5p, which has expression essentially identical between exosomes and cells.

miR-34c-5p (SEQ ID NO: 648) is a miRNA that was significantly enriched in the cell bodies of all cell types except hepatocytes (Table 1). The motifs UGUG or CAUG were introduced towards the 3' end of the miR-34c-5p sequence with minimal changes in the miRNA sequence (FIG. 6A) in order to maintain the normal pre-miRNA structure (FIG. 6B), which is essential to display a regular processing by Dicer and potential recognition by RNA-binding proteins (RBPs) (see Bartel D P. *Cell* 173(1):20-51 (2018) and Dominguez D et al., *Mol Cell* 70(5):854-867.e9 (2018)). Expectedly, when the wild-type version of miR-34c-5p was introduced, there was a higher presence in the cell body compared to the exosome fraction. However, when the mutant versions were introduced there was a shift in the mutated miR-34c-5p distribution, with expression being much more abundant in the exosomal fraction for both motifs and leading to a nearly statistically significant 4-fold enhancement of exosomal enrichment by UGUG introduction (SEQ ID NO: 701) and a significant 10-fold increase by CAUG introduction (SEQ ID NO: 702) (FIG. 6C).

Additionally, a novel 6-mer motif CGGGAG combining two shorter identified motifs, CGGG & GGAG, was introduced in a CGGGAG mutant (SEQ ID NO: 703). The novel motif displays a 24- to 80-fold enrichment in exosome-enriched miRNAs from endothelial cells and hepatocytes. Due to this huge enrichment, the CGGGAG was termed a SuperEXOmotif. In this case, exosomal abundance was increased to a larger extent, leading to a final enrichment of 20-fold in abundance in exosomes versus cell bodies, which is much higher than the other motifs (FIG. 6C). Very interestingly, the introductions of the EXOmotif CAUG and SuperEXOmotif CGGGAG implied a complete shift in miRNA distribution from a very cellular-prone miRNA to a highly exosomal enriched miRNA (FIG. 6C). These data clearly suggest that these motifs play a role in miRNA sorting to exosomes.

Figure 6E:
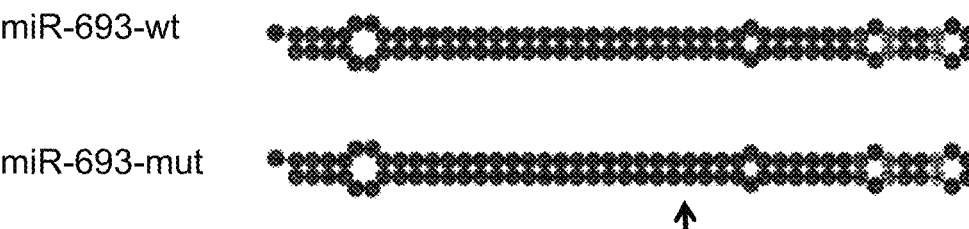
Figure 6F:
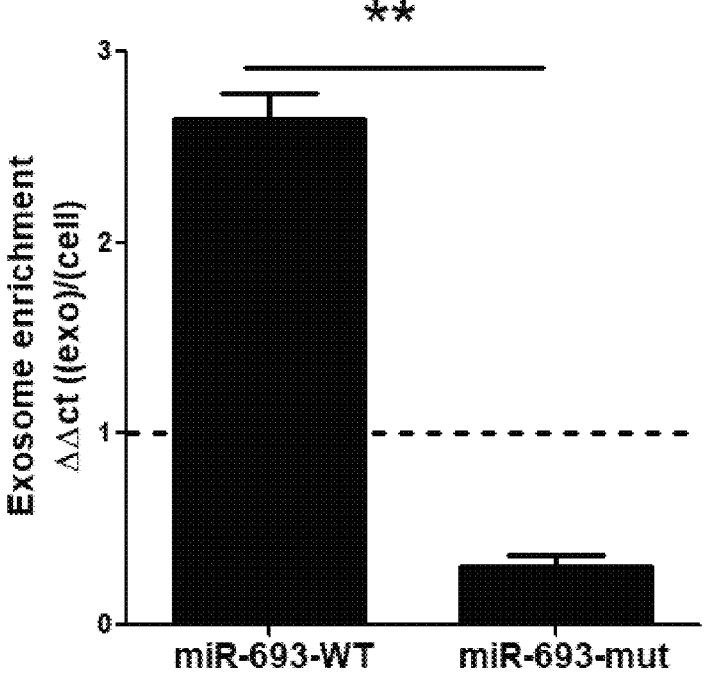

In addition, the impact of removal of the identified exosome motif UGUG on exosome sorting was assessed. Wild-type miR-693-3p (SEQ ID NO: 6) is normally enriched in the exosomal fraction of all cell types. A mutated version of miR-693-3p lacking a UGUG motif (SEQ ID NO: 704) was studied. Again, these minor changes in the sequence (FIG. 6D) did not alter the expected secondary structure of this miRNA (FIG. 6E). When the wild-type version was overexpressed, miR-693-3p was found enriched in the exosome fraction. However, when the mutated version of miR-693-3p lacking a UGUG motif showed partially impaired sorting (FIG. 6F), again suggesting that this motif could be important for exporting miRNA into exosomes.

Example 7. Embodiments

The following numbered items provide embodiments as described herein, though the embodiments recited here are not limiting.

Item 1. A method for producing exosomes or exosome-like vesicles comprising miRNA in vitro comprising:
modifying a miRNA to include at least one exosomal sorting motif and/or removing any cellular retention motifs;
introducing the modified miRNA into a cell capable of producing an exosome or exosome-like vesicle under conditions that will result in expression of the modified miRNA; and
optionally, collecting the produced exosomes or exosome-like vesicles, wherein the exosomal sorting motif is UGUG, GGAG, CAUG, GGCA/G, A/CGGG, CUGG, or CGGGAG, and the cell retention motif, if present, is CAGU, ACAG, AUUG, UAGC, or CCCG.

Item 2. A method of treating a subject in need of gene silencing comprising administering to the subject an exosome, wherein the exosome is produced in vitro by a) modifying a miRNA to include at least one exosomal sorting motif and/or removing any cellular retention motifs, and b) introducing the modified miRNA into an exosome- or exosome-like vesicle producing cell under conditions that will result in expression of the modified miRNA, and collecting the produced exosome comprising the modified miRNA, wherein the exosomal sorting motifs is selected from UGUG, GGAG, CAUG, GGCA/G, A/CGGG, CUGG, and CGGGAG and the cellular retention motif, if present, is selected from CAGU, ACAG, AUUG, UAGC, and CCCG.

Item 3. The method of item 1 or 2, wherein the miRNA comprises one exosomal sorting motif.

Item 4. The method of item 1 or 2, wherein the miRNA comprises more than one exosomal sorting motif.

Item 5. The method of item 1, further comprising administering the exosome or exosome-like vesicle to a subject.

Item 6. The method of item 1 or 2, wherein modifying the miRNA with an exosomal sorting motif results in more miRNA in the exosome as compared to an exosome produced with a miRNA not modified with an exosomal sorting motif.

Item 7. The method of item 1 or 2, wherein the removal of the cellular retention motif results in more miRNA in the exosome as compared to an exosome produced with a miRNA comprising a cellular retention motif.

Item 8. The method of item 1 or 2, wherein the miRNA contains a cell retention motif and wherein the cell retention motif is removed.

Item 9. A method for retaining miRNA inside a cell in vitro comprising:

modifying a miRNA to include at least one cell retention motif and/or removing any exosomal sorting motifs; and introducing the modified miRNA into a cell capable of producing an exosome or exosome-like vesicle under conditions that will result in expression of the modified miRNA, wherein the cell retention motif is CAGU, ACAG, AUUG, UAGC, or CCCG, and the exosomal sorting motif, if present is UGUG, GGAG, CAUG, GGCA/G, A/CGGG, CUGG, or CGGGAG.

Item 10. A method for treating a subject in need of gene silencing comprising:

collecting the subject's cells and manipulating them ex vivo to express a miRNA having at least one cellular retention motif and/or removing any exosomal sorting motifs, and administering the ex vivo manipulated cell comprising the modified miRNA to the same or different subject from which it was collected, wherein the cellular retention motif is selected from CAGU, ACAG, AUUG, UAGC, and CCCG, and the exosomal sorting motif, if present, is selected from UGUG, GGAG, CAUG, GGCA/G, A/CGGG, CUGG, and CGGGAG.

Item 11. The method of item 9 or 10, wherein the miRNA comprises one cellular retention motif.

Item 12. The method of item 9 or 10, wherein the miRNA comprises more than one cellular retention motif.

Item 13. The method of item 9 or 10, wherein the addition of the cellular retention motif reduces the export of the miRNA into an exosome or exosomal-like vesicle.

Item 14. The method of item 9 or 10, wherein the removal of the exosomal sorting motif reduces the export of the miRNA into an exosome or exosomal-like vesicle.

Item 15. The method of item 9, further comprising administering the cell to a subject.

Item 16. The method of item 10 or 15, wherein the miRNA levels in non-implanted cell-types after administration to the subject are reduced as compared to levels in subject administered a non-modified miRNA containing cell.

Item 17. The method of any one of the preceding items, wherein the cell is an adipocyte, muscle cell, hepatocyte, or vascular endothelial cell.

Item 18. The method of item 17, wherein the adipocyte is a white adipocyte or brown adipocyte.

Item 19. The method of item 18, wherein the white adipocyte is a 3T3-L1 cell.

Item 20. The method of item 18, wherein the brown adipocyte is a BAT cell.

Item 21. The method of item 17, wherein the muscle cell is a C2C12 cell.

Item 22. The method of item 17, wherein the hepatocyte is an AML12 cell.

Item 23. The method of item 17, wherein the vascular endothelial cell is a SVEC cell.

Item 24. The method of item 1 or 2, wherein the cell is a hepatocyte or endothelial cell and the exosomal sorting motif is A/CGGG; CUGG; GGAG; or CGGGAG.

Item 25. The method of item 1 or 2, wherein the cell is a brown or white adipocyte or muscle cell and the exosomal sorting motif is UGUG; CAUG; CUGG; or CGGGAG.

Item 26. The method of any one of the preceding items, wherein the miRNA is any one of the miRNAs of SEQ ID Nos: 1-704.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method for producing exosomes or exosome-like vesicles comprising miRNA in vitro comprising:

a. introducing a miRNA modified to include at least one exosomal sorting motif and/or to remove at least one cellular retention motif into a cell capable of producing an exosome or exosome-like vesicle, wherein the at least one exosomal sorting motif is selected from UGUG, CAUG, GGCA, AGGG, CUGG, and CGGGAG, and the at least one cell retention motif is selected from CAGU, ACAG, and UAGC; and b. optionally, collecting the exosomes or exosome-like vesicles produced by the cell.

2. The method of claim 1, wherein the modified miRNA comprises one of the at least one exosomal sorting motif.

3. The method of claim 1, wherein the modified miRNA comprises more than one of the at least one exosomal sorting motif.

4. The method of claim 1, further comprising administering the collected exosomes or exosome-like vesicles to a subject.

5. The method of claim 1, wherein the modified miRNA of (a) with the at least one exosomal sorting motif results in more miRNA in the collected exosomes or exosome-like vesicles as compared to exosomes or exosome-like vesicles produced with the miRNA of (a) prior to being modified with the at least one exosomal sorting motif.

6. The method of claim 1, wherein the removal of the at least one cellular retention motif results in more miRNA in the collected exosomes or exosome-like vesicles as compared to exosomes or exosome-like vesicles produced with the miRNA of (a) prior to removal of the at least one cellular retention motif.

7. The method of claim 1, wherein:

a. the cell is a hepatocyte or endothelial cell and the at least one exosomal sorting motif is selected from AGGG, CUGG, and CGGGAG; or b. the cell is a brown or white adipocyte or muscle cell and the at least one exosomal sorting motif is selected from UGUG, CAUG, CUGG and CGGGAG.

8. The method of claim 1, wherein the method comprises, after (b), collecting the exosomes or exosome-like vesicles produced by the cell.

9. The method of claim 1, wherein the at least one exosomal sorting motif is CGGGAG.

\* \* \* \* \*